US012435089B2

(12) United States Patent
Li et al.

(10) Patent No.: US 12,435,089 B2
(45) Date of Patent: Oct. 7, 2025

(54) 3-OXADIAZOLYL SUBSTITUTED PYRAZOLO[1,5,A]PYRIMIDINES FOR ROS1, NTRK, AND ALK MEDIATED DISEASES

(71) Applicant: TYK MEDICINES, INC., Zhejiang (CN)

(72) Inventors: Jun Li, Zhejiang (CN); Chengshan Niu, Zhejiang (CN); Apeng Liang, Zhejiang (CN); Yusheng Wu, Zhejiang (CN)

(73) Assignee: TYK MEDICINES, INC., Zhejiang (CN)

(*) Notice: Subject to any disclaimer, the term of this patent is extended or adjusted under 35 U.S.C. 154(b) by 935 days.

(21) Appl. No.: 17/521,153

(22) Filed: Nov. 8, 2021

(65) Prior Publication Data

US 2022/0089603 A1 Mar. 24, 2022

Related U.S. Application Data

(63) Continuation-in-part of application No. PCT/CN2020/089067, filed on May 7, 2020.

(30) Foreign Application Priority Data

May 8, 2019 (CN) ......................... 201910379104.0

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 8,088,779 B2 * | 1/2012 | Hossner | A61P 25/24 | 514/259.3 |
| 2009/0118284 A1 * | 5/2009 | Cooper | C07D 403/14 | 514/252.19 |
| 2016/0168156 A1 * | 6/2016 | Kim | A61P 29/00 | 514/233.2 |
| 2023/0136194 A1 | 5/2023 | Jin et al. | | |
| 2024/0025908 A1 * | 1/2024 | Li | A61K 31/5395 | |

FOREIGN PATENT DOCUMENTS

| | | | |
|---|---|---|---|
| CN | 102596957 | A | 7/2012 |
| CN | 104619708 | A | 5/2015 |
| CN | 107207514 | A | 9/2017 |
| CN | 111171019 | A | 5/2020 |
| JP | 2013537199 | A | 9/2013 |
| JP | 2015520205 | A | 7/2015 |
| SG | 11202250450 | M | 6/2021 |
| WO | 2005047266 | A1 | 5/2005 |
| WO | 2007025540 | A2 | 3/2007 |
| WO | 2010/033941 | A1 | 3/2010 |
| WO | 2010/048314 | A1 | 4/2010 |
| WO | 2010071885 | A1 | 6/2010 |
| WO | 2011006074 | A1 | 1/2011 |
| WO | 2011/146336 | A1 | 11/2011 |
| WO | 2012/116217 | A1 | 8/2012 |
| WO | 2013183578 | A1 | 12/2013 |
| WO | 2016097869 | A1 | 6/2016 |
| WO | 2020/114499 | A1 | 6/2020 |
| WO | 2020224626 | A1 | 11/2020 |
| WO | WO-2024193678 | A1 * | 9/2024 |

OTHER PUBLICATIONS

Wang et al. "Structure-Guided Design, Synthesis, and Biological Evaluation of (2-(1H-Indol-3-yl)-1H-imidazol-4-yl)(3,4,5-trimethoxyphenyl) Methanone (ABI-231) Analogues Targeting the Colchicine Binding Site in Tubulin" J Med Chem 2019, 62, 6734-6750. DOI: 10.1021/acs.jmedchem.9b00706 (Year: 2019).*

Katayama et al. "The new-generation selective ROS1/NTRK inhibitor DS-6051b overcomes crizotinib resistant ROS1-G2032R mutation in preclinical models" Nature Communications, 2019, 10, 3604, 1-12. DOI: 10.1038/s41467-019-11496-z (Year: 2019).*

Greco A. et al., "The DNA rearrangement that generates the TRK-T3 oncogene involves a novel gene on chromosome 3 whose product has a potential coiled-coil domain", Molecular and cellular biology, Nov. 1995, vol. 15, No. 11, pp. 6118-6127.

(Continued)

*Primary Examiner* — Kortney L. Klinkel
*Assistant Examiner* — Sophia Reilly
(74) *Attorney, Agent, or Firm* — NKL Law; Bin Lu; Allen Xue

(57) ABSTRACT

Provided is the compound represented by formula I, or tautomer thereof, or meso thereof, racemate thereof, and mixture of meso and racemate thereof, or enantiomer thereof, diastereomer, and mixture of enantiomer and diastereomer, or pharmaceutically acceptable salt thereof, or deuterate thereof. The compound of formula I can be used as a kinase inhibitor, as a drug for the treatment of ROS1, NTRK, ALK, and other kinase-mediated diseases.

I

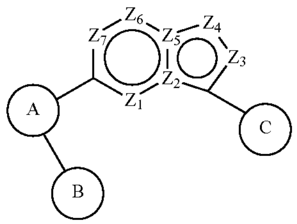

11 Claims, No Drawings

(56) References Cited

OTHER PUBLICATIONS

Greco A. et al., "Role of the TFG N-terminus and coiled-coil domain in the transforming activity of the thyroid TRK-T3 oncogene", Oncogene, 1998, 16(6), pp. 809-816.

Russo M et al., "Acquired resistance to the TRK inhibitor entrectinib in colorectal cancer", Cancer discovery, Nov. 6, 2016, 6(1), pp. 36-44.

Drilon A et al., "What hides behind the MASC: clinical response and acquired resistance to entrectinib after ETV6-NTRK3 identification in a mammary analogue secretory carcinoma (MASC)", Annals of Oncology, 2016, 27(5): pp. 920-926.

Ryohei Katayama et al., "The new-generation selective ROS1/NTRK inhibitor DS-6051b overcomes crizotinib resistant ROS1-G2032R mutation in preclinical models", Nature Communications, vol. 10, No. 1, Aug. 9, 2019, pp. 1-12.

* cited by examiner

3-OXADIAZOLYL SUBSTITUTED PYRAZOLO[1,5,A]PYRIMIDINES FOR ROS1, NTRK, AND ALK MEDIATED DISEASES

TECHNICAL FIELD

The invention relates to the technical field of medicine, in particular to a compound used as a kinase inhibitor, a preparation method thereof, and a use for preparing a medicament for treating diseases mediated by kinase such as ROS1, NTRK, ALK, etc.

BACKGROUND OF THE INVENTION

Tropomyosin receptor kinase (TRK) family belongs to transmembrane receptor tyrosine kinases (RTKs), which are involved in regulating synaptic growth and function maintenance, memory generation and development, and protecting neurons from damage, etc. in mammalian nervous system. TRK kinase is a kind of nerve growth factor receptor. Its family consists of Tropomyosin-related kinase A (TRKA), Tropomyosin-related kinase B (TRK B) and Tropomyosin-related kinase C (TRK C), which are highly homologous and encoded by NTRK 1, NTRK 2 and NTRK 3 genes, respectively. Complete TRK kinase consists of extracellular domain, transmembrane domain and intracellular domain. Like other RTKs, the extracellular domain of TRK kinase binds with corresponding ligands to form dimer, which can cause autophosphorylation of intracellular domain of TRK kinase to activate its kinase activity and further activate downstream signal transduction pathway. TRK kinase affects cell proliferation, differentiation, metabolism and apoptosis through downstream pathways such as Ras/MAPK, PI3K/AKT and PLC γ. When the NTRKs gene is fused or mutated, the extracellular receptor is altered or eliminated (Greco, A. et. al, Mol. Cell. Biol. 1995, 15, 6118; Oncogene 1998, 16, 809), but the fused or mutated TRK protein is in a highly activated kinase activity state without ligand binding, which can continuously activate the downstream signal transduction pathway, causing the regulation disorder of the downstream signal pathway of TRK kinase, inducing cell proliferation and promoting the occurrence and development of tumor. NTRKs gene fusion occurs in a variety of solid tumors in adults and children, including breast cancer, colorectal cancer, non-small cell lung cancer, papillary thyroid cancer, Spitz-like melanoma, glioma and various sarcomas, etc. In common cancers, such as non-small cell lung cancer and colorectal cancer, the incidence of NTRK gene fusion is lower, about 1%-3%, but in some rare cancers, such as infantile fibrosarcoma and secretory breast cancer, the incidence of NTRK gene fusion can reach more than 90%. The earliest TPM3-TRKA fusion protein was found in colon cancer cells. Later, more types of NTRK fusion proteins such as CD74-NTRKA, MPRIP-NTEKA, QKI-NTRKB, ETV6-NTRKC, BTB1-NTRKC, etc. were found in different clinical tumor patients such as breast cancer, non-small cell lung cancer, papillary thyroid cancer, Spitz-like melanoma, glioma, etc. Therefore, in recent years, NTRK fusion protein has become an effective anti-cancer target, and has become a hot spot in the research and development of anti-cancer drugs. With the further understanding of TRK kinase in recent years, more TRK fusion protein types and mutation types have been found (Russo, M. et. al Cancer Discovery, 2016, 6, 36; Drilon, A. et. al, Annals of Oncology, 2016, 27, 920), so it is urgent to develop new NTRK inhibitors with better activity and wider effects in clinic, so as to solve the tumor treatment problems caused by these NTRK protein fusion or mutation.

ROS1 (c-ros oncogene 1 receptor kinase) is a tyrosine protein kinase encoded by ROS1 proto-oncogene in human body. It is located on chromosome 6q22. 1 and belongs to the tyrosine kinase insulin receptor gene. It is composed of intracellular tyrosine kinase active region, transmembrane region and extracellular region, and encodes chimeric protein with tyrosine kinase activity. The basic structure consists of extracellular N-terminal ligand binding region (amino acid 1-1861), transmembrane region (amino acid 1862-1882) and intracellular C-terminal tyrosine kinase active region (amino acid 1883-2347) consisting of 464 amino acids. When ROS1 gene rearranges, the extracellular region is lost, and the transmembrane region and intracellular tyrosine kinase region are retained. The rearrangement sites mainly occur in exons 32-36 of ROS1 gene. ROS1 gene mutation mainly occurs in lung cancer patients, and the proportion of patients is 1%-2%. In NSCLC, ROS1 gene mainly fuses with SLC34A2 and CD74, and continuously activates ROS1 tyrosine kinase region and downstream JAK/STAT, PI3K/AKT, RAS/MAPK signaling pathways, thus causing tumor occurrence. It has been proved in a large number of literatures and clinically that diseases caused by ROS1 overactivation, especially cancer, can be treated by inhibiting the activity of mutated ROS1 kinase. At present, crizotinib and entrotinib are on the market for the treatment of ROS1 positive non-small cell lung cancer, both of which belong to the first generation of small molecule ROS1 inhibitors. However, during the treatment of crizotinib or entrotinib, drug resistance and disease progression will occur in about 15 months. Among drug-resistant patients, the most common drug-resistant mutation is solvent front mutation such as G2032R. For drug-resistant patients, there are no therapeutic drugs on the market at present. Therefore, it is urgent to develop new inhibitors against ROS1, especially new ROS1 inhibitors that are resistant to the first generation of ROS1 inhibitors such as crizotinib or entrotinib, for clinical treatment.

2-5% of NSCLC patients are anaplastic lymphoma kinase (ALK) rearrangements, a receptor protein tyrosine phosphokinase in the insulin receptor superfamily. At first, people found ALK in the form of an activated fusion oncogene in anaplastic large cell lymphoma, and then continuous studies found the fusion form of ALK in various cancers, including systemic dysplasia, inflammatory myofibroblastic carcinoma, non-small cell lung cancer, etc. The mutation and abnormal activity of ALK in a variety of cancers have made it a drug target for the treatment of ALK-positive cancers. At present, there are many ALK kinase inhibitors on the market. With the clinical application of these drugs, patients will have drug resistance mutations. If G1202R and other drug resistance mutations occur, these drugs will lose their efficacy.

In recent years, with the further understanding of ROS1, NTRK, ALK and other kinases, and the increase of clinical drug-resistant patients, it is urgent to develop new tyrosine kinase inhibitors with better activity and wider effects in clinic, so as to solve the treatment problems of tumors caused by the fusion or mutation of ROS1, NTRK, ALK and other kinases.

SUMMARY OF THE INVENTION

The invention provides a novel, efficient and broad-spectrum kinase inhibitor capable of simultaneously acting on carcinogenic proteins such as NTRK, ALK and/or ROS1.

In the first aspect of the invention, a compound represented by formula I, or a tautomer thereof, or a mesomer thereof, a racemate thereof and a mixture of the mesomer and the racemate thereof, or an enantiomer thereof, a diastereomer thereof and a mixture of the enantiomer and the diastereomer thereof, or a pharmaceutically acceptable salt thereof, or a deuterated compound thereof is provided:

I

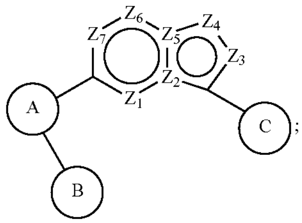

;

in formula I:

A is

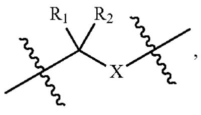

, wherein X is independently selected from the group consisting of $NR_6$, O, $CR_1R_2$, S, S(O) or $S(O)_2$;

B is selected from the group consisting of monocyclic aromatic hydrocarbon, bicyclic aromatic hydrocarbon, monocyclic heteroaromatic hydrocarbon or bicyclic heteroaromatic hydrocarbon, wherein, H on any carbon atom of B can be substituted by the following substituents: halogen, hydroxy, amino, cyano, acyl, ester, alkyl, cycloalkyl, alkylamino, alkoxy, cycloalkoxy, aryl, heteroaryl, monosubstituted or polysubstituted alkyl, monosubstituted or polysubstituted alkoxy, monosubstituted or polysubstituted cycloalkyl, monosubstituted or polysubstituted cycloalkoxy, monosubstituted or polysubstituted aryl, monosubstituted or polysubstituted heteroaryl; the substituents of the mono-substituted or polysubstituted alkyl, mono-substituted or polysubstituted alkoxy, mono-substituted or polysubstituted cycloalkyl, mono-substituted or polysubstituted cycloalkoxy, mono-substituted or polysubstituted aryl, and mono-substituted or polysubstituted heteroaryl are independently selected from the group consisting of deuterium, halogen, amino, cyano, hydroxyl, acyl, ester, alkyl, haloalkyl, cycloalkyl, halocycloalkyl, alkoxy, haloalkoxy, aryl and hetero aryl;

C is independently

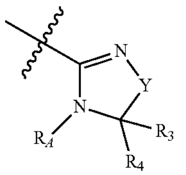

or

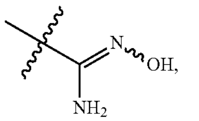

where Y is independently selected from the group consisting of O, $NR_A$ or $CR_1R_2$, ~ represents Z shape or E shape;

wherein $R_1$ and $R_2$ are each independently selected from the group consisting of hydrogen, halogen, amino, cyano, hydroxy, acyl, ester, alkyl, alkoxy, cycloalkyl, aryl, heteroaryl, monosubstituted or polysubstituted alkyl, monosubstituted or polysubstituted alkoxy, monosubstituted or polysubstituted cycloalkyl, monosubstituted or polysubstituted aryl, monosubstituted or polysubstituted heteroaryl; the substituents of the mono-substituted or polysubstituted alkyl, mono-substituted or polysubstituted alkoxy, mono-substituted or polysubstituted cycloalkyl, mono-substituted or polysubstituted aryl, and mono-substituted or polysubstituted heteroaryl are independently selected from the group consisting of deuterium, halogen, amino, cyano, hydroxyl, acyl, ester, alkyl, haloalkyl, cycloalkyl, halocycloalkyl, alkoxy, haloalkoxy, aryl and heteroaryl; or $R_1$ and $R_2$ together with the C atom attached to them form substituted or unsubstituted 3-7 membered cycloalkane, aza-cycloalkane, oxa-cycloalkane or thio-cycloalkane; wherein the substituted means being substituted by one or more groups selected from the group consisting of alkyl, acyl, ester, sulfonyl, and sulfinyl;

$R_3$ and $R_4$ are each independently selected from the group consisting of hydrogen, amino, hydroxy, acyl, ester, alkyl, cycloalkyl, aryl, heteroaryl, monosubstituted or polysubstituted alkyl, monosubstituted or polysubstituted alkoxy, monosubstituted or polysubstituted cycloalkyl, monosubstituted or polysubstituted aryl, and monosubstituted or polysubstituted heteroaryl; the substituents of the mono-substituted or polysubstituted alkyl, mono-substituted or polysubstituted alkoxy, mono-substituted or poly substituted cycloalkyl, mono-substituted or polysubstituted aryl, and mono-substituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and heteroaryl;

or $R_3$ and $R_4$ together with the C atom attached to them form substituted or unsubstituted 3-7 membered cycloalkane, aza-cycloalkane, oxa-cycloalkane, thio-cycloalkane or oxo(=O); or $R_A$ and $R_4$ together with the atom attached to them form substituted or unsubstituted 3-7 membered cycloalkane, aza-cycloalkane, oxa-cycloalkane or thio-cycloalkane; or $R_3$ fuses with Y to form substituted or unsubstituted 3-7 membered cycloalkane, aza-cycloalkane, oxa-cycloalkane or thio-cycloalkane; wherein the substituted means being substituted by one or more groups selected from the group consisting of alkyl, acyl, ester, sulfonyl, sulfinyl;

$Z_1$, $Z_2$, $Z_3$, $Z_4$, $Z_5$, $Z_6$, and $Z_7$ are each independently selected from the group consisting of N, $CR_5$ and $NR_6$;

$R_5$ is independently selected from the group consisting of hydrogen, halogen, amino, cyano, hydroxyl, acyl, ester, alkyl, cycloalkyl, aryl, heteroaryl, monosubstituted or polysubstituted alkyl, monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted cycloalkyl, monosubstituted or polysubstituted aryl, and monosubstituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and hetero aryl;

$R_6$ and $R_A$ are each independently selected from the group consisting of hydrogen, acyl, ester, alkyl, cycloalkyl, aryl, heteroaryl, monosubstituted or polysubstituted alkyl, a monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted cycloalkyl, monosubstituted or polysubstituted aryl, and monosubstituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and heteroaryl.

In another preferred embodiment, A is

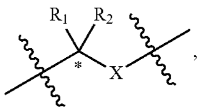

wherein * denotes a chiral center; $R_1$, $R_2$ and X are as defined above.

In another preferred embodiment, A is

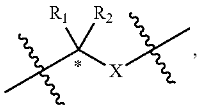

wherein * denotes R configuration, $R_1$, $R_2$ and X are as defined above.

In another preferred embodiment, X is NH or O.

In another preferred embodiment, $R_1$ and $R_2$ are each independently H, alkyl, haloalkyl or cycloalkyl.

In another preferred embodiment, C is selected from the group consisting of

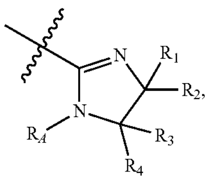

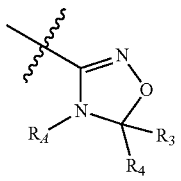

and

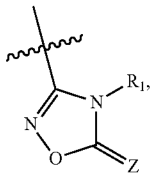

wherein

Z is O;

$R_1$, $R_2$, $R_3$, $R_4$ and $R_A$ are as defined above.

In another preferred embodiment, C is

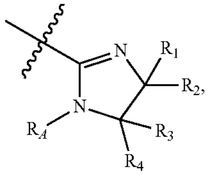

$R_1$, $R_2$, $R_3$, $R_4$ and $R_A$ are as defined above, or $R_1$ and $R_4$ fused together with the C atoms attached to them to form substituted or unsubstituted 3-7-membered cycloalkane, aza-cycloalkane, oxa-cycloalkane, or thio-cycloalkane, wherein the substituted means being substituted by one or more groups selected from the group consisting of alkyl, acyl, ester, sulfonyl and sulfinyl.

In another preferred embodiment, C is

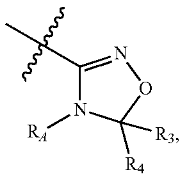

$R_3$, $R_4$ and $R_A$ are as defined above, or $R_3$ and $R_4$ fused together with the C atoms attached to them to form substituted or unsubstituted 3-7-membered cycloalkane, aza-cycloalkane, oxa-cycloalkane, or thio-cycloalkane, wherein the substituted means being substituted by one or more groups selected from the group consisting of alkyl, acyl, ester, sulfonyl and sulfinyl.

In another preferred embodiment,

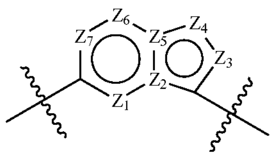

moiety is

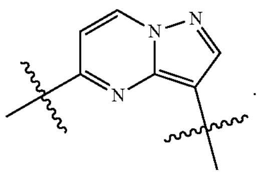 [SMILES: *c1ccn2ncc(*)c2n1]

In another preferred embodiment, the compound of formula I, or the tautomer thereof, or the mesomer thereof, the racemate thereof and the mixture of the mesomer and the racemate thereof, or the enantiomer thereof, the diastereomer thereof and the mixture of the enantiomer and the diastereomer thereof, or the pharmaceutically acceptable salt thereof, or the deuterated compound thereof:

I

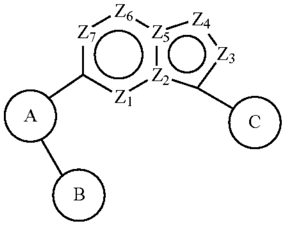;

in formula I:

A is

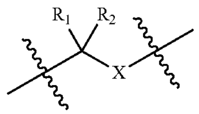, wherein, X is $NR_6$, O, $CR_1R_2$, S, S(O) or $S(O)_2$;

B is optionally selected from the group consisting of monocyclic aromatic hydrocarbon, bicyclic aromatic hydrocarbon, monocyclic heteroaromatic hydrocarbon, and bicyclic heteroaromatic hydrocarbon, wherein the H on any carbon atom of B can be substituted by the following substituents: halogen, hydroxyl, amino, cyano, ester, alkyl, haloalkyl, alkylamino, alkoxy, aryl or heteroaryl;

C is selected from

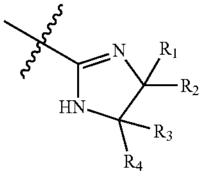 or 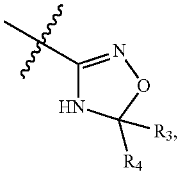

wherein the $R_1$, $R_2$, $R_3$, $R_4$ are each independently selected from the group consisting of hydrogen, halogen, amino, cyano, hydroxyl, acyl, ester, alkyl, haloalkyl, cycloalkyl, halocycloalkyl, aryl, heteroaryl, monosubstituted or polysubstituted alkyl, monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted cycloalkyl, monosubstituted or polysubstituted aryl, and monosubstituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and heteroaryl, $R_1$ and $R_2$, $R_2$ and $R_3$, $R_3$ and $R_4$ or $R_1$ and $R_4$ can be connected to form 3-7-membered cycloalkane, aza-cycloalkane, oxa-cycloalkane, or thio-cycloalkane;

$Z_1$, $Z_2$, $Z_3$, $Z_4$, $Z_5$, $Z_6$ and $Z_7$ are each independently selected from N, $CR_5$ or $NR_6$;

$R_5$ and $R_6$ are each independently selected from the group consisting of hydrogen, halogen, amino, cyano, hydroxy, acyl, ester, alkyl, cycloalkyl, haloalkyl, halocycloalkyl, aryl, heteroaryl, monosubstituted or polysubstituted alkyl, monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted cycloalkyl, monosubstituted or polysubstituted aryl, and monosubstituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and heteroaryl.

In another preferred embodiment, the compound, or the tautomer thereof, or the mesomer thereof, the racemate thereof and the mixture of the mesomer and the racemate thereof, or the enantiomer thereof, the diastereomer thereof and the mixture of the enantiomer and the diastereomer thereof, or the pharmaceutically acceptable salt thereof, or the deuterated compound thereof:

II

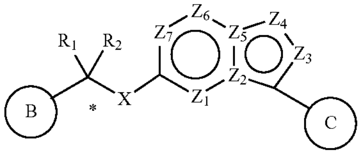

in formula II,

* denotes a chiral center;

X is selected from $NR_6$, O, $CR_1R_2$, S, S(O) or $S(O)_2$;

$R_1$ and $R_2$ are different and independently selected from the group consisting of hydrogen, halogen, amino, cyano, hydroxyl, alkyl and haloalkyl;

$R_6$ is independently selected from the group consisting of hydrogen, alkyl, and monosubstituted or polysubstituted alkyl, the substituent of the monosubstituted or polysubstituted alkyl is independently selected from the group consisting of halogen, amino, cyano, hydroxy, acyl, ester, alkyl, haloalkyl, cycloalkyl, halocycloalkyl, alkoxy, haloalkoxy, aryl and heteroaryl;

B, C, $Z_1$, $Z_2$, $Z_3$, $Z_4$, $Z_5$, $Z_6$ and $Z_7$ are as defined above.

In another preferred embodiment, all of $Z_1$, $Z_4$ and $Z_5$ are N.

In another preferred embodiment, all of $Z_2$, $Z_4$ and $Z_6$ are N.

In another preferred embodiment, all of $Z_2$, $Z_3$, $Z_4$ and $Z_6$ are N.

In another preferred embodiment, all of $Z_3$, $Z_6$ and $Z_7$ are $CR_5$, wherein, $R_5$ is independently selected from the group consisting of hydrogen, halogen, amino, cyano, hydroxyl, acyl, ester, alkyl, cycloalkyl, aryl, heteroaryl, monosubstituted or polysubstituted alkyl, monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted cycloalkyl, monosubstituted or polysubstituted aryl, and monosubstituted or polysubstituted heteroaryl are independently selected from the group consisting of halogen, amino, cyano, hydroxy, acyl, ester, alkyl, haloalkyl, cycloalkyl, halocycloalkyl, alkoxy, haloalkoxy, aryl and heteroaryl; preferably $R_5$ is H or halogen.

In another preferred embodiment, the compound, or the tautomer, or the mesomer, the racemate and the mixture of the mesomer and the racemate, or the enantiomer, the diastereomer and the mixture of enantiomer and diastereomer, or the pharmaceutically acceptable salt, or the deuterated compound thereof, wherein B is independently selected from the group consisting of

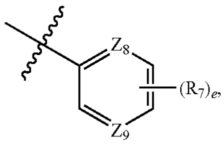 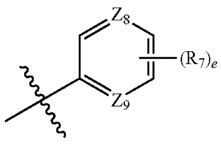 ,

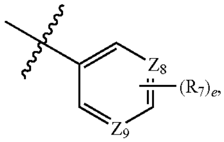 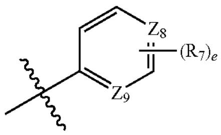 ,

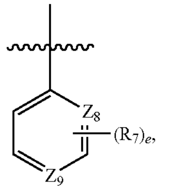 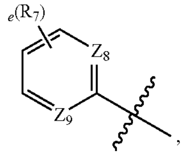 ,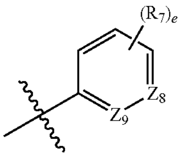 ,

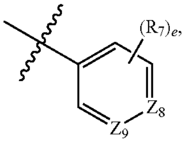 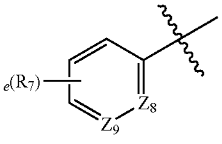 ,

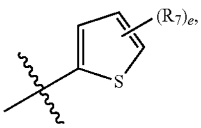 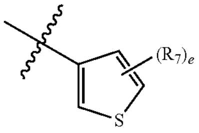 ,

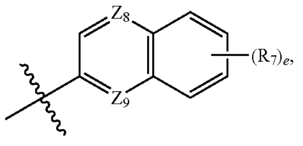

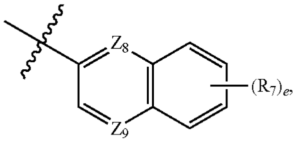 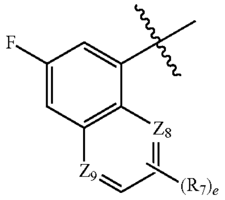 ,

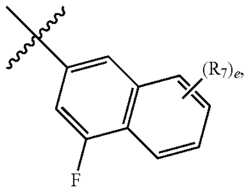 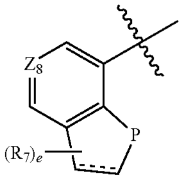 and

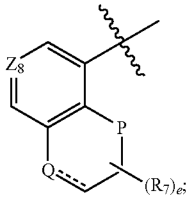

wherein, ⎓ is a single bond or a double bond;

$Z_8$ and $Z_9$ are each independently selected from $CR_{11}$ or N;

P is independently selected from 0, NH or S;

when ⎓ is a double bond, Q is independently selected from $CR_{11}$ or N; when ⎓ is a single bond, Q is independently selected from O, S, $CR_{11}R_{12}$ or NH;

$R_7$ are each independently selected from the group consisting of hydrogen, halogen, amino, cyano, hydroxy, acyl, ester, alkyl, cycloalkyl, alkoxy, aryl, heteroaryl, monosubstituted or polysubstituted alkyl, monosubstituted or polysubstituted alkoxy, monosubstituted or polysubstituted cycloalkyl, monosubstituted or polysubstituted aryl, and monosubstituted or polysubstituted heteroaryl; the substituents of the mono-substituted or polysubstituted alkyl, mono-substituted or polysubstituted alkoxy, mono-substituted or polysubstituted cycloalkyl, mono-substituted or polysubstituted aryl, and mono-substituted or polysubstituted heteroaryl are independently selected from the group consisting of deuterium, halogen, amino, cyano, hydroxy, acyl, ester, alkyl, haloalkyl, cycloalkyl, halocycloalkyl, alkoxy, haloalkoxy, aryl and heteroaryl;

$R_{11}$ and $R_{12}$ are each independently selected from the group consisting of H, hydroxy, halogen, amino, cyano, acyl, alkyl, haloalkyl, alkoxy and haloalkoxy;

e is 0, 1, 2, 3 or 4.

In another preferred embodiment, B is independently selected from the group consisting of

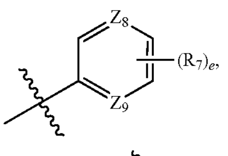 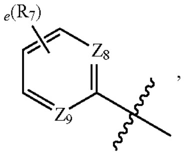 ,

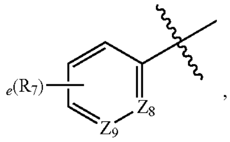 , 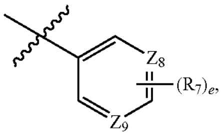

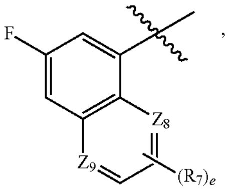 , 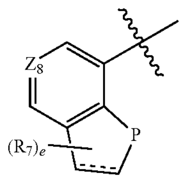 and

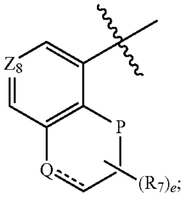

wherein $Z_8$ and $Z_9$ are each independently selected from $CR_{11}$ or N;

$R_7$ is each independently selected from the group consisting of hydrogen atom, halogen, amino, cyano, hydroxy, acyl, ester, alkyl, cycloalkyl, alkoxy, aryl, heteroaryl, monosubstituted or polysubstituted alkyl, monosubstituted or polysubstituted alkoxy, monosubstituted or polysubstituted cycloalkyl, monosubstituted or polysubstituted aryl, and monosubstituted or polysubstituted heteroaryl; the substituents of the mono-substituted or polysubstituted alkyl, mono-substituted or polysubstituted alkoxy, mono-substituted or polysubstituted cycloalkyl, mono-substituted or polysubstituted aryl, and mono-substituted or polysubstituted heteroaryl are independently selected from deuterium, halogen, amino, cyano, hydroxy, acyl, ester, alkyl, haloalkyl, cycloalkyl, halocycloalkyl, alkoxy, haloalkoxy, aryl and heteroaryl;

$R_{11}$ is each independently selected from the group consisting of H, hydroxy, halogen, amino, cyano, acyl, alkyl, haloalkyl, alkoxy and haloalkoxy;

e is 0, 1 or 2;

P, Q and ⎓ are as defined above.

In another preferred embodiment, B is independently

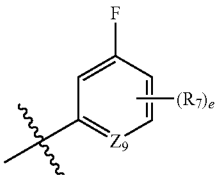

or

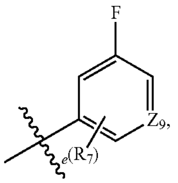

wherein $Z_9$ is $CR_{11}$ or N;

each $R_7$ is independently selected from the group consisting of hydrogen, halogen, amino, cyano, hydroxy, acyl, ester, alkyl, cycloalkyl, alkoxy, aryl, heteroaryl, mono-substituted or polysubstituted alkyl, monosubstituted or polysubstituted alkoxy, monosubstituted or polysubstituted cycloalkyl, monosubstituted or polysubstituted aryl, and monosubstituted or polysubstituted heteroaryl; the substituents of the monosubstituted or polysubstituted alkyl, monosubstituted or polysubstituted alkoxy, monosubstituted or polysubstituted cycloalkyl, monosubstituted or polysubstituted aryl, and monosubstituted or polysubstituted heteroaryl are independently selected from the group consisting of deuterium, halogen, amino, cyano, hydroxyl, acyl, ester, alkyl, haloalkyl, cycloalkyl, halocycloalkyl, alkoxy, haloalkoxy, aryl and heteroaryl;

each $R_{11}$ is independently selected from the group consisting of H, hydroxy, halogen, amino, cyano, acyl, alkyl, haloalkyl, alkoxy and haloalkoxy;

e is 0, 1 or 2.

In another preferred embodiment, the compound, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof, wherein C is

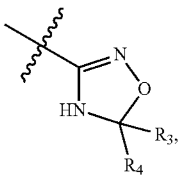

wherein, $R_3$ and $R_4$ are as defined above.

In another preferred embodiment, $R_3$ and $R_4$ are each independently selected from the group consisting of hydrogen, halogen, amino, cyano, hydroxyl, acyl, ester, alkyl, haloalkyl, cycloalkyl, halocycloalkyl, monosubstituted or polysubstituted alkyl, and monosubstituted or polysubstituted cycloalkyl; the substituents of the monosubstituted or polysubstituted alkyl and monosubstituted or polysubstituted cycloalkyl is independently selected from the group consisting of halogen, amino, cyano, hydroxy, acyl, ester, alkyl, haloalkyl, cycloalkyl, halocycloalkyl, alkoxy and haloalkoxy.

In another preferred embodiment, $R_3$ and $R_4$ together with the C atom attached to them form substituted or unsubstituted 3-7-membered cycloalkane, aza-cycloalkane, oxa-cycloalkane or oxo (=O); wherein the substituted means being substituted by one or more groups selected from the group consisting of alkyl, acyl, ester, sulfonyl and sulfinyl.

In another preferred embodiment, the compound represented by formula I, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof have one or more characteristics selected from the group consisting of:

A is

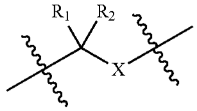

, wherein X is NH or O; $R_1$ and $R_2$ are each independently H, alkyl or haloalkyl;

B is independently

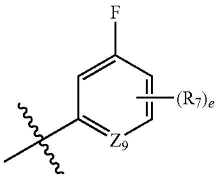

or

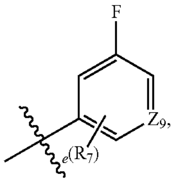

wherein, $Z_9$ is $CR_{11}$ or N;

each $R_7$ is independently selected from the group consisting of hydrogen, halogen, hydroxyl, acyl, alkyl, cycloalkyl, alkoxy, monosubstituted or polysubstituted alkyl, and monosubstituted or polysubstituted alkoxy; optionally, the substituent of the monosubstituted or polysubstituted alkyl and monosubstituted or polysubstituted alkoxy is independently selected from the group consisting of deuterium, halogen, amino, cyano, hydroxy, alkyl, haloalkyl, cycloalkyl, halocycloalkyl, alkoxy and haloalkoxy;

each $R_{11}$ is independently selected from the group consisting of H, hydroxyl, halogen, alkyl, haloalkyl, alkoxy and haloalkoxy;

e is 0, 1 or 2;

C is independently

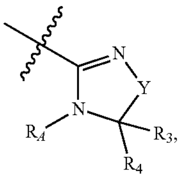

preferably C is

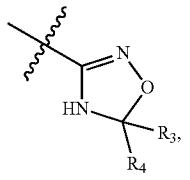

wherein Y is selected from the group consisting of O and $CR_1R_2$; $R_3$ and $R_4$ are each independently selected from the group consisting of H, alkyl, monosubstituted or polysubstituted alkyl, phenyl, pyridyl, monosubstituted or polysubstituted phenyl, and monosubstituted or polysubstituted pyridyl; or $R_3$ and $R_4$ together with the C atom attached to them form a substituted or unsubstituted 3-8-membered cycloalkyl or heterocyclyl, the substituted means being substituted by one or more groups selected from the group consisting of halogen, alkoxy, ester and sulfonyl;

$Z_1$, $Z_2$, $Z_3$, $Z_4$, $Z_5$, $Z_6$ and $Z_7$ are each independently N or $CR_5$, wherein, $R_5$ is selected from the group consisting of H and halogen.

In another preferred embodiment, the compound of formula I, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof having the structure shown in formula III,

III

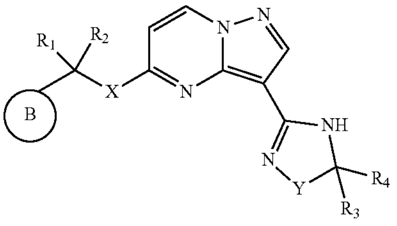

wherein,

B, X, Y, $R_1$, $R_2$, $R_3$ and $R_4$ are as defined above.

In another preferred embodiment, A, B, C, $Z_1$, $Z_2$, $Z_3$, $Z_4$, $Z_5$, $Z_6$ and $Z_7$ are the specific group corresponding to each specific compound in the example.

In another preferred embodiment, the compound, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof, wherein the compound represented by formula I is optionally selected from the following compounds:

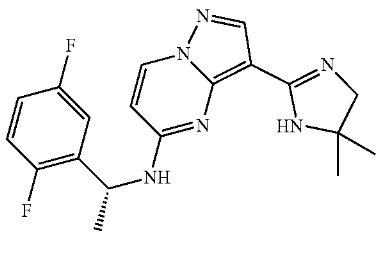

-continued

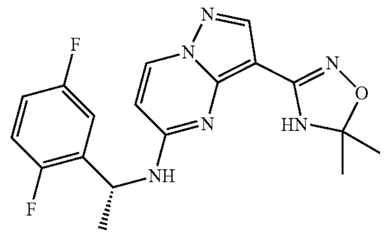

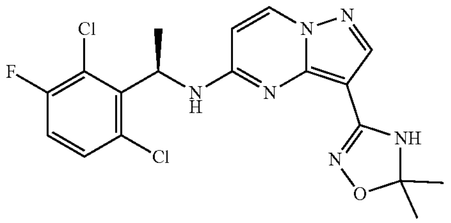

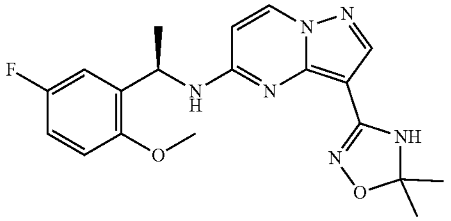

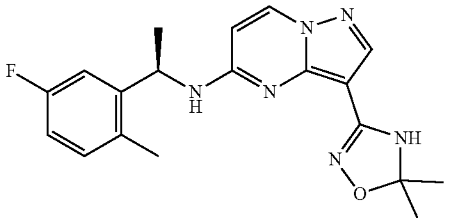

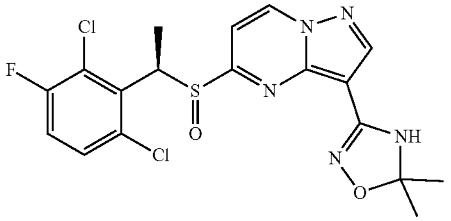

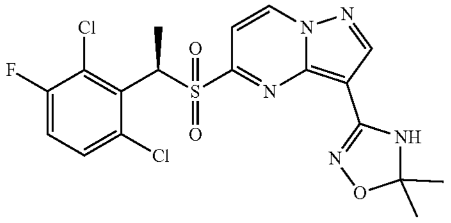

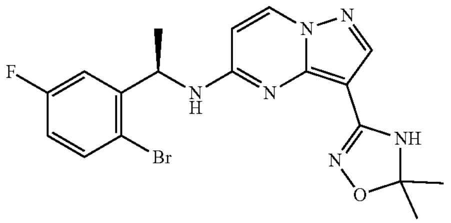

-continued
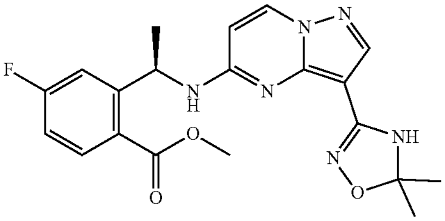
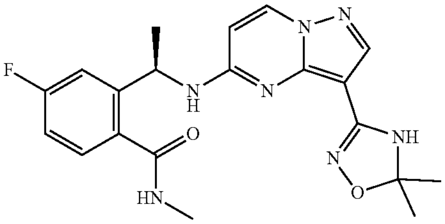
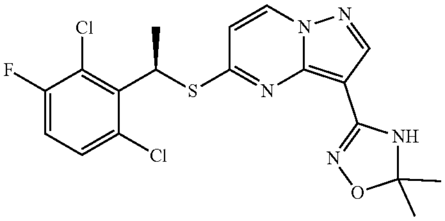
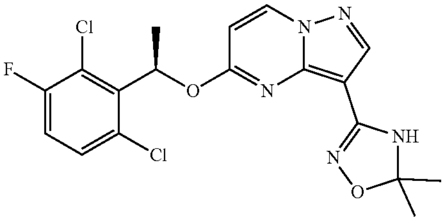
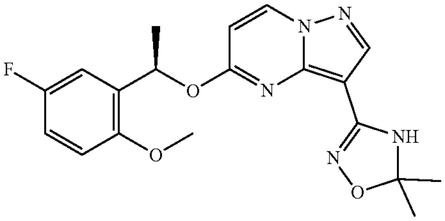
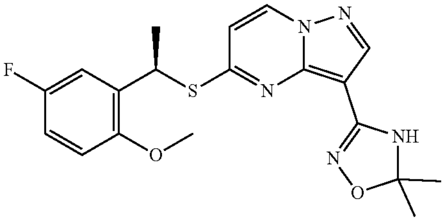
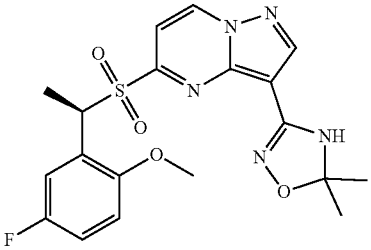
-continued
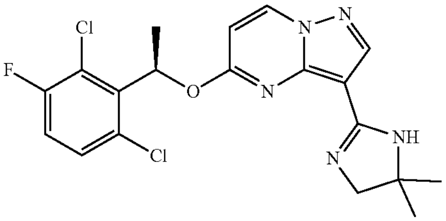
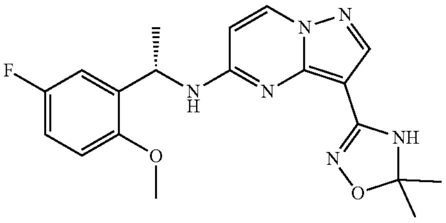
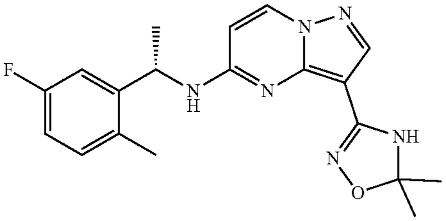
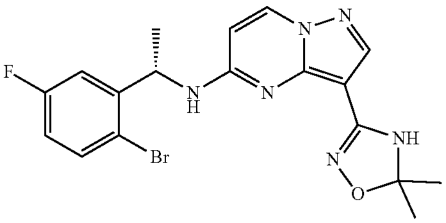
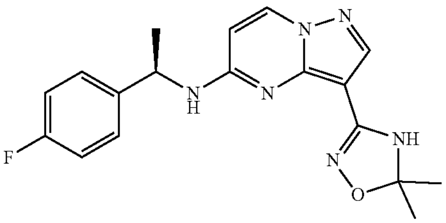
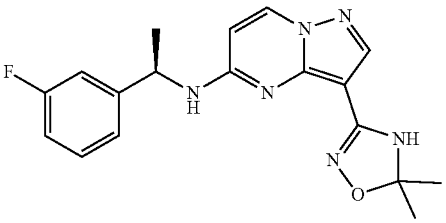
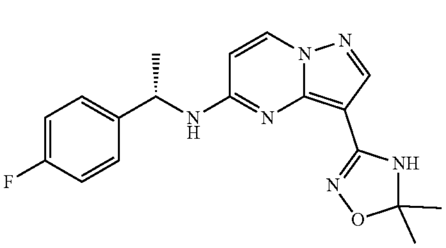

-continued
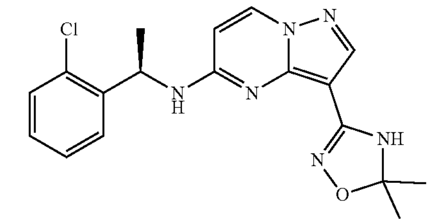
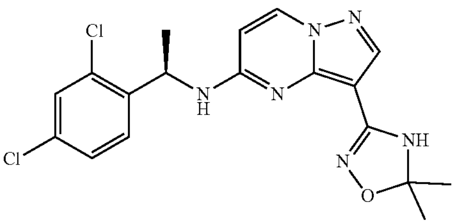
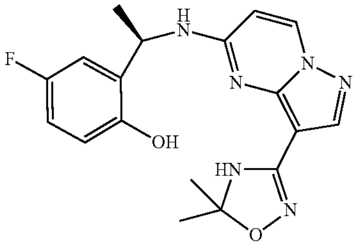
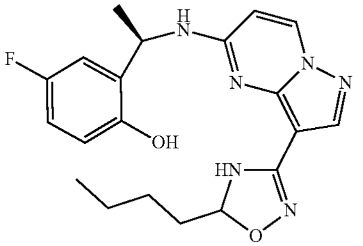
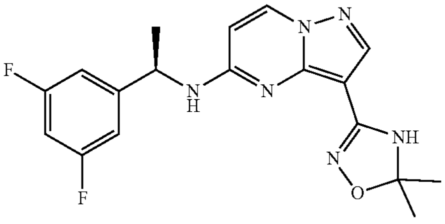
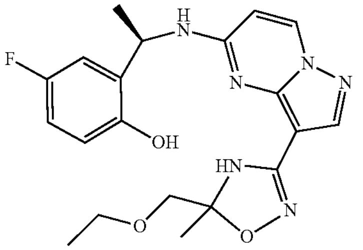
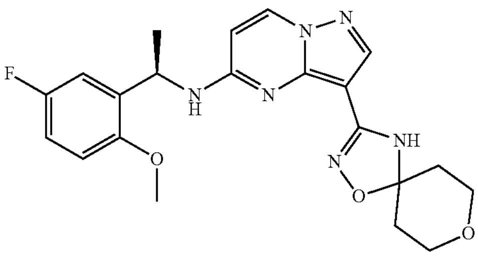
-continued
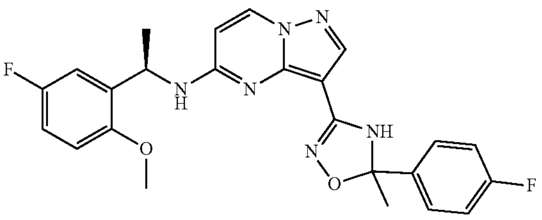
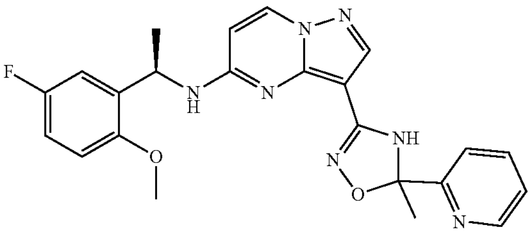
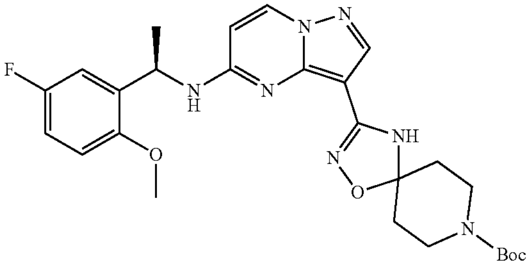
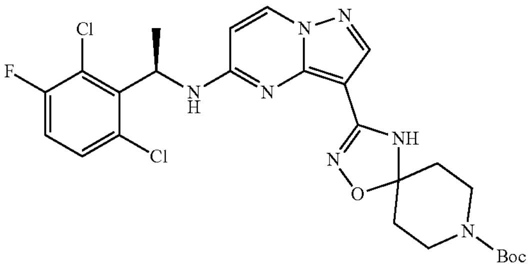
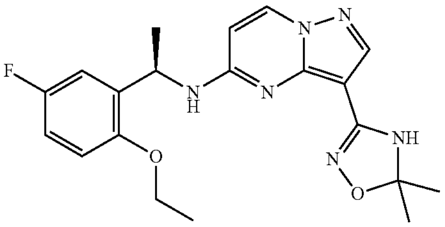
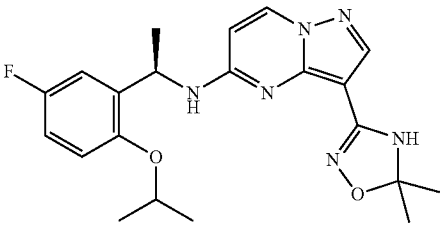
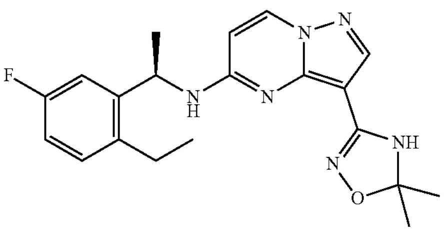

-continued
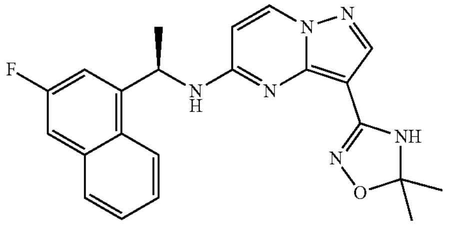
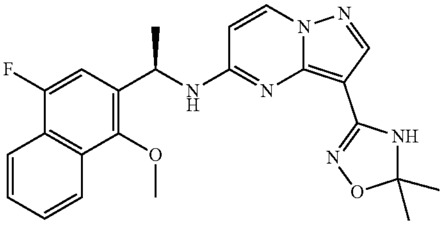
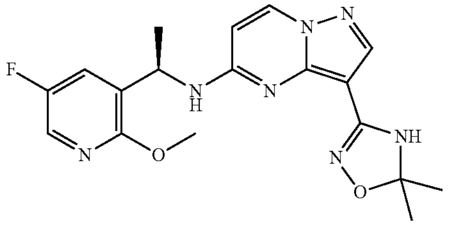
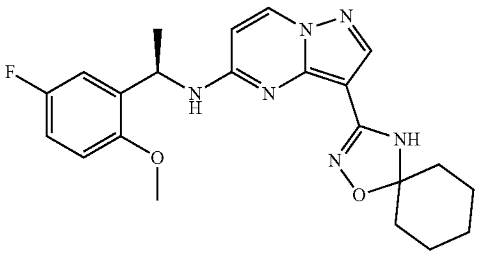
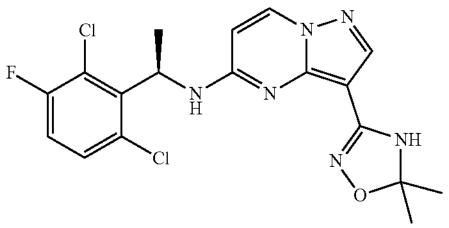
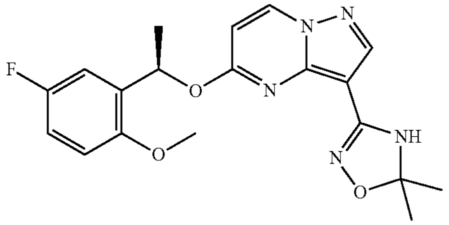
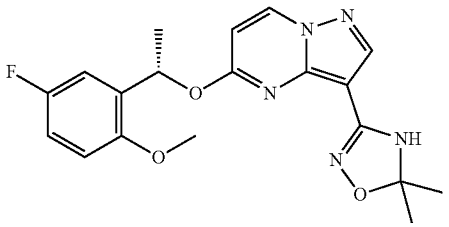
-continued
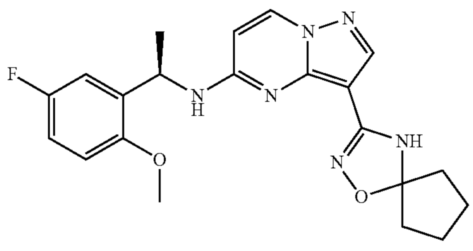
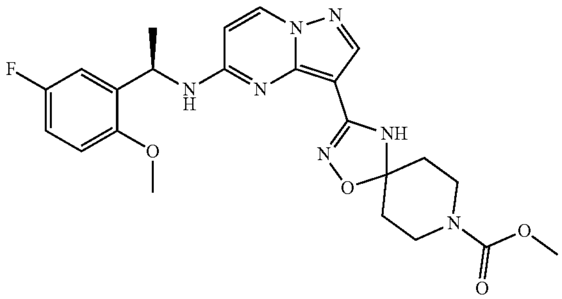
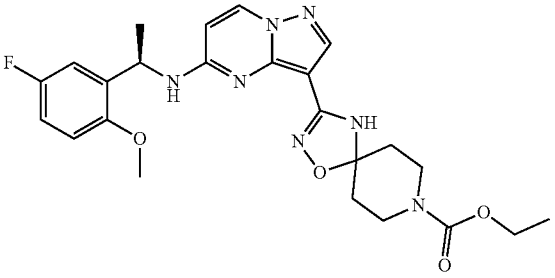
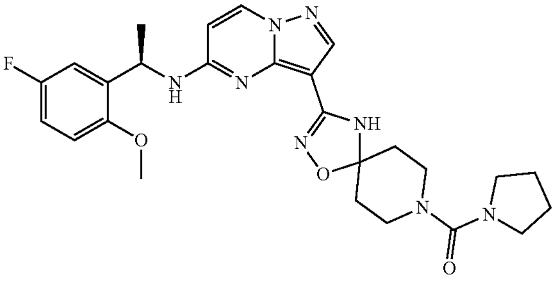
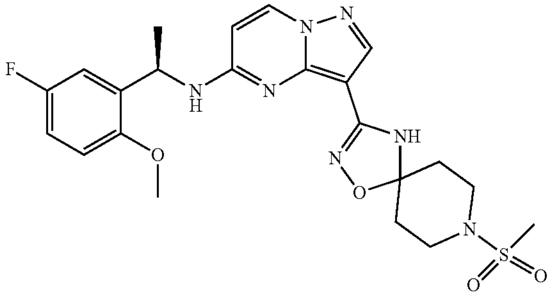
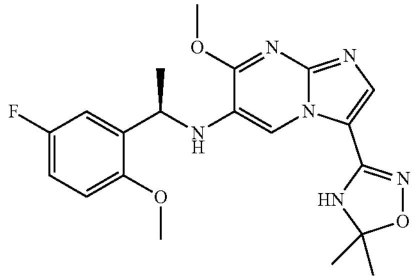

-continued
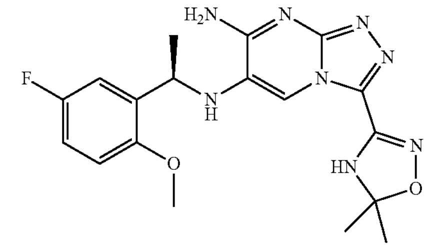
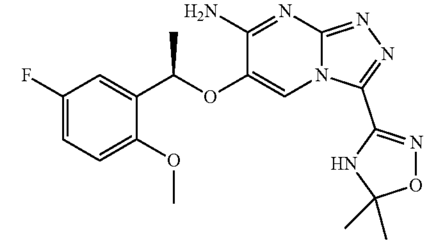
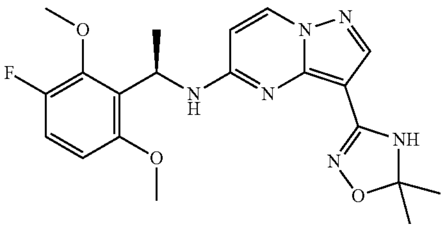
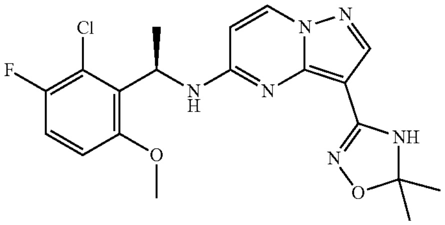
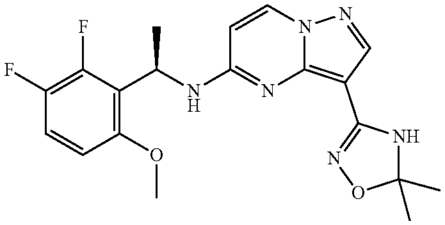
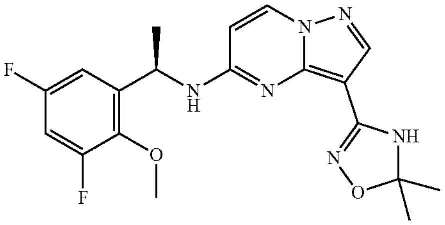
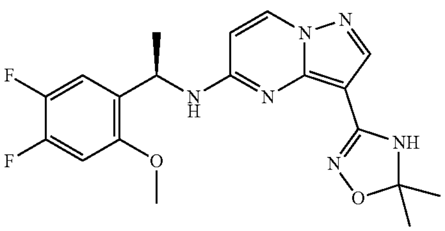
-continued
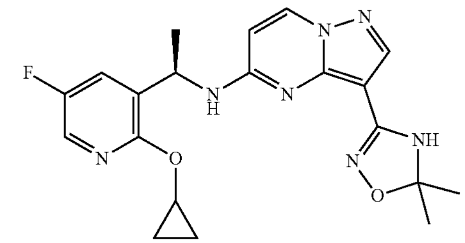
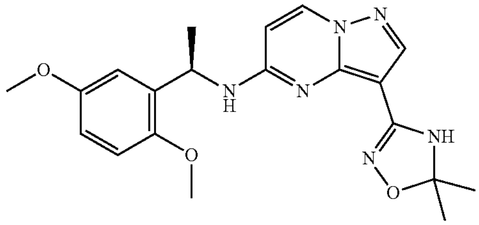
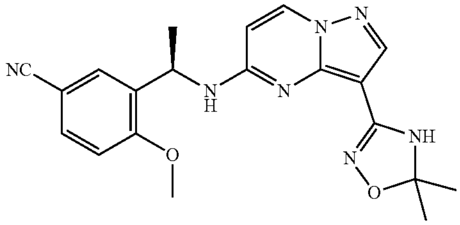
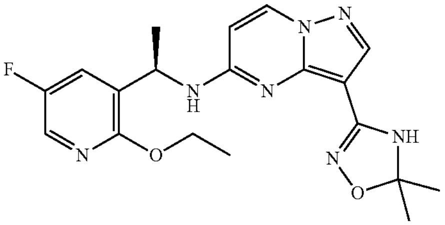
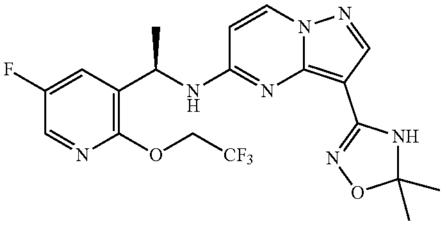
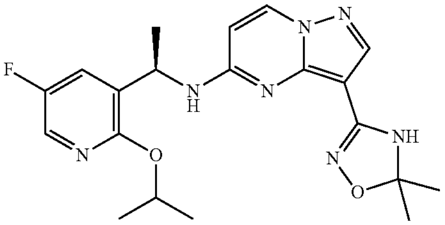
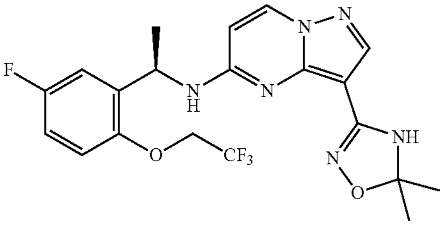

-continued
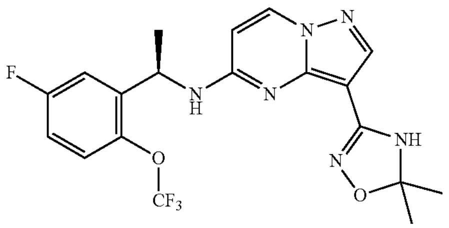
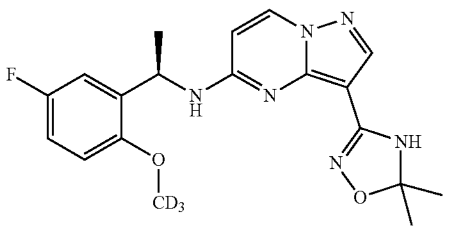
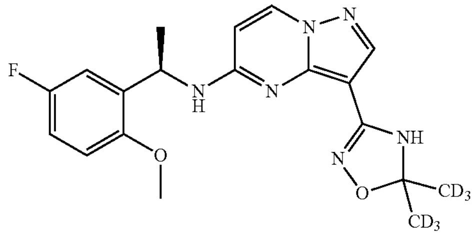
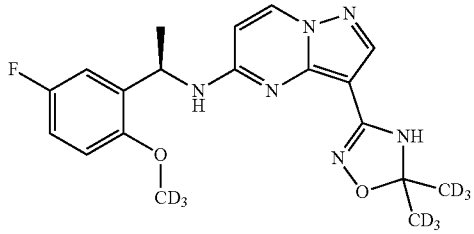
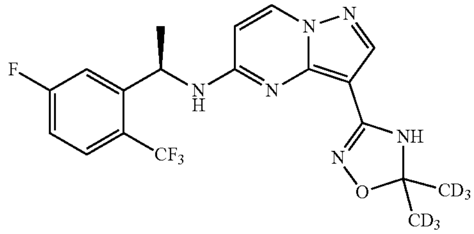
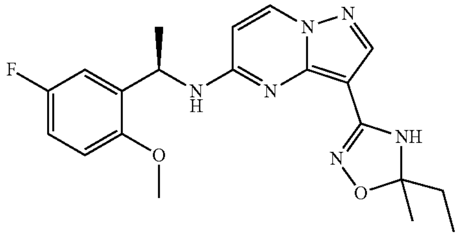
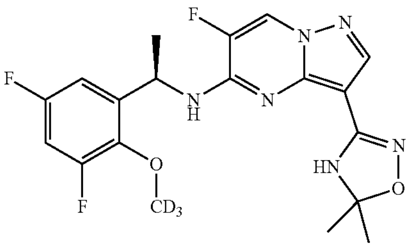
-continued
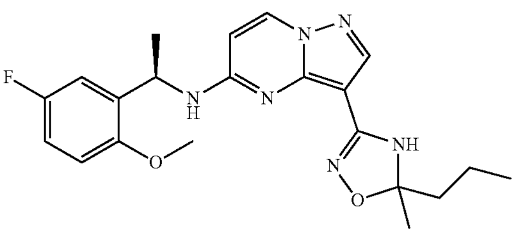
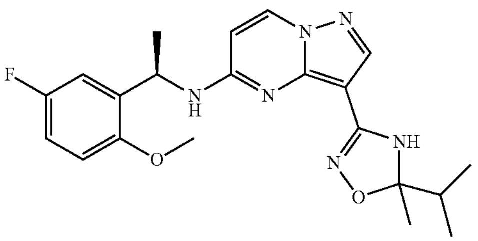
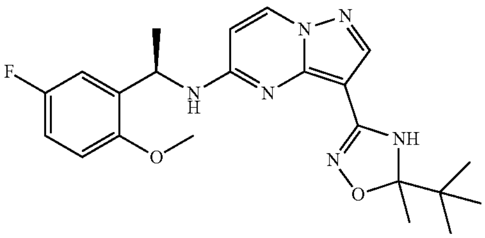
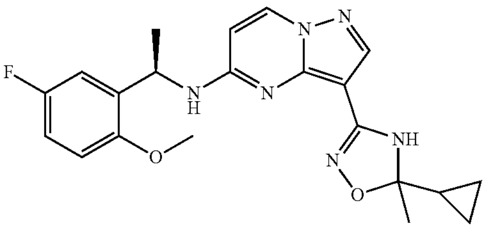
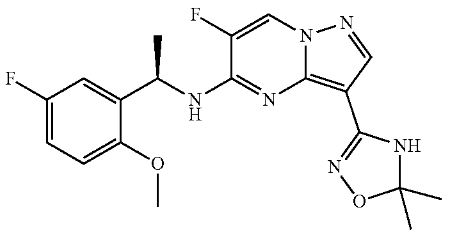
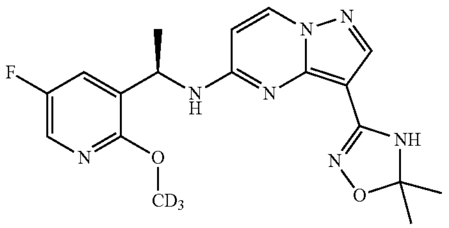
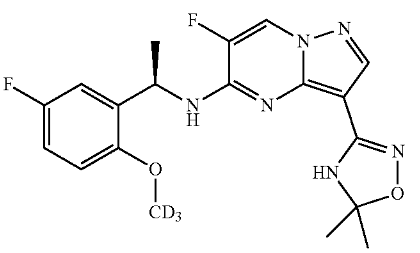

-continued
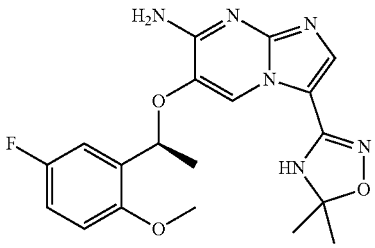
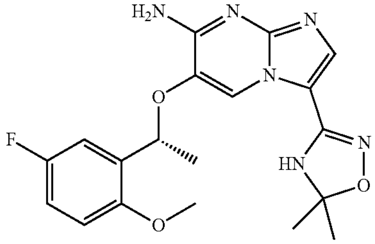
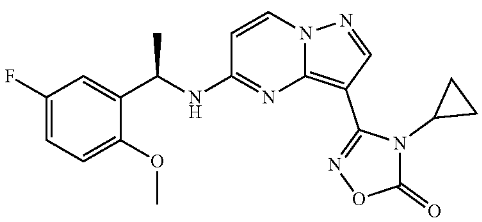
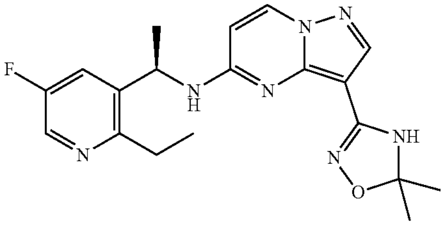
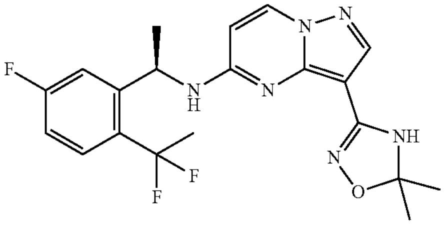
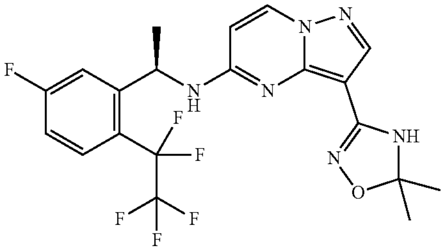
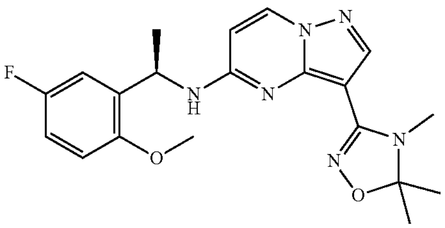
-continued
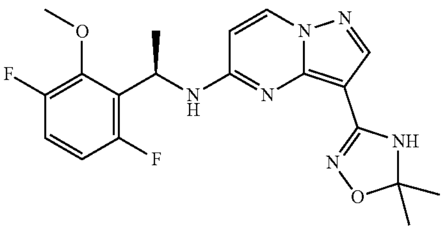
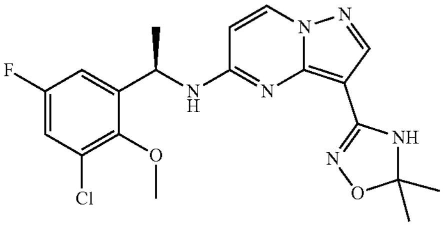
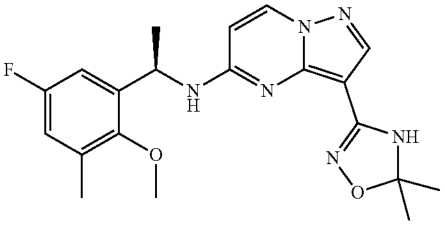
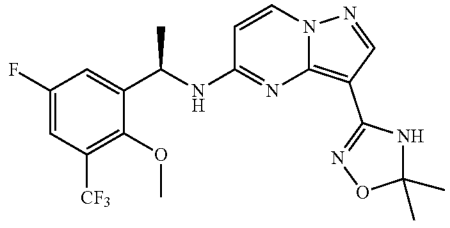
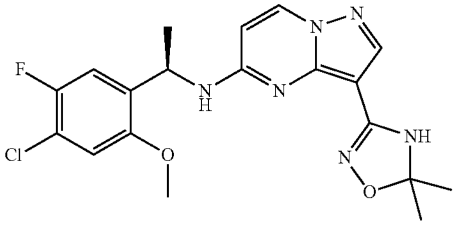
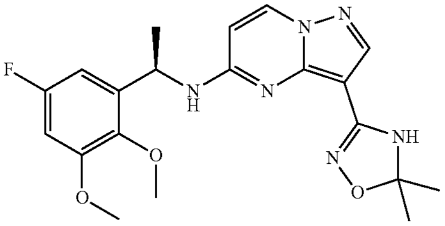
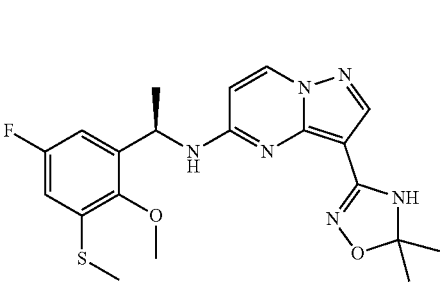

-continued
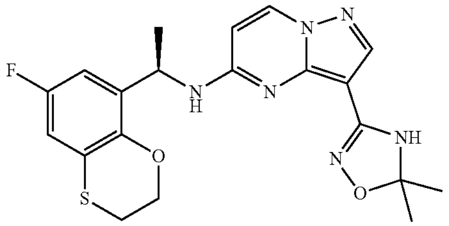
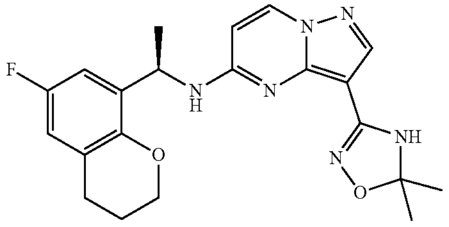
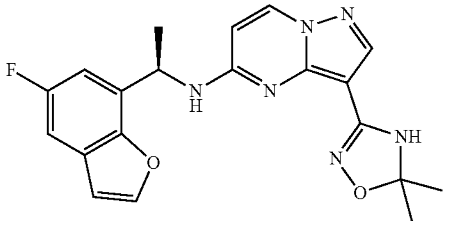
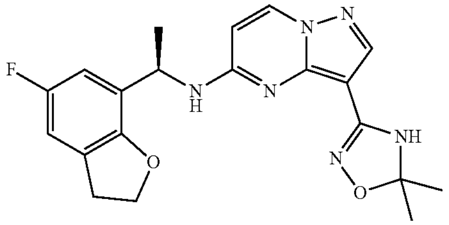
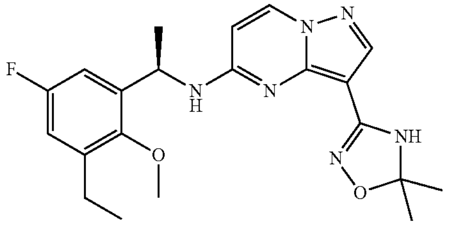
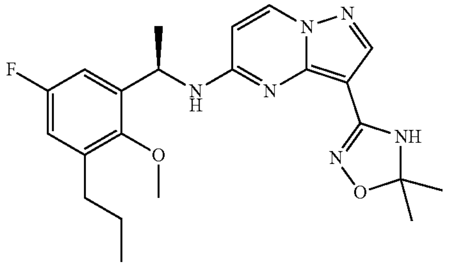
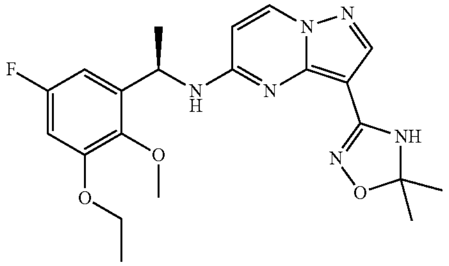
-continued
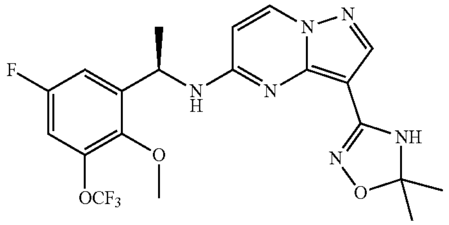
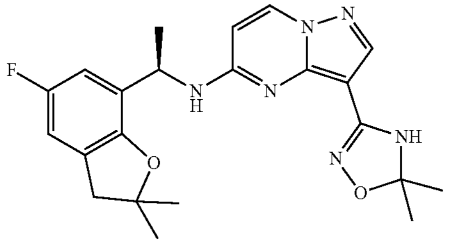
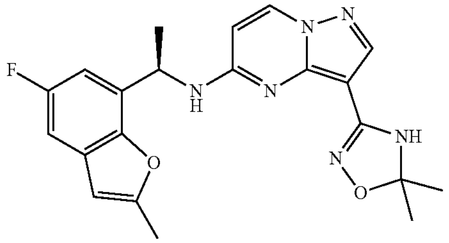
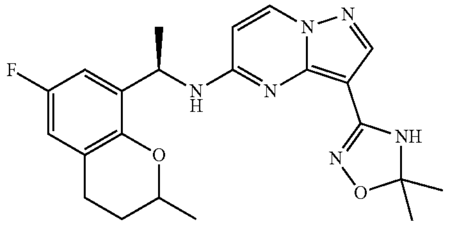
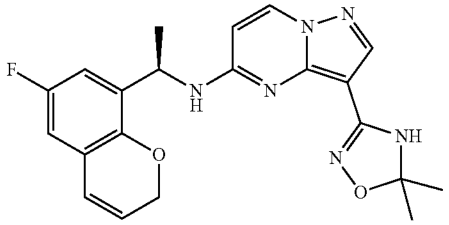
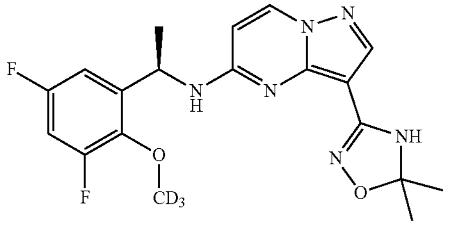
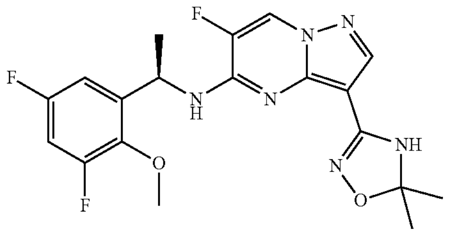

-continued
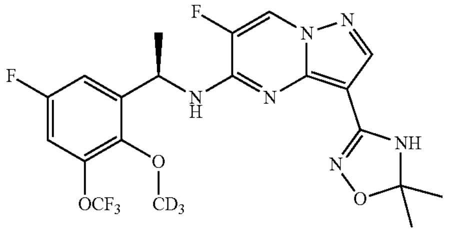
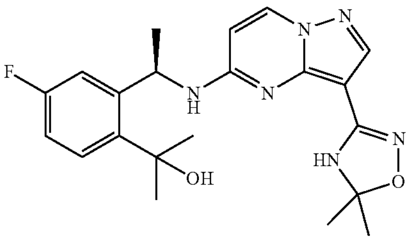
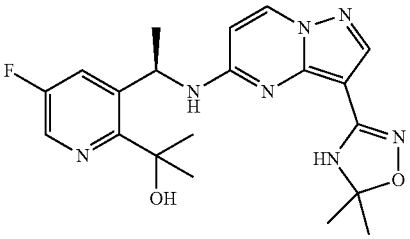
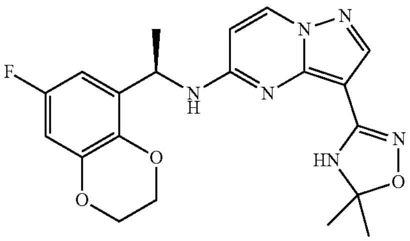
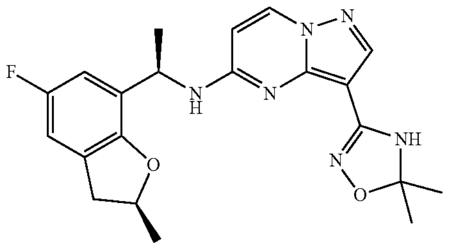
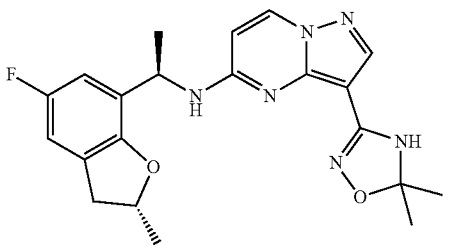
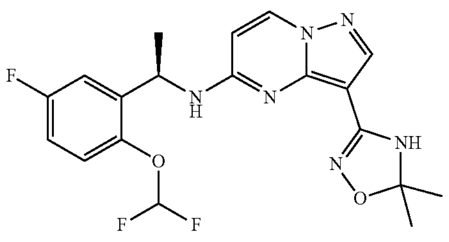
-continued
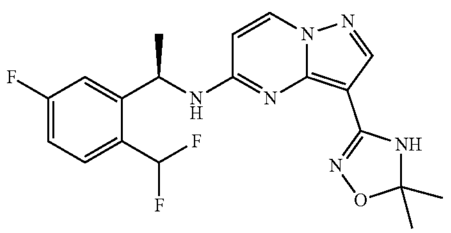
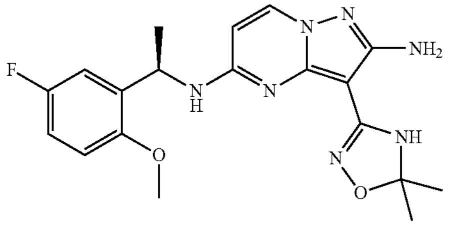
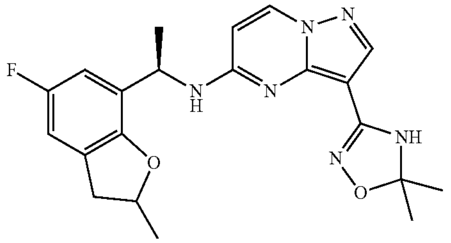
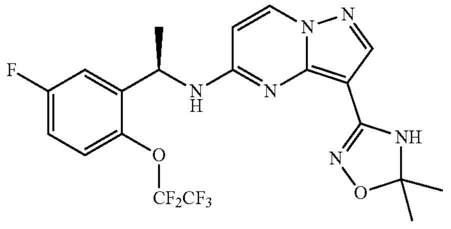
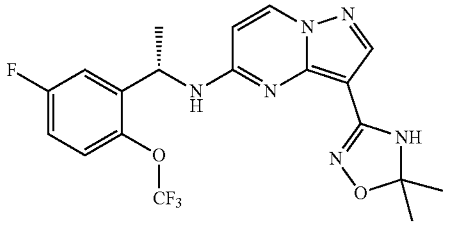
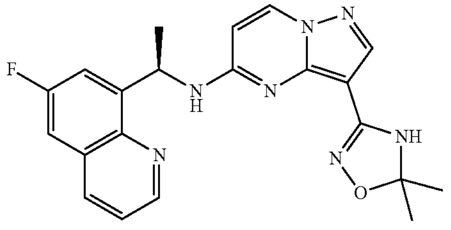
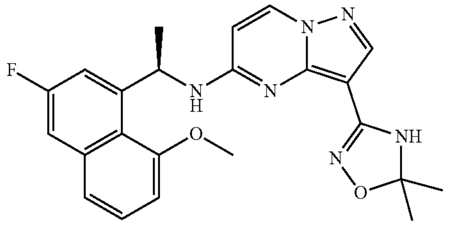

-continued
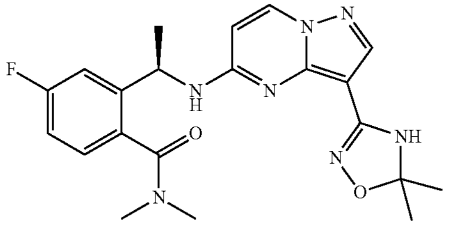
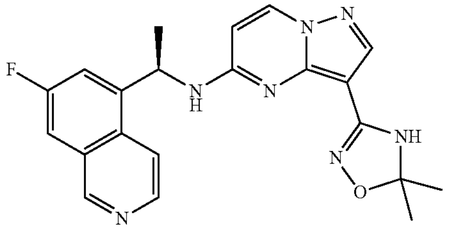
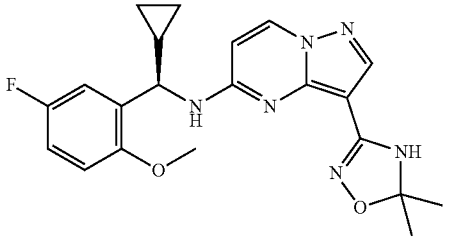
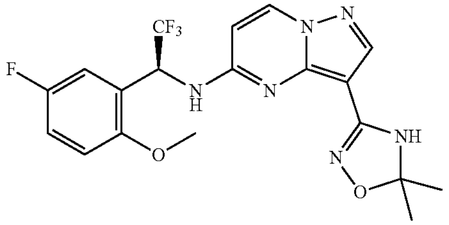
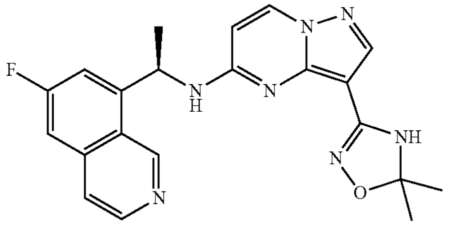
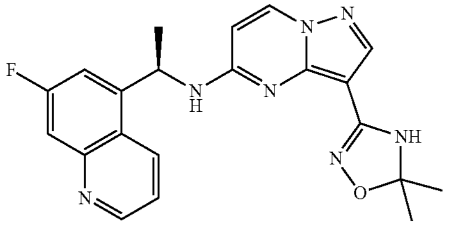
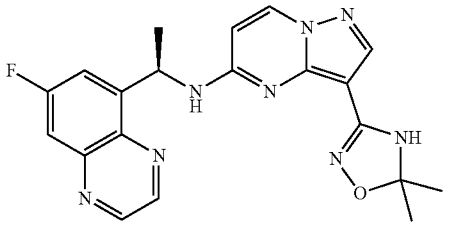
-continued
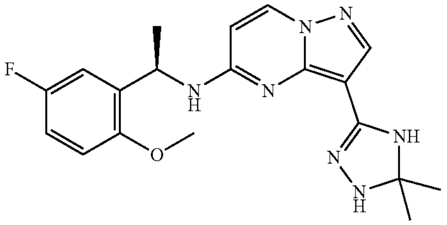
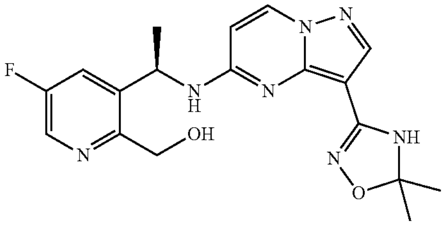
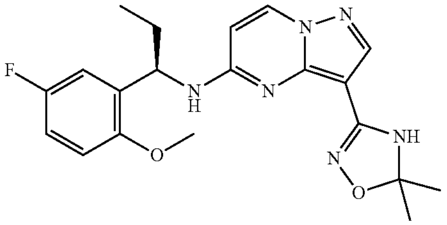
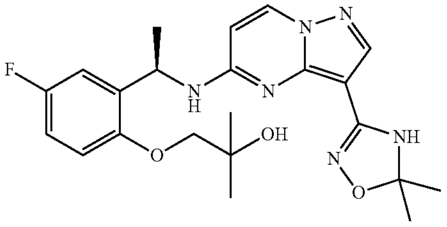
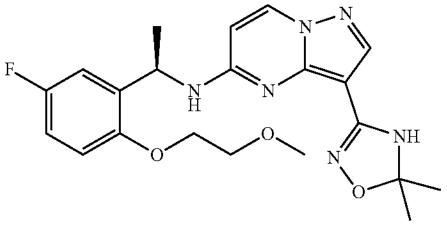
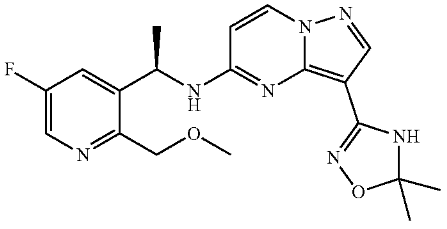
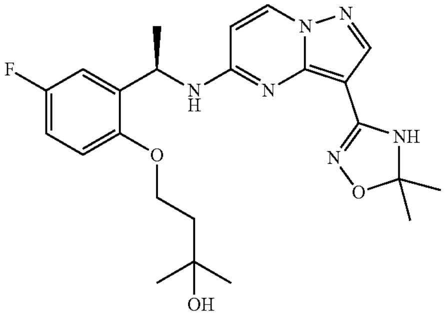

-continued
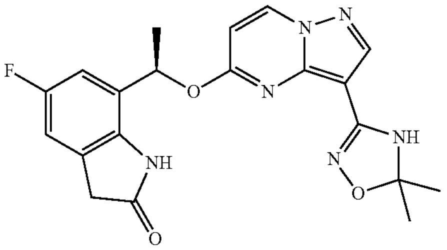
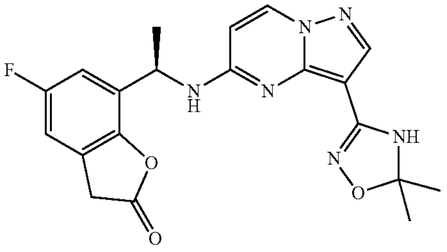
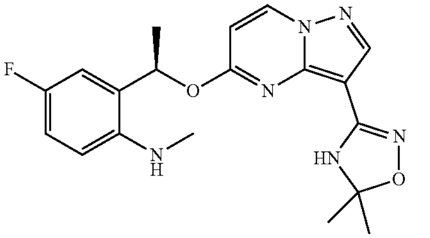
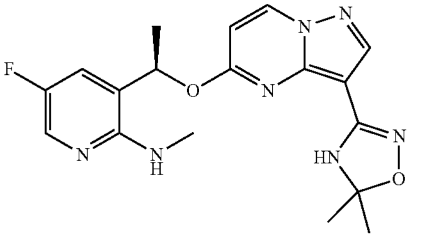
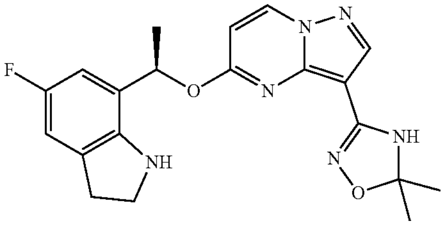
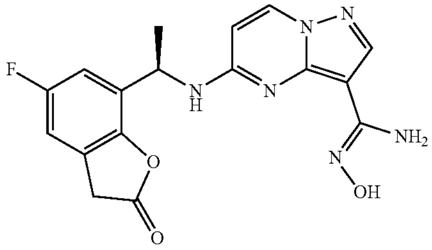
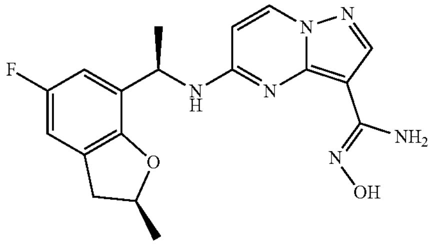
-continued
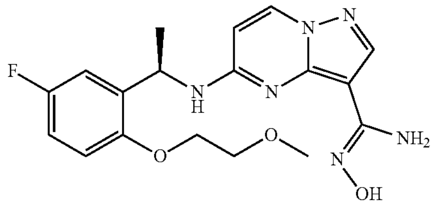
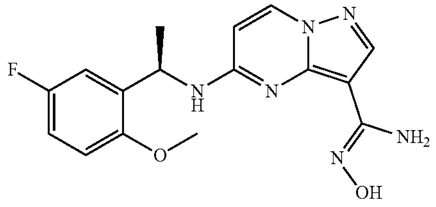
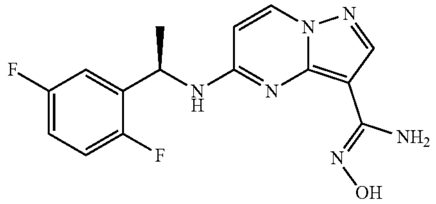
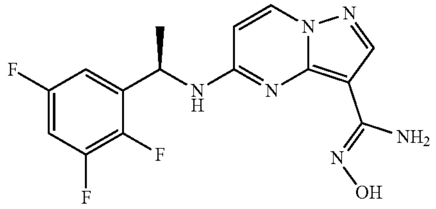
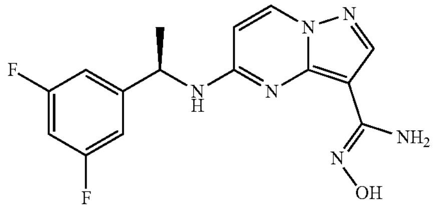
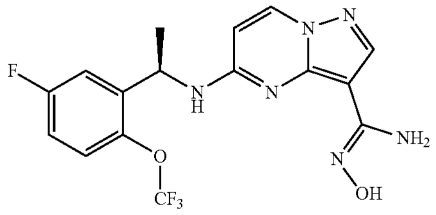
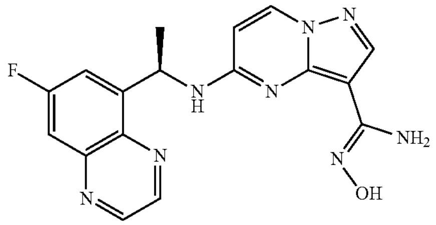
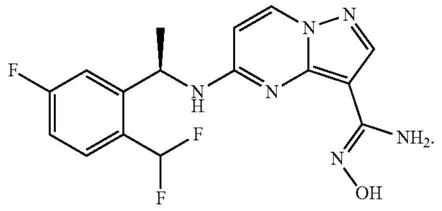

In another preferred embodiment, the compound represented by formula I is selected from the compound shown in the example of the present invention.

In the second aspect of the invention, a pharmaceutically acceptable salt of the compound of formula I is provided, wherein the pharmaceutically acceptable salt is an inorganic acid salt or an organic acid salt, wherein the inorganic acid salt is selected from the group consisting of hydrochloride, hydrobromide, hydroiodate, sulfate, bisulfate, nitrate, phosphate and acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, hydroxyethanesulfonate, benzenesulfonate, salicylate, picrate, glutamate, ascorbate, camphorate, camphor sulfonate.

In the third aspect of the invention, a pharmaceutical composition comprising a therapeutically effective amount of the compound of the first aspect, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof, and one or more pharmaceutically acceptable carriers, diluents or excipients is provided.

In the fourth aspect of the invention, a use of the compound of the first aspect, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof or the pharmaceutical composition comprising the compound represented by formula I in the preparation of a medicament for preventing and/or treating the diseases related to pathological characteristics mediated by ROS1, NTRK, and ALK, etc is provided.

In another preferred embodiment, the diseases related to pathological characteristics mediated by ROS1, NTRK, and ALK, etc. include cancer, sarcoma and pain.

In another preferred embodiment, the cancer is any one of breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tumor, peritoneal tumor, melanoma, glioma, glioblastoma, head and neck cancer, mastoid nephroma, leukemia, lymphoma, myeloma and thyroid tumor.

The pharmaceutical composition provided by the invention can be made into a suitable dosage form for application. These dosage forms include those suitable for oral, rectal, topical, intraoral, and other non-parenteral administration (for example, subcutaneous, intramuscular and intravenous, etc.)

The pharmaceutical composition of the present invention can be formulated, quantified and administered in a manner consistent with medical practice specifications. The "effective amount" of the compound to be administered depends on factors such as the specific condition to be treated, the individual to be treated, the cause of the condition, the target of the drug and the manner of administration.

DETAILED DESCRIPTION OF THE INVENTION

After extensive and in-depth research, the inventor of the present invention accidentally discovered a new compound having excellent inhibitory activity against ROS1, NTRK and ALK and their drug-resistant mutations, especially against drug-resistant mutations, and having better pharmacodynamics and pharmacokinetic properties and lower toxic and side effects. It has the potential to be developed into an effective drug for drug-resistant patients that is urgently needed in clinical practice.

Term

Unless otherwise stated, the following terms used in this application (including the specification and claims) have the definitions given below.

"Alkyl" refers to a monovalent linear or branched saturated hydrocarbon group containing 1 to 12 carbon atoms composed only of carbon and hydrogen atoms. "Alkyl" is preferably an alkyl of 1 to 6 carbon atoms, that is, a $C_1$-$C_6$ alkyl, more preferably a $C_1$-$C_4$ alkyl. Examples of alkyl include but are not limited to methyl, ethyl, propyl, isopropyl, isobutyl, sec-butyl, tert-butyl, amyl, n-hexyl, octyl and dodecyl etc. In the present invention, the alkyl is also intended to include a deuterated alkyl, examples of which include, but are not limited to $CD_3$, $CD_2CD_3$ and $CD_2CD_2CD_3$.

"Alkoxy" refers to the formula —OR or —R'—OR, wherein R is an alkyl as defined herein, and R' is an alkylene. Examples of alkoxy include but are not limited to methoxy, ethoxy, isopropoxy, tert-butoxy, $-CH_2O-CH_3$, $-CH_2CH_2-O-CH_3$, $-CH_2-O-CH_2CH_3$ and the like.

"Halogen (Halo)" refers to fluorine, chlorine, bromine or iodine substituent.

"Haloalkyl" refers to an alkyl as defined herein in which one or more hydrogen is replaced by the same or different halogens. The "haloalkyl" is preferably a halogenated $C_1$-$C_6$ alkyl, more preferably a halogenated $C_1$-$C_4$ alkyl. Examples of the halogenated alkyl include $-CH_2C_1$, $-CH_2CF_3$, $-CH_2CCl_3$ and perfluoroalkyl (e.g., $-CF_3-$, $-CF_2CF_3$), etc.

"Haloalkoxy" refers to the formula —OR, wherein, R is a halogenated alkyl as defined herein. Examples of haloalkoxy include but are not limited to trifluoromethoxy, difluoromethoxy, and 2, 2, 2-trifluoroethoxy, etc.

"Cycloalkyl" refers to a monovalent saturated carbocyclic group consisting of a mono- or bicyclic ring having 3-12 ($C_3$-$C_{12}$), preferably 3-10 ($C_3$-$C_{10}$), more preferably 3-6 ring atoms ($C_3$-$C_6$). The cycloalkyl may optionally be substituted with one or more substituents, wherein each substituent is independently a hydroxyl, alkyl, alkoxy, halogen, haloalkyl, amino, monoalkylamino or dialkylamino. Examples of cycloalkyl include but are not limited to cyclopropyl, cyclobutyl, cyclopentyl, cyclohexyl and cycloheptyl, etc.

"Cycloalkoxy" refers to the formula —OR, wherein R is a cycloalkyl as defined herein. Examples of cycloalkyloxy include cyclopropyloxy, cyclobutyloxy, cyclopentyloxy and cyclohexyloxy, etc.

"Acyl" refers to the formula —C(O)R, wherein R is an alkyl or alkylamino as defined herein. "Acyl" is preferably $-C(O)C_1$-$C_6$ alkyl, $-C(O)NH_2$, $-C(O)NHC_1$-$C_6$ alkyl, $-C(O)N(C_1$-$C_6$ alkyl$)_2$, more preferably $-C(O)C_1$-$C_3$ alkyl, $-C(O)NH_2$, $-C(O)NHC_1$-$C_3$ alkyl, $-C(O)N(C_1$-$C_3$ alkyl$)_2$, examples of acyl include acetyl, n-propionyl, isopropionyl, n-butyryl, isobutyryl, tert-butyryl, $-C(O)NH_2$, $-C(O)NHCH_3$ and $-C(O)N(CH)_3)_2$, etc.

"Alkylamino" refers to the formula —NRaRb, wherein Ra and Rb are the same or different, and is each independently H or alkyl as defined herein.

Ester refers to the formula —C(O)OR, wherein R is an alkyl as defined herein. The ester is preferably $-C(O)OC_1$-

$C_6$ alkyl, more preferably —$C(O)OC_1$-$C_4$ alkyl, examples of ester include —C(O)OMe, —C(O)OEt and —C(O)O—C$(CH_3)_3$, etc.

Sulfonyl refers to formula —$S(O)_2$—R, wherein R is an alkyl as defined herein. The sulfonyl is preferably —$S(O)_2$—$C_1$-$C_6$ alkyl, examplarily comprises —$S(O)_2$-Me and —$S(O)_2$-Et, etc.

Sulfinyl refers to the formula —SO—R, wherein R is an alkyl as defined herein. The sulfinyl is preferably —SO—$C_1$-$C_6$ alkyl, examplarily comprises —SO-Me and —SO-Et, etc.

"Alkylthio" refers to the formula —SRa, wherein Ra is H or alkyl as defined herein.

"Cycloalkylamino" refers to the formula —NRaRb, wherein Ra is H, an alkyl as defined herein or a cycloalkyl as defined herein, and Rb is a cycloalkyl as defined herein; or Ra and Rb together with the N atoms attached to them form a 3-6-membered N-containing heterocyclic group, such as tetrahydropyrrolyl.

"Heterocyclyl" refers to a completely saturated or partially unsaturated cyclic group (including but not limited to, for example, 3-7-membered monocyclic, 6-11-membered bicyclic, or 8-16-membered tricyclic system) in which at least one heteroatom is present in a ring having at least one carbon atom. Each heteroatom-containing heterocyclic ring has 1, 2, 3, or 4 heteroatoms selected from the group consisting of nitrogen, oxygen, or sulfur atoms, wherein the nitrogen or sulfur atoms may be oxidized or the nitrogen atoms may be quaternized. Heterocycloalkyl refer to completely saturated heterocyclyl. Heterocyclyl can be attached to the residue of any heteroatom or carbon atom of the ring or ring molecule. Typical monocyclic heterocyclyls include, but are not limited to azetidinyl, pyrrolidyl, oxetanyl, pyrazolinyl, imidazolinyl, imidazolidinyl, oxazolidinyl, isoxazolidinyl, thiazolidinyl, isothiazolidinyl, tetrahydrofuryl, piperidyl, piperazinyl, 2-oxoppiperazinyl, 2-oxo piperidyl, 2-oxopyrrolidyl, hexahydroazepinyl, 4-piperidone, tetrahydropyranyl, morpholinyl, thiomorpholinyl, thiomorpholinylsulfoxide, thiomorpholinylsulfone, 1,3-dioxane and tetrahydro-1,1-dioxythienyl, etc. A polycyclic heterocyclyl includes spiro, fused, and bridged heterocyclyls. The spiro, fused, and bridged heterocyclyls involved are optionally connected with other groups by single bond, or are further fused with other cycloalkyl, heterocyclyl, aryl and heteroaryl by any two or more atoms of the ring.

"Aryl" refers to aromatic cyclic hydrocarbon groups with 1-5 rings, especially monocyclic and bicyclic groups. Any aromatic ring having two or more aromatic rings (bicyclic, etc.), the aromatic rings of aryl may be connected by single bond (such as biphenyl) or fused (such as naphthalene, anthracene, etc.). The aryl is preferably a C6-C12 aryl and refers to an aromatic cyclic hydrocarbon group containing 6, 7, 8, 9, 10, 11 or 12 ring carbon atoms. Examples of aryl (especially monocyclic and bicyclic groups) include but are not limited to phenyl, biphenyl or naphthyl. Aryl can be fused with heterocyclic groups through a single bond or any two adjacent ring C atoms, for example: benzotetrahydrofuranyl, benzotetrahydropyranyl, benzodioxanyl and

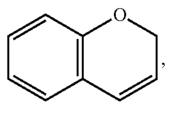, etc.

"Heteroaryl" refers to monocyclic, bicyclic, or tricyclic aromatic ring containing 5 to 12 ring atoms (5-12 membered), and containing at least 1 (e.g. 1, 2 or 3) ring heteroatoms selected from N, O or S, and the remaining ring atoms are C. It should be clear that the connection point of heteroaryl should be located on the heteroaromatic ring. Heteroaryl is preferred to have 5-8 ring atoms (5-8 membered), more preferably have 5-6 ring atoms (5-6 membered). Examples of heteroaryl include but are not limited to imidazolyl, aoxazolyl, isoxazolyl, thiazolyl, isothiazolyl, oxadiazolyl, thiadiazolyl, pyrazinyl, thienyl, furanyl, pyranyl, pyridyl, pyrrolyl, pyrazolyl, pyrimidinyl, quinolinyl, isoquinolinyl, benzofuranyl, benzothienyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinazinyl, naphthyridinyl, pterridinyl, carbazolyl, azepinyl, diazepinyl and acridinyl, etc.

"Polysubstituted" means being substituted by two or more substituents.

In the present invention, unless other stated, the alkyl, alkoxy, cycloalkyl, heterocyclyl, aryl, heteroaryl and other groups include substituted alkyl, alkoxy, cycloalkyl, heterocyclyl, aryl, heteroaryl, etc., the substituents such as (but not limited to) halogen, hydroxyl, cyano, acyl, sulfonyl, ester, sulfinyl, alkyl, cycloalkyl, heterocyclyl, aryl, heteroaryl, acyl, ester, etc.

"Deuterated compound" refers to the compound obtained by replacing one hydrogen atom (H) or multiple hydrogen atoms (H) with deuterium atoms (D) in a compound.

Active Ingredient

As use herein, the terms "compounds of the invention" or "active ingredients of the invention" are used interchangeably, and refers to a compound of formula I, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof.

The compound of formula I, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof has the following structure,

I

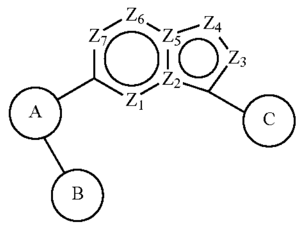

wherein, A, B, C, $Z_1$, $Z_2$, $Z_3$, $Z_4$, $Z_5$, $Z_6$ and $Z_7$ are as defined above.

Preferably, the compound of formula I, or the tautomer, or the mesomer, the racemate and the mixture of mesomer and racemate, or the enantiomer, the diastereomer and the mixture of enantiomer and diastereomer, or the pharmaceutically acceptable salt, or the deuterated compound thereof has a structure represented by formula III,

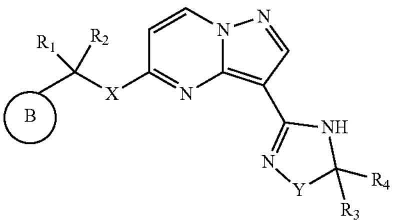

III wherein,

B, X, Y, $R_1$, $R_2$, $R_3$ and $R_4$ are as defined above.

The salt that the compound in the present invention may be formed are also within the scope of the present invention. Unless otherwise stated, the compound in the present invention is understood to include its salt. The term "salt" as used herein refers to a salt formed in the form of acid or base from inorganic or organic acid and base. Further, when the compound in the present invention contains a base fragment which includes, but is not limited to pyridine or imidazole, when contains an acid fragment which includes, but is not limited to carboxylic acid. The zwitter-ion that may form "inner salt" is included within the scope of the term "salt". Pharmaceutically acceptable (i.e., non-toxic, physiologically acceptable) salt is preferred, although other salts are also useful and may be used, for example, in the separation or purification steps of the preparation process. The compound of the present invention may form a salt, for example, compound I is reacted with a certain amount (such as an equivalent amount) of an acid or base, and precipitated in a medium, or freeze-dried in aqueous solution.

Base fragment contained in the compounds in the present invention includes but is not limited to amines or pyridine or imidazole rings, which may form salt with organic or inorganic acid. Typical acids that can form salts include hydrochloride, hydrobromide, hydroiodate, sulfate, bisulfate, nitrate, phosphate and acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, hydroxyethanesulfonate, benzenesulfonate, salicylate, picrate, glutamate, ascorbate, camphorate, camphor sulfonate, etc.

Acidic fragments that may be contained in some compounds of the invention includes, but not limited to carboxylic acid, which may form salts with various organic or inorganic bases. Salt formed by typical base includes ammonium salt, alkali metal salt (such as sodium, lithium and potassium salts), alkaline earth metal salt (such as calcium and magnesium salts), and salt formed by organic bases (such as organic amines), such as benzathine, dicyclohexylamine, hydrabamine (salt formed with N,N-bis (dehydroabietyl) ethylenediamine), N-methyl-D-glucanamine, N-methyl-D-glucoamide, tert-butyllamine, and the salt formed with amino acids such as arginine, lysine, etc. Basic nitrogen-containing groups can form quaternary ammonium salts with halides, such as small molecular alkyl halides (such as chlorides, bromides and iodides of methyl, ethyl, propyl and butyl), dialkyl sulfate (such as dimethyl, diethyl, dibutyl, and dipentyl sulfates), long chain halides (such as chlorides, bromides and iodides of decyl, dodecyl, tetradecyl, and tetradecyl), aralkyl halides (such as bromides of benzyl and phenyl), etc.

The prodrug and solvate of the compound in the present invention are also included within the scope of the present invention. The term "prodrug" herein refers to a compound resulting from the chemical transformation of a metabolic or chemical process to produce a compound, salt, or solvate in the present invention for the treatment of an associated disease. The compounds of the invention include solvates such as hydrates.

Compound, salt or solvate in the present invention, may be present in tautomeric forms such as amide and imino ether. All of these tautomers are part of the present invention.

Stereisomers of all compounds (e.g., those asymmetric carbon atoms that may be present due to various substitutions), include their enantiomeric forms and non-enantiomed forms, all belong to the protection scope of the present invention. The independent stereoisomer in the present invention may not coexist with other isomers (e.g., as a pure or substantially pure optical isomer with special activity), or may be a mixture (e.g., racemate), or a mixture formed with all other stereoisomers or a part thereof. The chiral center of the present invention has two configurations of S or R, which is defined by International Union of Pure and Applied Chemistry (IUPAC) in 1974. The racemization form can be solved by physical methods, such as fractional crystallization, or separation crystallization by derivation into diastereomers, or separation by chiral column chromatography. Individual optical isomer can be obtained from racemate by appropriate methods, including but not limited to conventional methods, such as recrystallization after salting with optically active acids.

Weight content of compound in the present invention obtained by preparation, separation and purification in turn is equal to or greater than 90%, such as equal to or greater than 95%, equal to or greater than 99% ("very pure" compound), and listed in the description of the text. In addition, the "very pure" compound of the present invention is also part of the present invention.

All configuration isomers of the compound of the present invention are within the scope, whether in mixture, pure or very pure form. The definition of the compound of the present invention comprises cis (Z) and trans (E) olefin isomers, and cis and trans isomers of carbocyclic and heterocyclic.

In the entire specification, the groups and substituents can be selected to provide stable fragments and compounds.

Specific functional groups and chemical term definitions are described as follows in detail. For the purposes of the present invention, the chemical elements are consistent with Periodic Table of the Elements, CAS version, *Handbook of Chemistry and Physics,* 75th Ed. The definition of a particular functional group is also described therein. In addition, the basic principles of Organic Chemistry as well as specific functional groups and reactivity described in "Organic Chemistry", Thomas Sorrell, University Science Books, Sausalito: 1999, the entire content of which is incorporated herein by reference.

Some compounds of the present invention may exist in specific geometric or stereoisomer forms. The present invention covers all compounds, including their cis and trans isomers, R and S enantiomers, diastereomers, (D) type isomers, (L) type isomers, racemic mixtures and other mixtures. In addition, asymmetric carbon atom can represent substituent, such as alkyl. All isomers and mixtures thereof are included in the present invention.

According to the invention, mixtures of isomers may contain a variety ratio of isomers. For example, mixtures with only two isomers may have the following combinations: 50:50, 60:40, 70:30, 80:20, 90:10, 95:5, 96:4, 97:3, 98:2, 99:1, or 100:0, all ratios of the isomers are within the scope of the present invention. Similar ratios readily understood by those of ordinary skill in the art and ratios for mixtures of more complex isomers are also within the scope of the present invention.

The invention also includes isotope labeled compounds, which are disclosed herein equivalent to the original compounds. However, in practice, it usually occurs when one or more atoms are replaced by atoms with a different atomic weight or mass number. Examples of compound isotopes that may be listed in the present invention include hydrogen, carbon, nitrogen, oxygen, phosphorus, sulfur, fluorine and chlorine isotopes, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$. The compound, or enantiomer, diastereomer, isomer, or pharmaceutically acceptable salt or solvate, wherein the compound containing isotopes or other isotope atoms of above compound are all within the scope of the invention. Some isotope-labeled compounds in the present invention, such as the radioactive isotopes of $^{3}H$ and $^{14}C$, are also included and are useful in experiments on the tissue distribution of drugs and substrates. Tritium ($^{3}H$) and Carbon-14 ($^{14}C$), which are relatively easy to prepare and detect, are the preferred choice. In addition, heavier isotope substitutions such as deuterium, i.e. $^{2}H$, have advantages in certain therapies due to their good metabolic stability, such as increased half-life or reduced dosage in vivo, and thus may be preferred in certain situations. Isotope-labeled compounds can be prepared by conventional methods through substituting readily available isotope-labeled reagents for non-isotopic reagents, and can be prepared using the disclosed scheme shown in the Example.

If the synthesis of a specific enantiomer of the compound of the invention is to be designed, it can be prepared by asymmetric synthesis, or derivatized with chiral adjuvant, separating the resulting diastereomeric mixture and removing the chiral adjuvant to obtain a pure enantiomer. In addition, if a molecule contains a basic functional group, such as an amino acid, or an acidic functional group, such as a carboxyl group, a diastereomer salt can be formed with a suitable optically active acids or bases, which can be separated by conventional means, such as crystallization or chromatography, to obtain a pure enantiomer.

As described herein, the compound in the present invention may be substituted with any number of substituents or functional groups to extend its scope. In general, whether the term "substituted" appears before or after the term "optional", the general formula that includes substituents in the compound of the present invention means the substitution of a specified structural substituent for a hydrogen radical. When multiple locations in a particular structure are replaced by multiple specific substituents, each location of the substituents can be the same or different. The term "substituted" as used herein includes all substitution that allows organic compounds to be substituted. Broadly speaking, the allowable substituents include non-cyclic, cyclic, branched, non-branched, carbocyclic and heterocyclic, aromatic ring and non-aromatic organic compounds. In the present invention, for example, heteroatom nitrogen, its valence state may be supplemented by a hydrogen substituent or by any permitted organic compound described above. Furthermore, the invention is unintentionally limited to the substituted organic compounds. The present invention considers that a combination of substituents and variable groups is good for the treatment of diseases in the form of stable compounds. The term "stable" herein refers to a stable compound which is sufficient for maintaining the integrity of the compound structure within a sufficiently long time, preferably in a sufficiently long time, which is hereby used for the above purposes.

The metabolites of the compounds of the present application and their pharmaceutically acceptable salts, and prodrugs that can be converted into the compounds of the present application and their pharmaceutically acceptable salts thereof in vivo, also included in the claims.

Preparation Method

The compound of the invention may be conveniently prepared by optionally combining the various synthetic methods described in this specification or known in the art, such a combination may be easily performed by a skilled person in the art to which the invention belongs.

Generally, in the preparation process, each reaction is usually carried out in an inert solvent at −60° C. to 100° C., preferably −60° C. to 80° C. The reaction time is usually 0.1-60 hours, preferably 0.5-48 hours.

The preferred synthetic route is as follows:

route 1

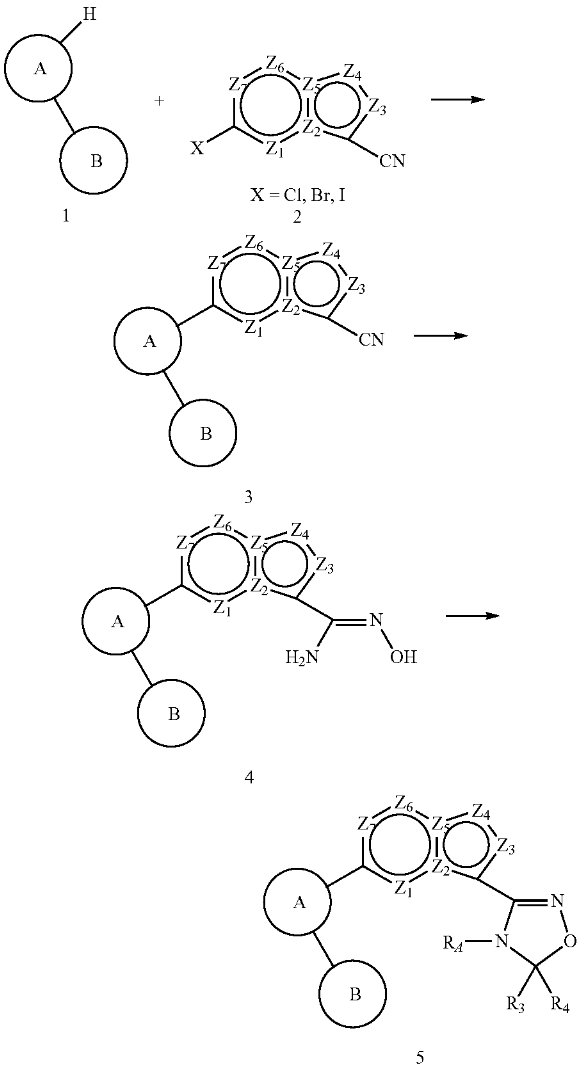

1 2 3 4 5 route 2

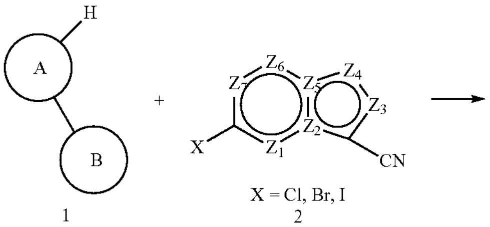

1

X = Cl, Br, I

2

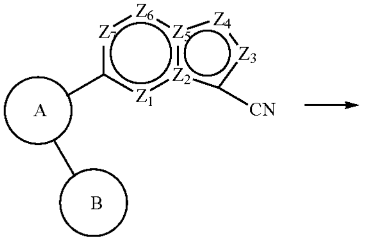

3

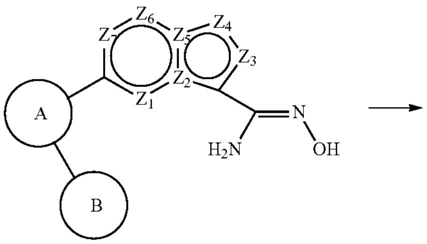

4

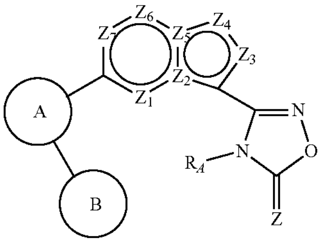

5 route 3

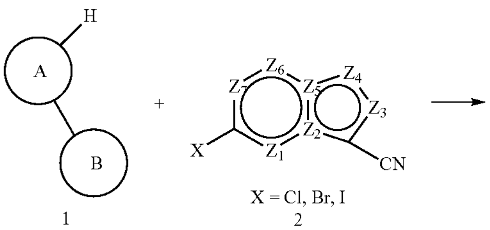

1

X = Cl, Br, I

2

-continued

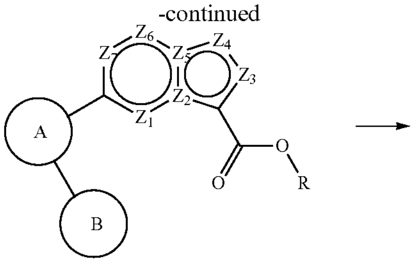

3

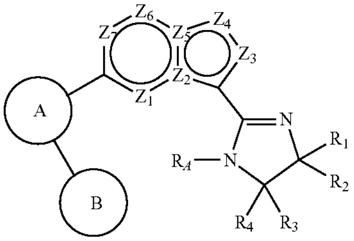

4 wherein Z is O; R is $C_1$-$C_6$ alkyl;

A, B, C, $Z_1$, $Z_2$, $Z_3$, $Z_4$, $Z_5$, $Z_6$, $Z_7$, $R_3$, $R_4$ and $R_A$ are as defined above;

wherein, in route 1: (1) compound 1 and compound 2 undergone nucleophilic substitution reaction in an inert solvent (such as ethanol and methanol) under the action of base (such as sodium carbonate, potassium carbonate, sodium hydroxide, triethylamine and pyridine, etc.) to give compound 3; (2) compound 3 reacted with hydroxylamine hydrochloride in an inert solvent (such as ethanol and methanol) under the action of a base (such as sodium carbonate, potassium carbonate, sodium hydroxide, triethylamine, pyridine, etc.) to give compound 4; (3) compound 4 reacted with dimethoxy acetonide in an inert solvent (e.g. 1, 2-dichloroethane and/or glacial acetic acid) to give the final product 5.

in route 2: (1) compound 1 and compound 2 undergone nucleophilic substitution reaction in an inert solvent (such as ethanol and methanol) under the action of base (such as sodium carbonate, potassium carbonate, sodium hydroxide, triethylamine and pyridine, etc.) to give compound 3; (2) compound 3 reacted with hydroxylamine hydrochloride in an inert solvent (such as ethanol and methanol) under the action of a base (such as sodium carbonate, potassium carbonate, sodium hydroxide, triethylamine, pyridine, etc.) to give compound 4; (3) compound 4 reacted with dimethoxy acetonide in an inert solvent (e.g. 1, 2-dichloroethane and/or glacial acetic acid) to give the final product 5.

in route 3: (1) compound 1 and compound 2 undergone nucleophilic substitution reaction in an inert solvent (such as toluene) under the action of base (such as sodium tert-butoxide, potassium tert-butoxide, sodium hydride, potassium hydride, potassium carbonate, cesium carbonate, potassium phosphate, potassium hydroxide, sodium hydroxide, etc.) to give compound 3; (2) compound 3 reacted with

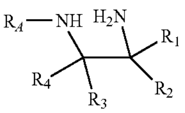

in the presence of trimethyl aluminum in an inert solvent (such as toluene) to give final product 4.

The starting materials of the present invention are known and commercially available, or can be synthesized according to the literature reported in the art.

Pharmaceutical Composition and Method of Administration

The pharmaceutical compositions of the present invention are used to prevent and/or treat the following diseases: inflammation, cancer, cardiovascular disease, infection, immunological disease, metabolic disease.

The compounds of the present invention can be used in combination with other drugs known to treat or improve similar conditions. When administered in combination, the original administration for the drug can remain unchanged, while compound of the present invention may be administered simultaneously or subsequently. Pharmaceutical composition containing one or more known drugs and the compound of the present invention may be preferred when administered in combination with one or more other drugs.

The drug combination also includes administering the compound of the present invention and other one or more known drugs at overlapping time. When the compound of the present invention is combined with other one or more drugs, the dose of the compound of the present invention or known drug may be lower than that of their individual use.

The dosage forms of the pharmaceutical composition of the present invention include (but are not limited to): injection, tablet, capsule, aerosol, suppository, pellicle, pill, liniment for external use, controlled release or sustained-release or nano formulation.

The pharmaceutical composition of the present invention comprises a compound of the present invention or a pharmaceutically acceptable salt and a pharmaceutically acceptable excipient or carrier with safe and effective amount. In which, "safe and effective amount" refers to the amount of compound is sufficient to significantly improve the condition, not to produce severe side effects. Typically, the pharmaceutical composition contains 1-2000 mg of the compound of the present invention per dosage, and preferably contains 10-1000 mg of the compound of the present invention per dosage. Preferably, "one dosage" is a capsule or a pill.

"Pharmaceutically acceptable carrier" refers to one or more compatible solid or liquid filler or gel substances, which are suitable for human use, and must be sufficiently pure and of sufficiently low toxicity. "Compatible" herein refers to each component of a composition can be mixed with the compound of the present invention and can be mixed with each other without appreciably reducing the efficacy of the compound. Examples of pharmaceutically acceptable carrier include cellulose and derivatives thereof (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as lauryl sodium sulfate), colorant, flavoring, stabilizer, antioxidant, preservative, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid; (b) binders, such as hydroxymethyl cellulose, alginate, gelatin, polyvinylpyrrolidone, sucrose and arabic gum; (c) humectant, such as, glycerol; (d) disintegrating agent, such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, lauryl sodium sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents such as water or other solvents, solubilizers and emulsifiers known in the art, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant that may be required if necessary, under sterile conditions.

Compounds of the present invention can be administrated alone, or in combination with other treatment means or therapeutic drugs.

When the pharmaceutical compositions are used, a safe and effective amount of compound of the present invention is administrated to a mammal (such as human) in need thereof, wherein the dose of administration is a pharmaceutically effective dose. For a person weighed 60 kg, the daily dose is usually 1-2000 mg, preferably 10-1000 mg. Of course, the particular dose should also depend on various factors, such as the route of administration, patient healthy status, which are all within the skills of an experienced physician.

The present invention also provides a preparation method of pharmaceutical composition comprising the step of mixing a pharmaceutically acceptable carrier with the compound or the pharmacically acceptable salt, stereoisomer, solvate or prodrug thereof of the present invention, thus forming the pharmaceutical composition.

The invention also provides a treatment method comprising the steps of administering the compound, or pharmaceutically acceptable salt, stereoisomer, solvate or prodrug thereof, or administering the pharmaceutical composition of the invention to a subject in need thereof to selectively inhibit fusion mutations and drug resistance mutations of ROS1, NTRK and ALK, etc.

The invention has the following main advantages:

(1) The compound of the invention has good inhibition ability to ROS1, NTRK and ALK kinase, especially excellent activity to drug-resistant mutation of these targets;

(2) The compound of the invention has better pharmacodynamics, pharmacokinetic properties and lower toxic and side effects;

(3) The compound of the invention has great potential to be developed into an effective drug for drug-resistant patients urgently needed clinically at present.

The technical solution of the present invention will be further described below, but the scope of protection of the present invention is not limited thereto.

Some specific examples are listed below for explanation.

Example 1

Synthetic Route:

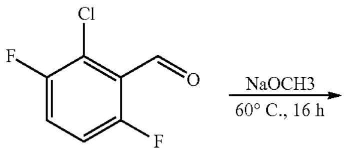

1

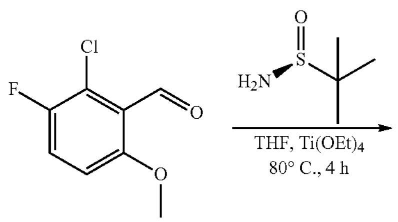

2

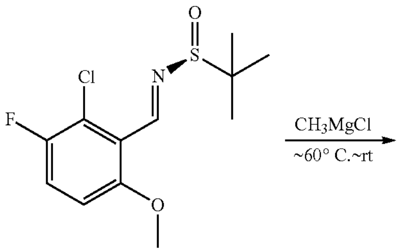

3

-continued

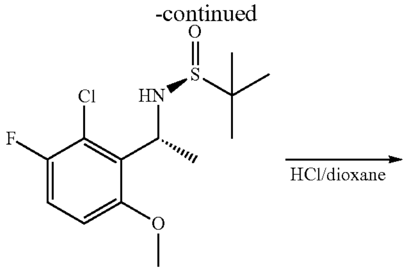

4

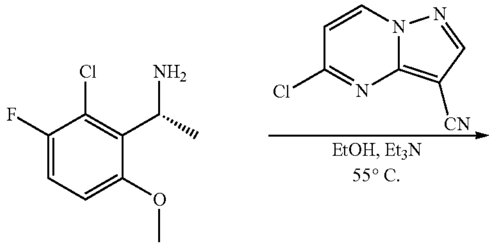

5

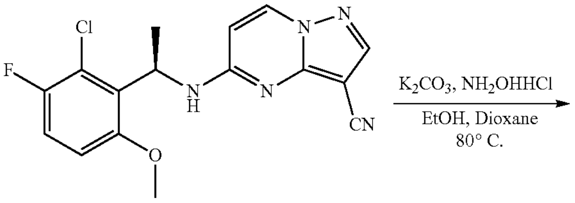

6

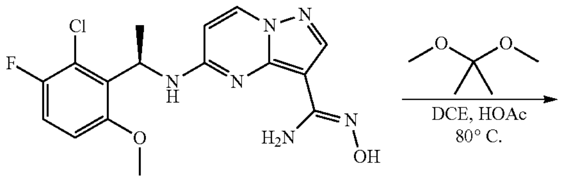

7

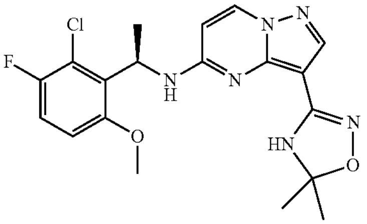

Example 1

Reaction Steps:

(1) Synthesis of compound 2: 100 mL single-neck flask, condenser tube, argon protection. Compound 1 (5.2 g) was weighed, and methanol (50 ml) and tetrahydrofuran (25 ml) were added, the temperature was raised to 60° C. under argon protection, 1M/L sodium methoxide solution (self-made) in methanol (32 ml) was slowly added dropwise, finished in 1 hour and then stirred overnight at 60° C. The next day, the solvent was evaporated, water and ethyl acetate were added for extraction, and then extracted with ethyl acetate again. The organic phases were combined, dried, evaporated and purified by column chromatography to obtain 4.21 g of an oily product. $^1$H NMR (400 MHz, $CDCl_3$) δ 10.48 (d, J=1.0 Hz, 1H), 7.31 (dd, J=9.2, 8.2 Hz, 1H), 6.88 (dd, J=9.2, 3.7 Hz, 1H), 3.92 (s, 3H).

(2) Synthesis of compound 3: A 250 mL single-neck flask with a sealed condensing tube above was filled with compound 2 (4.01 g), (R)-tert-butyl sulfinamide (3.87 g, 1.5 eq), tetraethyl titanate (9.73 g, 2.0 eq) and tetrahydrofuran (100 mL), stirred overnight at 80° C. and cooled on the next day. A large amount of saturated brine and ethyl acetate were added for extraction, the aqueous phase was extracted with dichloromethane once again. The organic phases were combined, dried, evaporated and purified by column chromatography to obtain 4.73 g of oily product, $^1$H NMR (400 MHz, $CDCl_3$) δ 8.93 (s, 1H), 7.23 (dd, J=9.1, 8.4 Hz, 1H), 6.85 (dd, J=9.2, 3.9 Hz, 1H), 3.88 (s, 3H), 1.30 (s, 9H).

(3) Synthesis of compound 4: compound 3 (4.73 g) and tetrahydrofuran (200 ml) were added into a 250 mL three-neck flask, protected with argon and stirred at room temperature for 10 min, then cooled to −10° C., then 3M methyl magnesium chloride (25 ml, 3 eq) in tetrahydrofuran was added, and the reaction was slowly raised to room temperature and stirred overnight. The next day, TLC monitoring showed that the reaction was completed. Water and ethyl acetate were added for extraction, and then extracted with ethyl acetate again. The organic phases were combined, dried, evaporated and purified by column chromatography to obtain 4.525 g of a solid product. $^1$H NMR (400 MHz, $CDCl_3$) δ 7.01 (td, J=9.2, 8.4 Hz, 1H), 6.76 (ddd, J=9.1, 6.9, 4.1 Hz, 1H), 5.33-4.39 (m, 2H), 3.87 (d, J=6.2 Hz, 3H), 1.57 (dd, J=56.9, 7.0 Hz, 3H), 1.17 (d, J=28.1 Hz, 9H).

(4) Synthesis of compound 5: compound 4 (4.525 g) and hydrochloric acid/dioxane (150 ml) were added in a 500 ml single-neck flask. Stirred at room temperature for 4 hours, monitored by TLC, and the raw materials were reacted completely. The solvent was evaporated directly, water was added, and then pH was adjusted to 9-10 with sodium carbonate aqueous solution. Extracted with ethyl acetate, extracted twice, dried and concentrated to obtain 2.86 g of a pale yellow oily product.

(5) Synthesis of compound 6: compound 5 (1.06 g), 5-chloropyrazolopyrimidin-3-carbonitrile (0.93 g, 1.0 eq), ethanol (60 ml) and triethylamine (1.581 g, 3.0 eq) were added into a 100 mL single-neck flask connected with a condenser tube, then stirred at room temperature for 10 min under the protection of argon gas, and then reacted overnight at 55° C. The next day, TLC monitoring showed that the reaction was completed, and direct suction filtration was carried out to obtain 0.93 g of powder solid product. $^1$H NMR (400 MHz, DMSO) δ 8.57 (d, J=7.6 Hz, 1H), 8.46 (d, J=7.3 Hz, 1H), 8.23 (s, 1H), 7.26 (t, J=9.0 Hz, 1H), 7.02 (dd, J=9.2, 4.3 Hz, 1H), 6.59 (d, J=7.6 Hz, 1H), 5.82 (q, J=7.1 Hz, 1H), 3.89 (s, 3H), 1.56 (d, J=7.2 Hz, 3H).

(6) Synthesis of compound 7: compound 6 (0.93 g), anhydrous potassium carbonate (1.12 g, 3 eq), hydroxylamine hydrochloride (0.563 g, 3 eq), ethanol (40 ml) and dioxane (20 ml) were added into a 100 ml single-neck flask and reacted overnight at 80° C. The next day, TLC monitoring showed that the reaction was completed. The solvent was directly evaporated, water and ethyl acetate were added. The water phase was extracted with dichloromethane once. The organic phases were combined, dried, evaporated and purified by column chromatography to obtain 0.411 g of pure product, $^1$H NMR (400 MHz, DMSO) δ 9.02 (s, 1H), 8.46 (d, J=7.6 Hz, 1H), 8.13 (d, J=7.5 Hz, 1H), 7.88 (s, 1H), 7.26 (t, J=9.0 Hz, 1H), 7.04 (dd, J=9.2, 4.3 Hz, 1H), 6.44 (d, J=7.6 Hz, 1H), 5.89-5.61 (m, 3H), 3.87 (s, 3H), 1.54 (d, J=7.2 Hz, 3H).

Synthesis of Compound Example 1: compound 7 (0.411 g), dimethoxy acetonide (0.457 g, 4 eq), 1,2-dichloroethane (15 ml) and glacial acetic acid (7.5 ml) were added, stirred at 80° C. for 4 hours, TLC monitoring showed that the reaction was completed. The solvent was directly evaporated, then water and dichloromethane were added for extraction, dried, evaporated and purified by column chromatography to obtain 170 mg of final product. $^1$H NMR (400 MHz, $CDCl_3$) δ 8.25-8.12 (m, 2H), 7.05 (dd, J=9.1, 8.2 Hz, 1H), 6.80 (dd, J=9.1, 4.0 Hz, 1H), 6.08 (t, J=30.1 Hz, 4H), 3.91 (s, 2H), 1.58 (t, J=5.8 Hz, 8H).

Example 2

Synthetic Route:

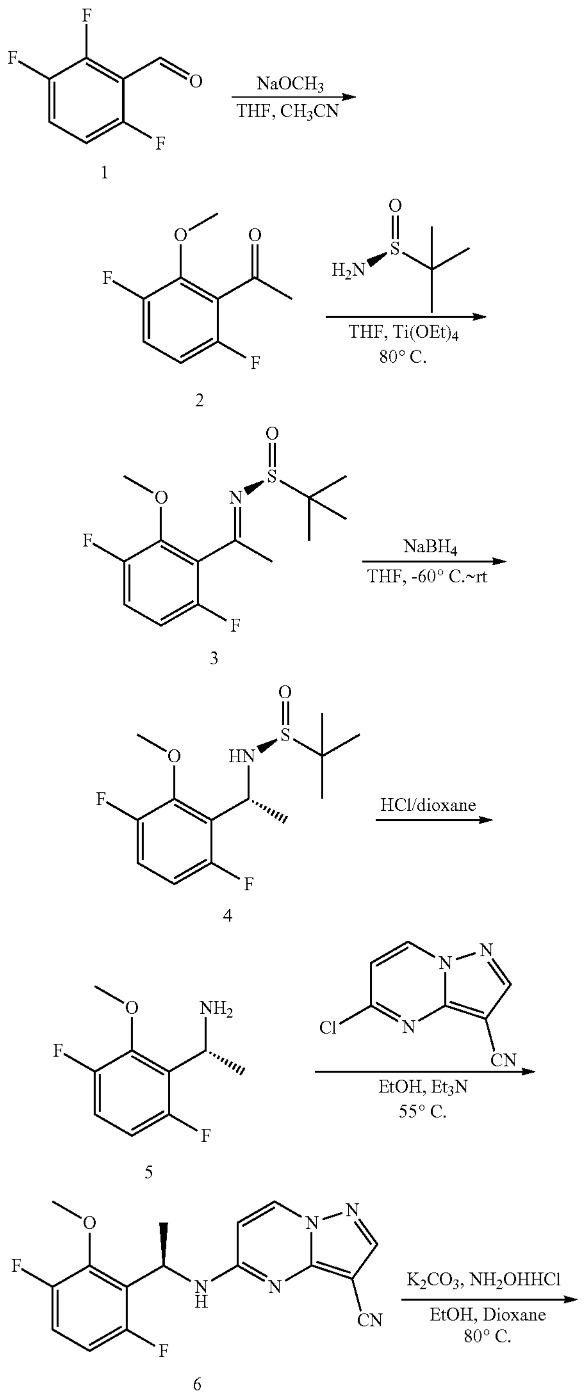

-continued

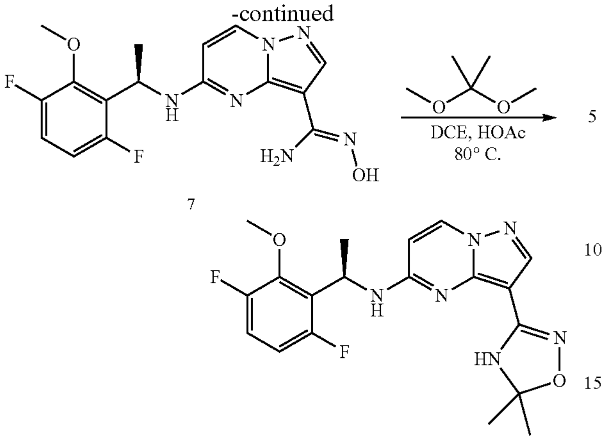

7

Example 2

Reaction Steps:

(1) Synthesis of compound 2: 500 mL three-neck flask was connected to a thermometer and a condenser tube, argon gas protection. Compound 1 (14.77 g) was weighed, methanol (200 ml) and tetrahydrofuran (85 ml) were added, the temperature was raised to 60° C. under argon protection, and 1M/L sodium methoxide solution (self-made) in methanol (85 ml) was slowly added dropwise, finished in 1 hour. Then stirred overnight at 60° C. The next day, the solvent was evaporated, water and ethyl acetate were added for extraction, and then extracted again with ethyl acetate to obtain 12 g of an oily product.

(2) Synthesis of compound 3: compound 2 (12 g), (R)-tert-butyl sulfinamide (19.52 g, 2.5 eq), tetraethyl titanate (36.8 g, 2.5 eq) and tetrahydrofuran (300 ml) were added into a 500 mL single-neck flask with a sealed condensing tube above. Stirred overnight at 80° C., and cooled down the next day. A large amount of saturated brine and ethyl acetate were added for extraction, the aqueous phase was extracted with dichloromethane once again. The organic phases were combined, dried, evaporated and purified by column chromatography to obtain 3.0 g of an oily product, (3) Synthesis of compound 4: compound 3 (3.0 g) and tetrahydrofuran (200 ml) were added into a 500 mL single-neck flask, and stirred at room temperature for 10 min under argon protection, then cooled to −60° C. with dry ice, and sodium borohydride (1.2 g, 3.0 eq) was added. The reaction was slowly raised to room temperature and stirred overnight. The next day, TLC monitoring showed that the reaction was completed. Water and ethyl acetate were add for extraction, and then extracted again with ethyl acetate. The organic phases were combined, dried, evaporated and purified by column chromatography to obtain 2.25 g of an oily product.

(4) Synthesis of compound 5: compound 4 (2.25 g) and hydrochloric acid/dioxane (50 ml) were added in a 100 mL single-neck flask, stirred at room temperature for 4 hours, monitored and the raw materials were reacted completely. The solvent was evaporated directly, water was added, and then pH was adjusted to 9-10 with sodium carbonate aqueous solution. Extracted with ethyl acetate twice, dried and concentrated to obtain 1.8 g of a pale yellow oily product.

(5) Synthesis of compound 6: compound 5 (0.92 g), 5-chloropyrazolopyrimidin-3-carbonitrile (0.81 g, 1.1 eq), ethanol (40 ml) and triethylamine (1.25 g, 3.0 eq) were added into a 100 mL single-neck flask connected with a condenser tube, then stirred at room temperature for 10 min under the protection of argon gas, and then reacted overnight at 55° C. The next day, TLC monitoring showed that the reaction was completed, then directly evaporated, and water and ethyl acetate were added for extraction. The organic phases were combined, dried, evaporated, and purified by column chromatography to obtain 0.95 g of an oily product.

(6) Synthesis of compound 7: compound 6 (0.95 g), anhydrous potassium carbonate (0.8 g, 2 eq), hydroxylamine hydrochloride (0.4 g, 2 eq), ethanol (40 ml) and dioxane (20 ml) were added into a 100 ml single-neck flask. Then reacted overnight at 80° C., and the next day, TLC monitoring showed that the reaction was completed. The solvent was directly evaporated, water and ethyl acetate were added for extraction, and the water phase was extracted with dichloromethane once again. The organic phases were combined, dried, evaporated and purified by column chromatography to obtain 0.4 g of pure product. $^1$H NMR (400 MHz, DMSO) δ 9.02 (s, 1H), 8.46 (d, J=7.6 Hz, 1H), 8.23 (d, J=7.1 Hz, 1H), 7.89 (s, 1H), 7.20 (ddd, J=11.1, 9.2, 5.2 Hz, 1H), 6.98 (td, J=9.6, 3.8 Hz, 1H), 6.40 (d, J=7.6 Hz, 1H), 5.78 (d, J=11.3 Hz, 2H), 5.55-5.33 (m, 1H), 3.91 (d, J=1.7 Hz, 3H), 1.59 (d, J=7.1 Hz, 3H).

Synthesis of compound Example 2: compound 7 (0.3 g), dimethoxy acetonide (0.345 g, 4 eq), 1, 2-dichloroethane (10 mL) and glacial acetic acid (7.5 mL) were added, stirred at 80° C. for 4 hours. TLC monitoring showed that the reaction was completed. The solvent was directly evaporated, then water and dichloromethane were added. Dried, evaporated and purified by column chromatography to obtain 130 mg of final product. $^1$H NMR (400 MHz, $CDCl_3$) δ 8.20 (s, 1H), 8.15 (d, J=7.6 Hz, 1H), 6.97 (ddd, J=10.8, 9.2, 5.3 Hz, 1H), 6.75 (td, J=9.4, 3.7 Hz, 1H), 6.34 (s, 1H), 6.06 (d, J=7.5 Hz, 1H), 5.79-5.59 (m, 2H), 4.03 (d, J=1.8 Hz, 2H), 1.72-1.64 (m, 5H), 1.60 (s, 3H).

Example 3

Synthetic Route:

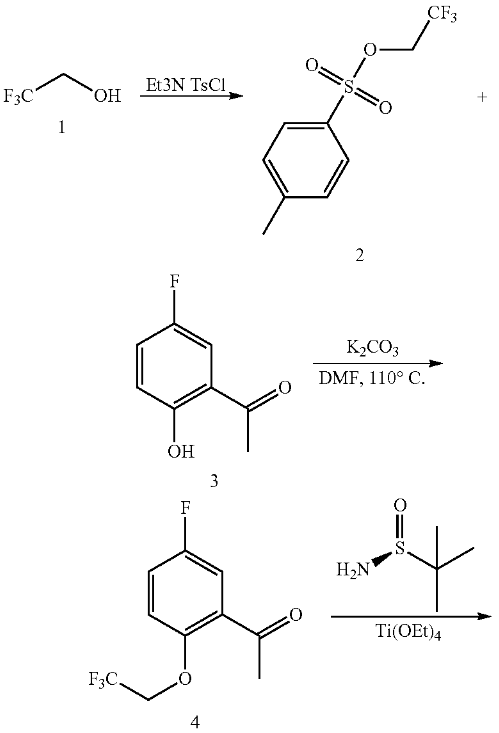

1

2

3

4

-continued

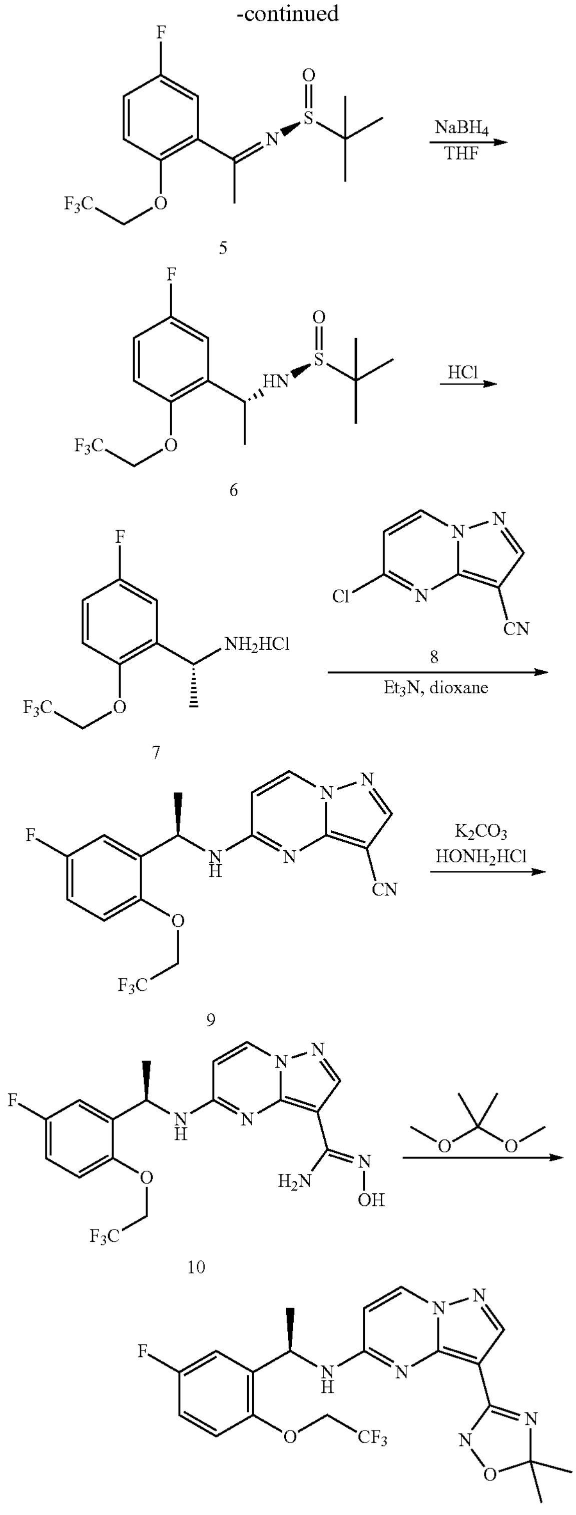

5

6

7

8

9

10

Example 3

Reaction Steps:

(1) Synthesis of compound 2: 500 mL three-neck flask was connected to a thermometer and a condenser tube, argon gas protection. Compound 1 (9.65 g) was weighed, dichloromethane (350 ml) and p-toluenesulfonyl chloride (23.84 g, 1.3 eq) were added, the temperature was reduced to 0° C. under argon protection, triethylamine (29.24 g, 3.0 eq) was slowly added dropwise and finished in 10 min, and then stirred overnight at room temperature. The next day, water and dichloromethane were added, and extracted again with dichloromethane, dried, evaporated and purified by column chromatography to obtain 20 g of product.

(2) Synthesis of compound 4: 500 mL three-neck flask was connected to a thermometer and a condenser tube, argon gas protection. Compound 2 (20 g) was weighed, N, N-dimethylformamide (350 ml) and compound 3 (12.13 g, 1 eq) were added, and anhydrous potassium carbonate (54.33 g, 5 eq) was added. The temperature was raised to 60° C. under argon and stirred overnight. The next day, water and ethyl acetate were added, extracted again with ethyl ester, dried, evaporated, and purified by column chromatography to obtain 13 g of an oily product. Yield: 70.3%. $^1H$ NMR (400 MHz, $CDCl_3$) δ 7.51 (dd, J=8.8, 3.3 Hz, 1H), 7.19 (ddd, J=9.0, 7.2, 3.3 Hz, 1H), 6.88 (dd, J=9.0, 3.9 Hz, 1H), 4.43 (q, J=7.9 Hz, 2H), 2.63 (s, 3H).

(3) Synthesis of compound 5: compound 4 (13 g), (R)-tert-butyl sulfinamide (13.33 g, 1.5 eq), tetraethyl titanate (25.13 g, 2.0 eq) and tetrahydrofuran (300 mL) were added into a 500 mL single-neck flask with a sealed condensing tube above, stirred overnight at 80° C. and cooled the next day. A large amount of saturated brine and ethyl acetate were added for extraction, the aqueous phase was extracted with dichloromethane once again, the organic phases were combined, dried, evaporated and purified by column chromatography to obtain 9.6 g of an oily product, yield: 51.6%.

(4) Synthesis of compound 6: compound 5 (9.6 g) and tetrahydrofuran (150 ml) were added into a 250 mL single-neck flask, and stirred at room temperature for 10 min under argon protection, then cooled to −60° C. with dry ice, and sodium borohydride (3.23 g, 3 eq) was added. The reaction was slowly raised to room temperature and stirred overnight. The next day, detected by TLC. Saturated ammonium chloride aqueous solution and ethyl acetate were added, and extracted once again with ethyl acetate. The organic phases were combined, dried, evaporated and purified by column chromatography to obtain 0.9 g of an oily product. $^1H$ NMR (400 MHz, $CDCl_3$) δ 7.05 (dd, J=8.8, 3.1 Hz, 1H), 6.94 (ddd, J=8.9, 7.7, 3.1 Hz, 1H), 6.78 (dd, J=9.0, 4.3 Hz, 1H), 4.67 (p, J=6.8 Hz, 1H), 4.47-4.32 (m, 2H), 3.79 (d, J=6.9 Hz, 1H), 1.50 (d, J=6.8 Hz, 3H), 1.21 (s, 9H).

(5) Synthesis of compound 7: compound 6 (0.9 g) and hydrochloric acid/dioxane (50 ml) were added in a 100 mL single-neck flask, stirred at room temperature for 4 hours, detected by TLC and the raw materials were reacted completely. The solvent was directly evaporated to obtain 0.865 g of pale yellow solid.

(6) Synthesis of compound 9: compound 7 (0.865 g), 5-chloropyrazolopyrimidin-3-carbonitrile (0.562 g, 1 eq), ethanol (40 ml) and triethylamine (0.96 g, 3 eq) were added into a 100 ml single-neck flask. Connected to a condenser tube and argon protection, stirred at room temperature for 10 min, and then reacted overnight at 55° C. The next day, directly evaporated, water and ethyl acetate were added for extraction, dried, evaporated and purified by column chromatography to obtain 0.988 g of an oily product.

(7) Synthesis of compound 10: compound 9 (0.988 g), anhydrous potassium carbonate (1.08 g, 3 eq), hydroxylamine hydrochloride (0.544 g, 3 eq), ethanol (40 ml) and dioxane (20 ml) were added into a 100 ml single-neck flask and reacted overnight at 80° C. The next day, detected by TLC. The solvent was directly evaporated, water and ethyl acetate were added for extraction, and the water phase was extracted with dichloromethane once again. The organic phases were combined, dried, evaporated and purified by column chromatography to obtain 0.65 g of pure product, yield: 60.5%. $^1H$ NMR (400 MHz, DMSO) δ 9.00 (s, 1H), 8.55 (dd, J=38.2, 7.8 Hz, 1H), 8.28 (d, J=6.5 Hz, 1H), 7.92 (d, J=33.3 Hz, 1H), 7.18-7.02 (m, 3H), 6.47 (dd, J=77.2, 7.8 Hz, 1H), 5.63 (s, 2H), 5.44-5.27 (m, 1H), 5.08-4.74 (m, 2H), 1.42 (d, J=6.9 Hz, 3H).

Synthesis of compound Example 3: compound 10 (0.65 g), dimethoxy acetonide (0.656 g, 4 eq), 1, 2-dichloroethane (15 ml) and glacial acetic acid (7.5 ml) were added to a reaction flask and stirred at 80° C. for 4 hours. The solvent was directly evaporated, water and dichloromethane were added for extraction, dried, evaporated and purified by column chromatography to obtain 180 mg of the final product. The HPLC purity was 99%. $^1H$ NMR (400 MHz, $CDCl_3$) δ 8.29-8.10 (m, 2H), 7.03 (dd, J=8.6, 2.9 Hz, 1H), 7.00-6.92 (m, 1H), 6.83 (dd, J=9.0, 4.2 Hz, 1H), 6.08 (d, J=7.6 Hz, 1H), 5.79 (s, 1H), 5.51 (d, J=5.5 Hz, 1H), 5.25 (s, 1H), 4.53-4.29 (m, 2H), 1.62 (s, 3H), 1.59 (s, 3H), 1.47 (s, 3H).

Example 4

Synthetic Route:

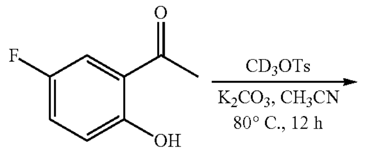

1

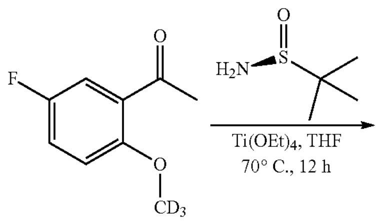

2

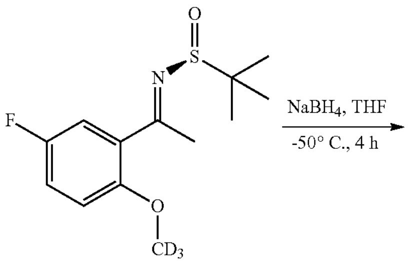

3

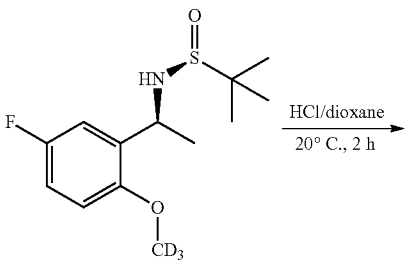

4

-continued

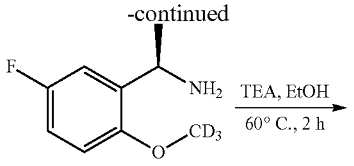

5

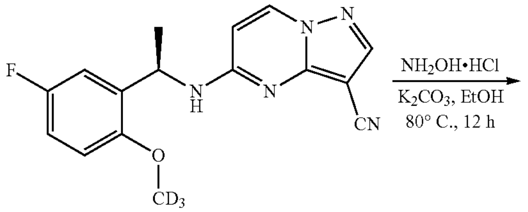

6

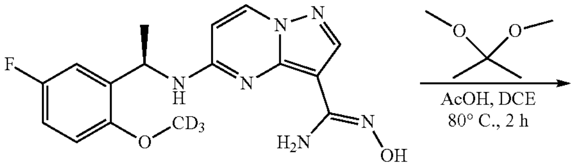

7

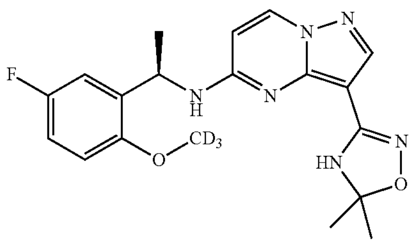

Example 4

Reaction Steps:

(1) Synthesis of compound 2: compound 1 (6.6 g, 42.8 mmol, 1 eq) was dissolved in acetonitrile (100 mL) solution, and $CD_3OTS$ (9.72 g, 51.4 mmol, 1.2 eq) and $K_2CO_3$ (8.88 g, 64.2 mmol, 1.5 eq) were added, and reacted at 80° C. for 12 h. After the raw materials were reacted completely, water and ethyl acetate were added for extraction, and washed with brine for three times. The organic phases were combined, dried over anhydrous sodium sulfate, and the organic phase was evaporated to obtain the compound 2 (7.0 g, 40.9 mmol, 95.5% yield).

(2) Synthesis of compound 3: compound 2 (6.0 g, 35.1 mmol, 1.0 eq) was dissolved in 60 mL dry THF solution, and (R)-(+)-tert-butyl sulfinamide (8.5 g, 70.1 mmol, 2 eq) and Ti $(OEt)_4$ (16.0 g, 70.1 mmol, 2 eq) were added, and reacted at 70° C. for 12 h. After the raw materials were reacted completely, water and ethyl acetate were added for extraction, and washed with brine for three times. The organic phases were combined, dried over anhydrous sodium sulfate, and the organic phase was evaporated and purified by column chromatography (petroleum ether:ethyl acetate=4:1) to obtain compound 3 (8.0 g, 29.1 mmol, yield 83.2%).

(3) Synthesis of compound 4: compound 3 (3.0 g, 10.9 mmol, 1.0 eq) was dissolved in 30 mL dry THF solution, $NaBH_4$ (1.24 g, 32.8 mmol, 3 eq) was added under −50° C., and the reaction was continued for 4 h under −50° C. After the raw materials were reacted completely, saturated ammonium chloride aqueous solution was added to quench, extracted with ethyl acetate and washed with brine for three times. The organic phases were combined, dried over anhydrous sodium sulfate. The organic phase was evaporated and purified by column chromatography (petroleum ether:ethyl acetate=8:1) to obtain compound 4 (1 g, 3.62 mmol, yield 33.1%).

(4) Synthesis of compound 5: 4M dioxane hydrochloride (10 mL) was added into compound 4 (1.0 g, 3.62 mmol, 1 eq) under ice bath, and continued to react at 0° C. for 1 h. After the raw materials were reacted completely, saturated sodium carbonate aqueous solution was added to quench, extracted with ethyl acetate, and washed with brine for three times. The organic phases were combined, dried over anhydrous sodium sulfate. The organic phases were evaporated to obtain compound 5 (0.5 g, yellow oily liquid, yield: 80.2%).

(5) Synthesis of compound 6: compound 5 (500 mg, 2.9 mmol, 1 eq) was dissolved in ethanol (8 mL), and then the compound 5a (622 mg, 3.48 mmol, 1.2 eq) and triethylamine (881 mg, 8.71 mmol, 2 eq) were added. Then the temperature was raised to 60° C. to react for 2 h. After the raw materials were reacted completely, the solvent was evaporated and purified by column chromatography (petroleum ether:ethyl acetate=2:1) to obtain compound 6 (0.75 g, 2.39 mmol, yield 82.2%).

MS: 300 (M+H+).

(6) Synthesis of compound 7: compound 6 (700 mg, 2.23 mmol, 1 eq) was dissolved in ethanol (10 ml), then hydroxylamine hydrochloride (310 mg, 4.45 mmol, 2 eq) and potassium carbonate (616 mg, 4.45 mmol, 2 eq) were added, then the reaction temperature was raised to 80° C. to react for 12 h. After the raw materials were reacted completely, water and ethyl acetate were added for extraction, and washed with brine for three times. The organic phases were combined, dried over anhydrous sodium sulfate. The organic phase was evaporated and purified by column chromatography (dichloromethane:methanol=50:1) to obtain compound 7 (700 mg, 2.02 mmol, yield 90.5%).

Synthesis of compound Example 4: compound 7 (400 mg, 1.15 mmol, 1 eq) was dissolved in 5 mL acetic acid and 1, 2-dichloroethane (5 mL), and then compound 7a (480 mg, 4.61 mmol, 4 eq) was added, and then the temperature was raised to 80° C. to react for 2 h. After the raw materials were reacted completely, saturated sodium carbonate aqueous solution was added to quench, ethyl acetate were added for extraction, and washed with brine for three times. The organic phases were combined, dried over anhydrous sodium sulfate. The organic phase was evaporated and purified by column chromatography (petroleum ether:ethyl acetate=0:1) to obtain compound Example 4 (300 mg, white solid, 0.77 mmol, yield: 67.2%). $^1$H NMR (400 MHz, $CDCl_3$) δ 8.17 (d, J=7.6 Hz, 1H), 8.15 (s, 1H), 6.98 (dd, J=8.8, 3.3 Hz, 1H), 6.95-6.88 (m, 1H), 6.86 (dd, J=8.8, 4.4 Hz, 1H), 6.17 (d, J=6.4 Hz, 1H), 5.95 (s, 1H), 5.86 (d, J=5.4 Hz, 1H), 1.62 (s, 3H), 1.54 (d, J=6.9 Hz, 3H), 1.44 (s, 3H).

Example 5

Synthetic Route:

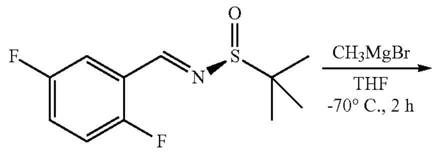

1

-continued

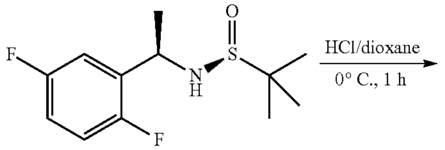

2

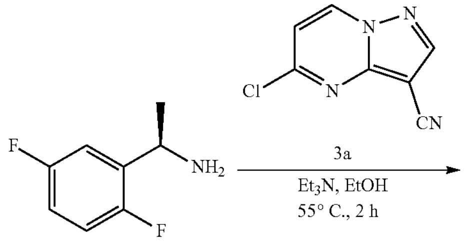

3

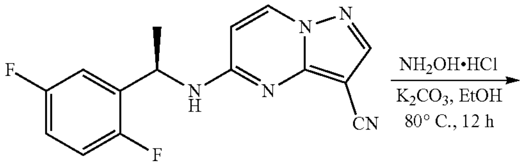

4

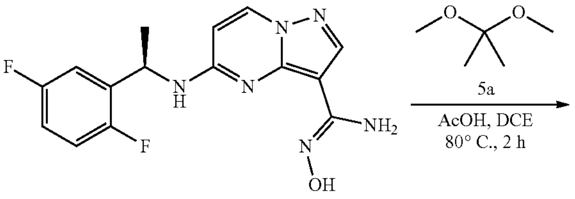

5

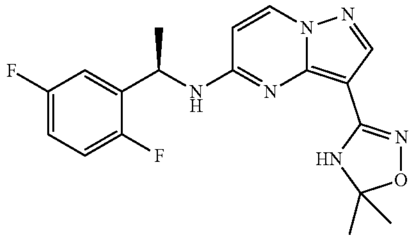

Example 5

Reaction Steps:

(1) Synthesis of compound 2: compound 1 (8 g, 32.6 mmol, 1 eq) was dissolved in dry tetrahydrofuran (60 mL), and magnesium methyl bromide solution (21 mL, 65.2 mmol, 3 M, 2 eq) was added dropwise at −70° C. After addition was completed, the reaction was continued to react for 2 h. After the raw materials were reacted completely, saturated ammonium chloride aqueous solution was added to quench, extracted with ethyl acetate and washed with brine for three times. The organic phases were combined, dried over anhydrous sodium sulfate. The organic phase was evaporated and purified by column chromatography (petroleum ether:ethyl acetate=4:1) to obtain compound 2 (2 g, yellow solid, yield 23.5%).

(2) Synthesis of compound 3: 4M dioxane hydrochloride (10 mL) was added into compound 2 (1.5 g, 5.74 mmol, 1 eq) under ice bath, and reacted at 0° C. for 1 h. After the raw materials were reacted completely, saturated sodium carbonate aqueous solution was added to quench, extracted with ethyl acetate, and washed with brine for three times. The organic phases were combined, dried over anhydrous sodium sulfate. The organic phases were evaporated to obtain compound 3 (0.8 g, yellow oily liquid, yield: 88.7%).

(3) Synthesis of compound 4: compound 3 (200 mg, 1.27 mmol, 1 eq) was dissolved in ethanol (4 mL), and then compound 3a (272 mg, 1.53 mmol, 1.2 eq) and triethylamine (257 mg, 2.55 mmol, 2 eq) were added. Then the temperature was raised to 55° C. to react for 2 h. After the raw materials were reacted completely, the solvent was evaporated, and purified by column chromatography (petroleum ether:ethyl acetate=2:1) to obtain compound 4 (150 mg, white solid, yield 39.4%).

MS: 300 (M+H+).

(4) Synthesis of compound 5: compound 4 (150 mg, 0.5 mmol, 1 eq) was dissolved in ethanol (2 ml), then hydroxylamine hydrochloride (70 mg, 1.0 mmol, 2 eq) and potassium carbonate (138 mg, 1.0 mmol, 2 eq) were added, then the reaction temperature was raised to 80° C. to react for 12 h. After the raw materials were reacted completely, water and ethyl acetate were added for extraction, and washed with brine for three times. The organic phases were combined, dried over anhydrous sodium sulfate. The organic phase was evaporated and purified by column chromatography (dichloromethane:methanol=50:1) to obtain compound 5 (50 mg, brown oily liquid, yield 30.0%).

Synthesis of compound Example 5: compound 5 (50 mg, 0.15 mmol, 1 eq) was dissolved in acetic acid (0.5 mL) and 1, 2-dichloroethane (0.5 mL), and then compound 5a (62 mg, 0.6 mmol, 4 eq) was added. Then the temperature was raised to 80° C. to react for 2 h. After the raw materials were reacted completely, saturated sodium carbonate aqueous solution was added to quench, extracted with ethyl acetate, and washed with brine for three times. The organic phases were combined, dried over anhydrous sodium sulfate. The organic phase was evaporated and purified by column chromatography (petroleum ether:ethyl acetate=0:1) to obtain Example 5 (20 mg, white solid, 35.7% yield). $^1$H NMR (400 MHz, $CDCl_3$) δ 8.21 (d, J=7.6 Hz, 1H), 8.18 (s, 1H), 7.09-6.99 (m, 2H), 6.92 (m, 1H), 6.16 (d, J=7.6 Hz, 1H), 5.94 (s, 1H), 5.55 (d, J=5.7 Hz, 1H), 5.38 (m, 1H), 1.64 (s, 3H), 1.60 (s, 3H), 1.50 (s, 3H). MS: 373 (M+H+).

Example 6

Synthetic Route:

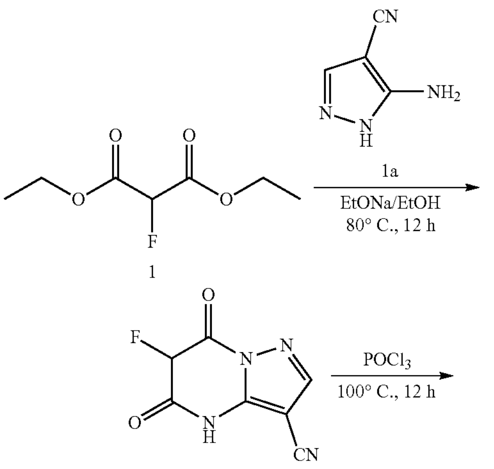

1a

1

2

-continued

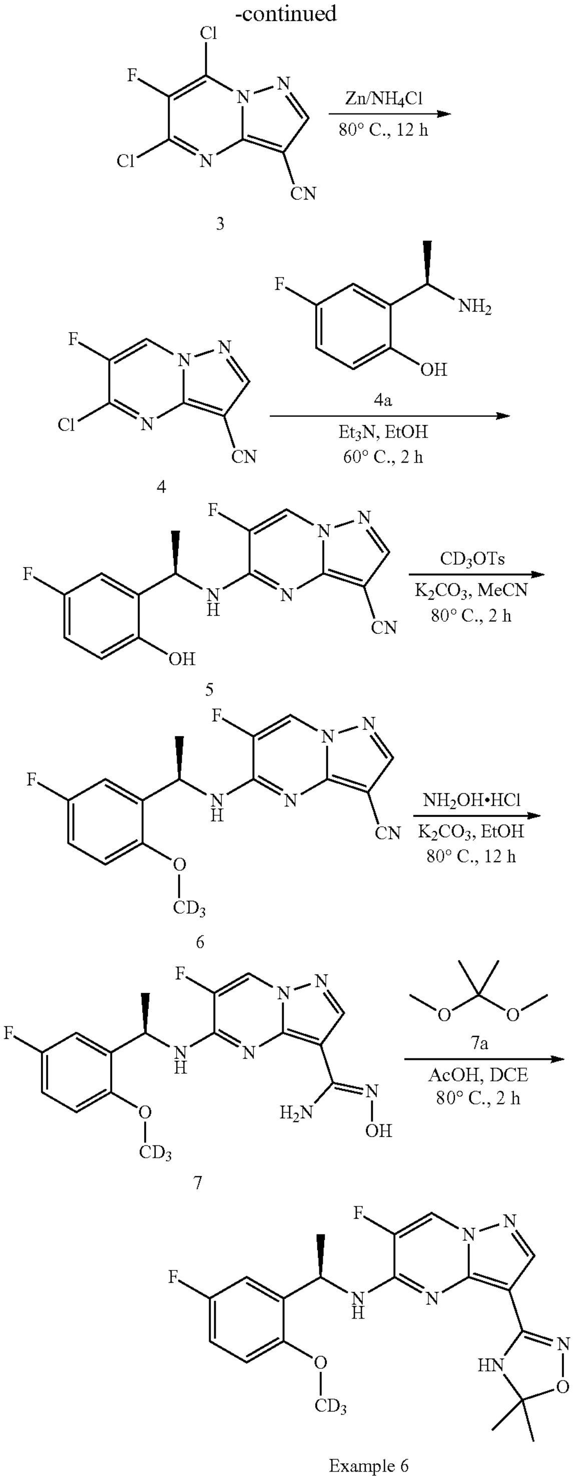

3

4a

4

5

6

7a

7

Example 6

Reaction Steps:

(1) Synthesis of compound 2: compound 1a (10 g, 92.5 mmol, 1 eq) and compound 1 (17.3 g, 97.1 mmol, 1.05 eq) were dissolved in 200 mL ethanol, EtONa (8.81 g, 129.5 mmol, 1.4 eq) was added, and the temperature was raised to 80° C. to react for 12 h. After the raw materials were reacted completely, the solvent was evaporated, water was added, pH was adjusted to 2-3 with 1M HCl, precipitate was precipitated. The precipitate was filtered and dried to obtain compound 2 (14 g, 72.12 mmol, yield 66.8%).

(2) Synthesis of compound 3: compound 2 (14 g, 72.12 mmol, 1 eq) was added to $POCl_3$ (100 mL), and reacted at 100° C. for 12 h. After the raw materials were reacted completely, the solvent was evaporated, and purified by column chromatography to obtain compound 3 (2.2 g, 9.52 mmol, yield 13.2%).

(3) Synthesis of compound 4: compound 3 (2.2 g, 9.52 mmol, 1 eq) was dissolved in ethanol (42 ml), tetrahydrofuran (14 ml) and water (28 ml), then Zn powder (3.11 g, 47.6 mmol, 5 eq) and $NH_4Cl$ (2.04 g, 38.1 mmol, 4 eq) were added, then reacted at 20° C. for 10 minutes. After the raw materials were reacted completely, water and ethyl acetate were added for extraction, and washed with brine for three times. The organic phases were combined, dried over anhydrous sodium sulfate. The organic phase was evaporated and purified by column chromatography to obtain compound 4 (1.0 g, 5.09 mmol, yield 53.4%).

(4) Synthesis of compound 5: compound 4a (500 mg, 3.22 mmol, 1 eq) was dissolved in ethanol (6 ml), then compound 4 (696 mg, 3.54 mmol, 1.1 eq) and triethylamine (978 mg, 9.67 mmol, 3 eq) were added. The temperature was raised to 60° C. to react for 2 h. After the raw materials were reacted completely, the solvent was evaporated, purified by column chromatography (petroleum ether:ethyl acetate=2:1) to obtain compound 5 (600 mg, white solid, yield 59.0%).

(5) Synthesis of Compound 6: Compound 5 (600 mg, 1.9 mmol, 1 eq) was dissolved in 6 mL acetonitrile, then $CD_3OTs$ (432 mg, 2.28 mmol, 1.2 eq) and potassium carbonate (395 mg, 2.85 mmol, 2 eq) were added, then heated to 80° C. to react for 2 h. After the raw materials were reacted completely, water and ethyl acetate were added for extraction, and washed with brine for three times. The organic phases were combined, dried over anhydrous sodium sulfate. The organic phase was evaporated and purified by column chromatography to obtain compound 6 (400 mg, 1.2 mmol, yield 63.2%).

(6) Synthesis of compound 7: compound 6 (250 mg, 0.75 mmol, 1 eq) was dissolved in ethanol (5 ml), then hydroxylamine hydrochloride (105 mg, 1.5 mmol, 2 eq) and potassium carbonate (208 mg, 1.5 mmol, 2 eq) were added, then the reaction temperature was raised to 80° C. to react for 12 h. After the raw materials were reacted completely, water and ethyl acetate were added for extraction, and washed with brine for three times. The organic phases were combined, dried over anhydrous sodium sulfate. The organic phase was evaporated and and purified by column chromatography (dichloromethane:methanol=50:1) to obtain compound 7 (250 mg, brown oily liquid, yield 91.0%).

Synthesis of Compound Example 6: compound 7 (250 mg, 0.68 mmol, 1 eq) was dissolved in acetic acid (2 ml) and 1, 2-dichloroethane (2 ml), then compound 7a (285 mg, 2.74 mmol, 4 eq) was added and the temperature was raised to 80° C. to react for 2 h. After the raw materials were reacted completely, saturated sodium carbonate aqueous solution was added to quench, extracted with ethyl acetate, and washed with brine for three times. The organic phases were combined, dried over anhydrous sodium sulfate. The organic phase was evaporated and purified by column chromatography (petroleum ether:ethyl acetate=0:1) to obtain Example 6 (50 mg, white solid, yield 18.0%). $^1H$ NMR (400 MHz, $CDCl_3$) δ 8.27 (d, J=5.6 Hz, 1H), 8.18 (s, 1H), 6.94 (m, 2H), 6.88 (m, 1H), 5.87 (d, J=6.0 Hz, 1H), 5.71 (s, 1H), 5.36 (m, 1H), 1.62 (m, 6H), 1.44 (s, 3H).

Example 7

Synthetic Route:

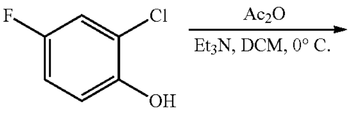

1

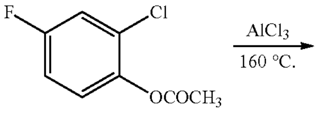

2

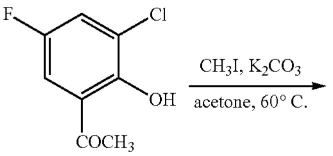

3

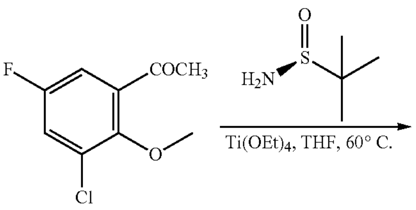

4

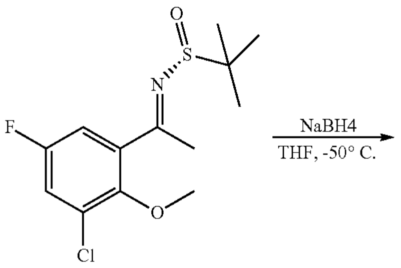

5

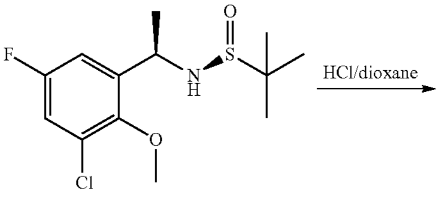

6

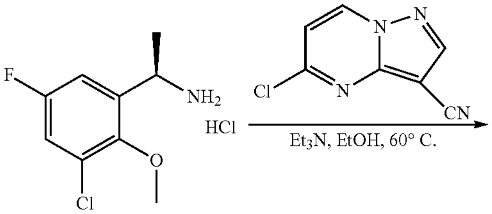

7

-continued

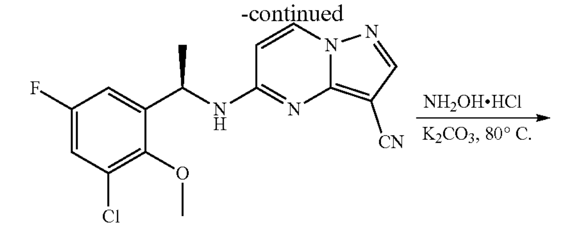

8

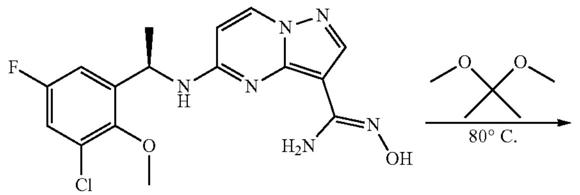

9

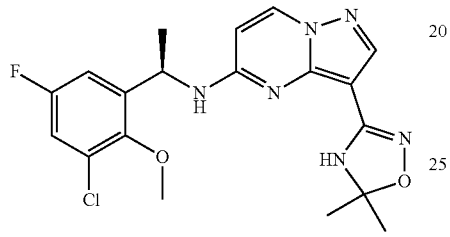

Example 7

Reaction Steps:

(1) Synthesis of compound 2: 6 g of compound 1 and triethylamine (4.97 g, 1.2 eq) were dissolved in dichloromethane in a 100 mL three-neck flask, and acetyl chloride (3.86 g, 1.2 eq) was slowly added at 0° C. The reaction was monitored by TLC until it was completed. Extracted with water and ethyl acetate, dried over anhydrous sodium sulfate, evaporated, and purified by column chromatography to obtain 7 g of compound 2. GC-MS [M] was 188.

(2) Synthesis of compound 3: compound 2 (7 g) and aluminum trichloride (14.86 g, 3 eq) were added into a 100 mL round bottom flask, the temperature was raised to 160° C., the reaction was stirred for 1 h. TLC monitoring showed that the reaction was completed. Hydrochloric acid (6 mol/L) was added, extracted with ethyl acetate, dried over anhydrous sodium sulfate, evaporated and purified by column chromatography to obtain 6.16 g of compound 3. GC-MS [M] was 188.

(3) Synthesis of compound 4: compound 3 (2 g) and potassium carbonate (7.3 g, 5 eq) were dissolved in acetone in a 100 mL round bottom flask, methyl iodide (7.5 g, 5 eq) was added under stirring, the temperature was raised to 60° C., and the reaction was monitored by TLC until it was completed. Extracted with ethyl acetate, dried over anhydrous sodium sulfate, evaporated, and separated by column chromatography to obtain 2.05 g of compound 4. LC-MS [M+1] was 203.

(4) Synthesis of compound 5: compound 4 (2.05 g) and R-tert-butyl sulfinamide (2.42 g, 2 eq) were dissolved in anhydrous tetrahydrofuran in a 100 mL round bottom flask, ethyl titanate (4.56 g, 2 eq) was added under stirring, and the temperature was raised to 60° C. The reaction was monitored by TLC until it was completed. Water was added, suction-filtered, extracted with ethyl acetate, evaporated, and separated by column chromatography to obtain 2.63 g of compound 5. LC-MS [M+1] was 306.

(5) Synthesis of compound 6: compound 5 (2.63 g) was dissolved in anhydrous tetrahydrofuran in a 100 mL three-neck flask, sodium borohydride (0.98 g, 3 eq) was added at −50° C., and the reaction was monitored by TLC until it was completed. After quenching with aqueous ammonium chloride solution, extracted with ethyl acetate. The organic phase was dried over anhydrous sodium sulfate, and separated by column chromatography to obtain 1.76 g of compound 6. LC-MS [M+1] was 308.

(6) Synthesis of compound 7: compound 6 (1.76 g) was added in a 100 ml round bottom flask, and dioxane hydrochloride (10 ml) was added. After stirring for 1 h, TLC showed that the reaction was completed. Filter cake 1.1 g compound 7 was obtained by suction filtration.

(7) Synthesis of compound 8: compound 7 (1.1 g) and 5-chloro-3-cyanopyrazolo [1, 5-α] pyrimidine (0.98 g, 1.2 eq) were dissolved in absolute ethanol in a 100 mL round bottom flask, and triethylamine (1.8 g, 4 eq) was added dropwise under stirring. The temperature was raised to 60° C., and the reaction was monitored by TLC until it was completed. The solvent was evaporated and extracted with water and ethyl acetate. The organic phase was dried over anhydrous sodium sulfate and separated by column chromatography to obtain 1.35 g of compound 8. LC-MS [M+1] was 346.

(8) Synthesis of compound 9: compound 8 (1.35 g), hydroxylamine hydrochloride (1 g, 4 eq), potassium carbonate (2 g, 4 eq) and ethanol (10 ml) were added into a 100 ml round bottom flask. The temperature was raised to 80° C., and the reaction was monitored by TLC until it was completed. The solvent was spin-dried and extracted with water and ethyl acetate. The organic phase was dried over anhydrous sodium sulfate and separated by column chromatography to obtain 0.73 g of compound 9. LC-MS [M+1] was 379.

Synthesis of Example 7: compound 9 (0.73 g) was dissolved in acetic acid (4 ml) and 1, 2-dichloroethane (4 ml) in a 100 ml round-bottom flask. 2, 2-dimethoxypropane (1 g, 5 eq) was added under stirring and the temperature was raised to 80° C. The reaction was monitored by TLC until it was completed. An aqueous solution of sodium carbonate and ethyl acetate were added for extraction, and the organic phase was dried over anhydrous sodium sulfate and separated by column chromatography to obtain 0.36 g of Example 8. LC-MS [M+1]=419. $^1$H NMR (400 MHz, $CDCl_3$) δ 8.14 (dd, J=7.7, 1.9 Hz, 2H), 7.07 (dt, J=7.9, 3.9 Hz, 1H), 7.01 (dd, J=7.4, 2.6 Hz, 1H), 6.33-6.21 (m, 2H), 5.58 (d, J=5.7 Hz, 1H), 3.98 (s, 3H), 1.72 (s, 3H), 1.62-1.55 (m, 6H).

Example 8

Synthetic Route:

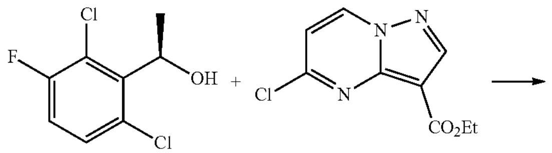

1 1'

-continued

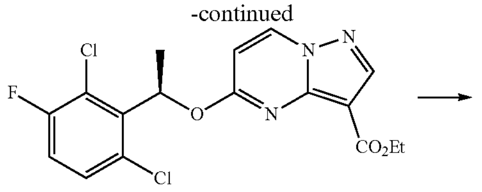

2

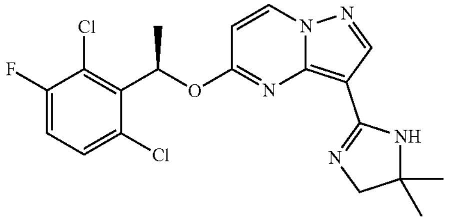

Example 8

Reaction Steps:

(1) Synthesis of compound 2: sodium tert-butoxide (0.07 g, 1.5 eq) was dissolved in 5 ml toluene, compound 1 (0.1 g, 1 eq) was added at 0° C., and compound 1' (ethyl 5-clopyrazolo [1,5-a] pyrimidin-3-carboxylate) (0.13 g, 1.2 eq) was added to the reaction system after 5 min. The temperature was gradually increased to rt to react for 2 h. TLC monitoring showed that the reaction was completed, quenched with ammonium chloride solution, extracted with EA and dried, samples were mixed and purified by column chromatography to obtain 0.1 g compound 2 in a yield of 50%.

Synthesis of compound Example 8: 1, 2-diamino-2-methylpropane (1.5 eq) was dissolved in dry toluene (3 ml). Trimethyl aluminum (5 eq) was added dropwise at 0° C. under the protection of Ar, and then the temperature was raised to RT to react for 2 h. Then compound 2 (0.1 g, 1 eq) in toluene (3 mL) was added dropwise at 0° C. After reaction for 30 min, the temperature was raised to 80° C. to react for 3 h. The reaction was monitored by TLC until it was completed. Quenched with methanol, adjusted pH to be 8-9, extracted with EA and dried, and 20 mg was obtained by separation on preparation plate with a yield of 20%. $^1H$ NMR (400 MHz, $CDCl_3$) δ 9.54 (s, 1H), 8.63 (d, J=7.5 Hz, 1H), 7.36-7.28 (m, 2H), 7.13 (dd, J=8.9, 7.9 Hz, 1H), 6.71 (d, J=7.5 Hz, 1H), 6.61 (q, J=6.8 Hz, 1H), 3.71 (dd, J=27.5, 10.7 Hz, 2H), 1.86 (d, J=6.9 Hz, 3H), 1.58 (d, J=4.4 Hz, 6H).

Example 9

Synthetic Route

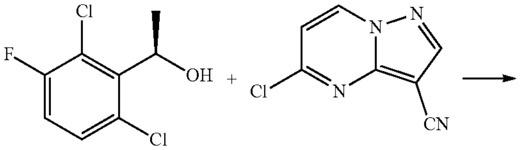

1 1'

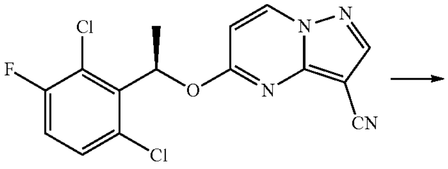

2

-continued

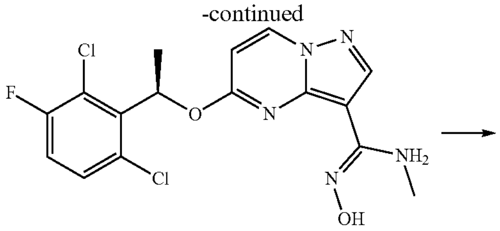

3

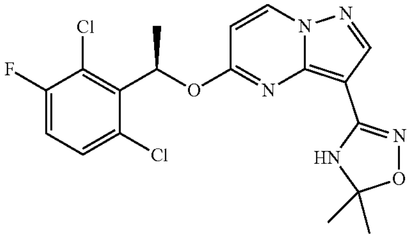

Example 9

Reaction Steps:

(1) Synthesis of compound 2: sodium tert-butoxide (0.35 g, 1.5 eq) was dissolved in 25 ml toluene, compound 1 (0.5 g, 1 eq) was added at 0° C., and compound 1' (0.51 g, 1.2 eq) was added to the reaction system after 5 min. The temperature was gradually increased to rt to react for 2 h. The reaction was monitored by TLC until it was completed. Quenched by ammonium chloride solution, extracted with EA and dried, samples were mixed and purified by column chromatography to obtain 0.7 g with a yield of 83%.

(2) Synthesis of compound 3: compound 2 (0.7 g, 1 eq), hydroxylamine hydrochloride (0.28 g, 2 eq) and potassium carbonate (0.56 g, 2 eq) were successively added into absolute ethanol (7 ml), and reacted overnight at 80° C. After the reaction was completed, water and EA were added for extraction and dried, samples were mixed and purified by column chromatography to obtain 0.3 g with a yield of 39.5%. LCMS (384.0, 386.0).

Synthesis of Compound Example 9: compound 3 (0.1 g, 1 eq) and 2, 2-dimethoxypropane (0.11 g, 4 eq) were added into acetic acid (4 ml) and reacted overnight at 50° C. After the reaction was completed, the mixture was basified with sodium bicarbonate solution, extracted with EA, dried, samples were mixed and purified by column chromatography to obtain 0.07 g with a yield of 63.6%. $^1H$ NMR (400 MHz, $CDCl_3$) δ 8.43 (d, J=7.5 Hz, 1H), 8.32 (s, 1H), 7.31-7.27 (m, 1H), 7.07 (dd, J=8.8, 8.0 Hz, 1H), 6.59 (q, J=6.9 Hz, 1H), 6.49 (d, J=7.5 Hz, 1H), 5.61 (s, 1H), 1.81 (d, J=6.9 Hz, 3H), 1.63 (s, 3H), 1.55 (s, 3H).

Example 10

Synthetic Route:

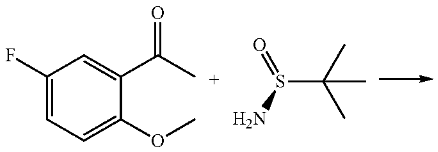

1

-continued

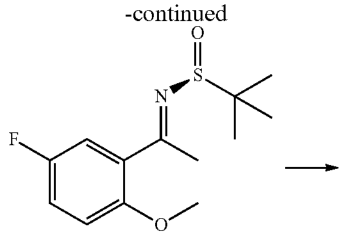

2

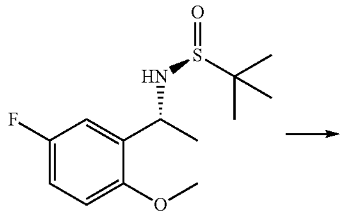

3

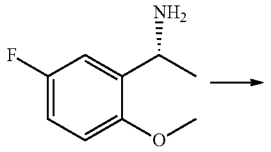

4

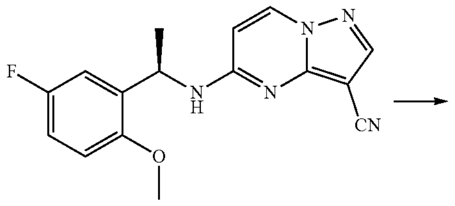

5

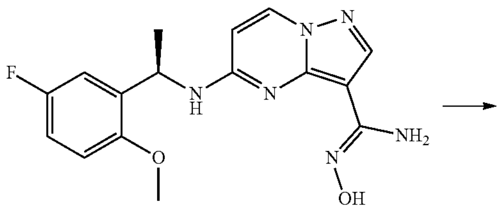

6

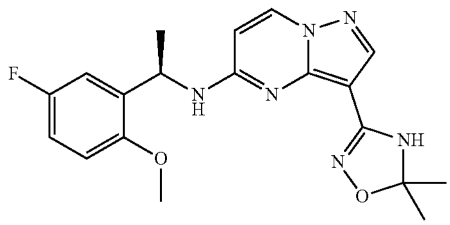

Example 10

Reaction Steps:

(1) Synthesis of compound 2: compound 1 (5 g, 1 eq) was dissolved in THF (50 ml), R-tert-butyl sulfinamide (7.25 g, 2 eq) was added, then tetraethyl titanate (13.75 g, 2 eq) was added to the reaction system, and reacted overnight at 60° C. The reaction was monitored by TLC until it was completed. The samples were mixed and purified by column chromatography (PE:EA=10:1-5:1) to obtain 4.3 g of compound 2 with a yield of 53.7%.

(2) Synthesis of compound 3: compound 2 (4.4 g, 1 eq) was dissolved in THF (35 ml), sodium borohydride (1.85 g, 3 eq) was added in batches at −50° C., and then the temperature was gradually raised to RT to react for 5 h. After the reaction was completed, water and EA were added for extraction, samples were mixed and purified by column chromatography to obtain 2.6 g+1 g compound 3 (containing its diastereomers) with a yield of 59.1%.

(3) Synthesis of compound 4: compound 3 (0.8 g, 1 eq) was added into 8 ml 4M dioxane hydrochloride, reacted for 4 h at RT. The reaction was monitored by TLC until it was completed. Sodium carbonate solution was added to adjust pH to be 9-10, extracted with EA, dried and evaporated to obtain 0.5 g of compound 4 with a yield of 98%.

(4) Synthesis of compound 5: compound 4 (0.5 g, 1 eq) was added into 15 ml absolute ethanol, followed by 5-clopyrazolo [1,5-a] pyrimidin-3-cyano (0.58 g, 1.1 eq) and triethylamine (0.9 g, 3 eq) and reacted overnight at 60° C. The reaction was monitored by TLC until it was completed. PE was added and filtered to obtain 0.4 g with a yield of 43.5%.

(5) Synthesis of compound 6: compound 5 (0.4 g, 1 eq), hydroxylamine hydrochloride (0.18 g, 2 eq) and potassium carbonate (0.36 g, 2 eq) were successively added into a mixture of absolute ethanol:dioxane=2:1 (15 ml), and reacted overnight at 80° C. After the reaction was completed, water and EA were added for extraction, dried, samples were mixed and purified by column chromatography to obtain 0.4 g with a yield of 91%.

Synthesis of compound Example 10: compound 6 (0.2 g, 1 eq) and 2,2-dimethoxypropane (0.25 g, 4 eq) were added into the mixed solvent (6 ml) of acetic acid: 1, 2-dichloroethane=1:1, and reacted at 80° C. for 2 h. After the reaction was completed, the mixture was basified with sodium bicarbonate solution, extracted with EA, dried, and the samples were mixed and purified by column chromatography to obtain 0.13 g with a yield of 59.1%. $^1$H NMR (400 MHz, $CDCl_3$) δ 8.19 (d, J=7.8 Hz, 2H), 6.92 (m, J=13.3, 8.8, 3.7 Hz, 3H), 6.09 (d, J=7.4 Hz, 1H), 5.87 (s, 1H), 5.47 (s, 1H), 5.29 (s, 1H), 3.91 (s, 3H), 1.62 (s, 3H), 1.56 (d, J=6.7 Hz, 6H).

Example 11

Synthetic Route:

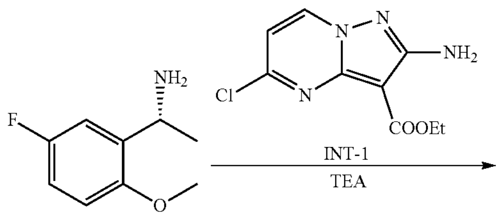

1

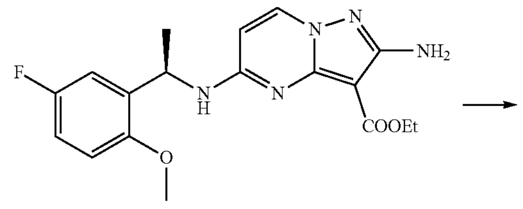

2

-continued

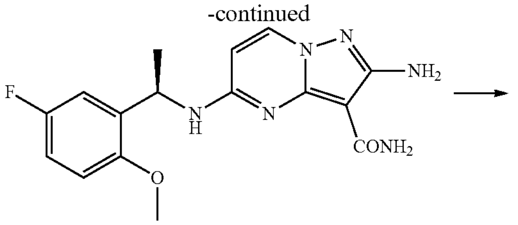

3

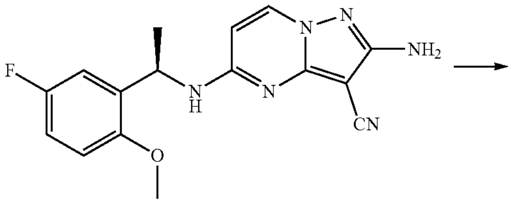

4

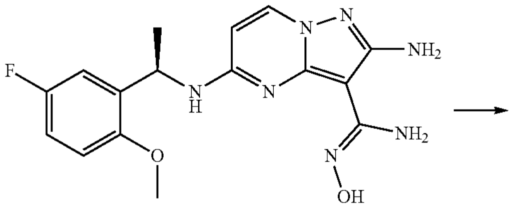

5

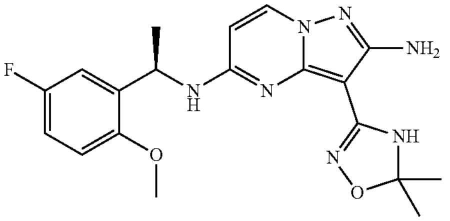

Example 11

Reaction Steps:

(1) Synthesis of compound 2: 10 ml of anhydrous ethanol was added to compound 1 (1.0 g, 1.5 eq), followed by INT-1 (947 mg, 1.0 eq) and TEA (1.6 ml, 3.0 eq), respectively. After replacing with nitrogen, the reaction was carried out at 60° C. for 18 h. TLC monitoring showed that the reaction was completed. Then the ethanol was evaporated. Then water (50 ml) was added to the reaction system, and EA (50 ml×3) was added for extraction. EA phases were combined, dried by adding anhydrous sodium sulfate, filtered, evaporated and purified by column chromatography to obtain 1.1 g of compound 2 (yield 86%).

(2) Synthesis of compound 3: 50 ml toluene was added into a 150 ml three-necked flask, cooled to −10-0° C., then blew ammonia into toluene until saturated. Trimethyl aluminum (12.4 ml, 4.5 eq) was added dropwise at 0° C., stirred at room temperature for 2 h after addition. Then cooled down to 0° C., compound 2 (1.1 g, 1.0 eq) in toluene was added dropwise, and the temperature was raised to 80° C. to react for 18 h after addition. After TLC monitoring showed that the reaction was completed, filtrated, washed the cake with EA, and the filtrate was collected. Water was added to the filtrate, the liquid was separated, the organic phase was collected, anhydrous sodium sulfate was added to dry, filtered, evaporated and purified by column chromatography to obtain 600 mg of compound 3 (yield 51%).

(3) Synthesis of compound 4: phosphorus oxychloride (10 ml) was added to compound 3 (600 mg, 1.0 eq), stirred at 80° C. for 5 h, and TLC monitoring showed that the reaction was completed. The phosphorus oxychloride was evaporated, then pH was adjusted to be 7-8 with sodium bicarbonate aqueous solution, then EA (40×3) was added for extraction, separation. EA phases were combined, anhydrous sodium sulfate was added for drying, filtrated, evaporated and purified by column chromatography to obtain 120 mg of compound 4 (yield 21%).

(4) Synthesis of compound 5: absolute ethanol (3 ml) and 1, 4-dioxane (3 ml) were added to compound 4 (80 mg, 1.0 eq), then hydroxylamine hydrochloride (42.6 mg, 2.0 eq) and potassium carbonate (85 mg, 2 eq) were added, and replaced with nitrogen gas, reacted at 80° C. for 16 h. TLC monitoring showed that the reaction was completed, filtered, evaporated and purified by column chromatography directly to obtain 70 mg of compound 5 (yield 79%).

Synthesis of Example 11: 1 ml of glacial acetic acid and 1, 2-dichloroethane (1 ml) were added to compound 5 (70 mg, 1.0 eq), then 2, 2-dimethoxypropane (81 mg, 4 eq) was added, and replaced with nitrogen gas, reacted at 80° C. for 1 h. TLC monitoring showed that the reaction was completed, the solvent was evaporated, then sodium bicarbonate aqueous solution was added to the system, pH was adjusted to be 7-8, then EA (10 ml×3) was added for extraction. EA phases were combined, anhydrous sodium sulfate was added for drying, filtered, evaporated and purified by column chromatography to obtain 15 mg (yield 19%). $^1H$ NMR (400 MHz, $CDCl_3$) δ 7.91 (d, J=7.4 Hz, 1H), 7.02-6.82 (m, 3H), 5.84 (d, J=7.3 Hz, 1H), 5.78 (s, 1H), 5.24-5.13 (m, 1H), 4.93 (s, 2H), 3.90 (s, 3H), 3.75 (t, J=6.7 Hz, 1H), 1.61 (s, 3H), 1.53 (d, J=6.7 Hz, 6H).

Example 12

Synthetic Route:

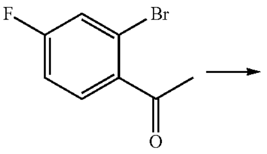

1

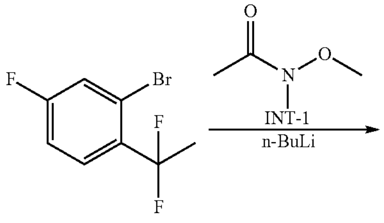

2

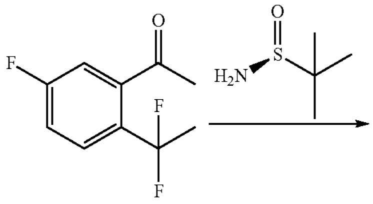

3

-continued

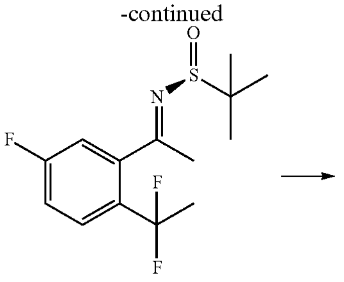

4

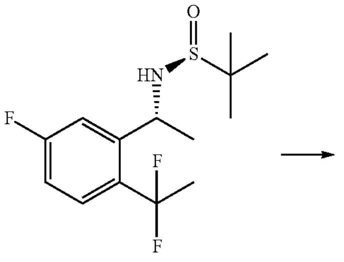

5

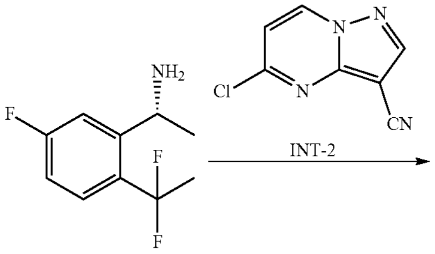

6

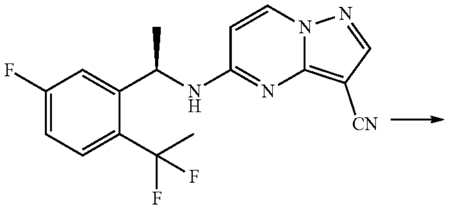

7

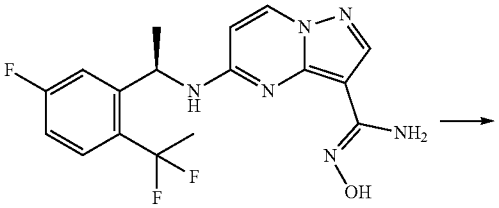

8

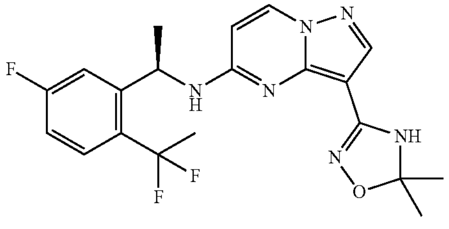

Example 12

Reaction Steps:

(1) Synthesis of compound 2: BAST (23 g, 1.5 eq) was added to compound 1 (15 g, 1.0 eq), replaced with nitrogen gas, and reacted at 70° C. for 18 h. The raw material monitored by TLC disappeared, then water (100 ml) was added to the reaction system, followed by ether (100 ml) for extraction, and the ether phase was collected, then 10% citric acid aqueous solution was added for washing and separation. Then sodium bicarbonate aqueous solution was added for washing and separation, and brine was added for washing once, then the organic phase was collected and dried, ether was evaporated at low temperature and purified by column chromatography using pure petroleum ether to obtain 9.6 g compound 2 (yield 58%).

(2) Synthesis of compound 3: anhydrous THF (50 ml) was added into compound 2 (5 g), cooled to −78° C., then n-BuLi (10.08 ml, 1.2 eq) was slowly added dropwise, stirred at low temperature for 1 h after addition. Then INT-1 (1.6 g, 1.2 eq) in THF was added dropwise, and reacted for 1 h at the temperature after addition. TLC monitoring showed that the reaction was completed, ammonium chloride aqueous solution was added to the reaction system for quenching, then EA was added for extraction. EA phase was collected, dried over anhydrous sodium sulfate, filtered, evaporated and purified by column chromatography to obtain 680 mg of compound 3 (yield 16%).

(3) Synthesis of compound 4: compound 3 (680 mg, 1.0 eq) was dissolved in anhydrous THF (8 ml), then R-tert-butyl sulfinamide (814.6 mg, 2 eq) was added, followed by tetraethyl titanate (1.56 g, 2 eq), and reacted at 60° C. for 2 h. TLC monitoring showed that the reaction was completed, the reaction solution was poured into water, solids were precipitated, filtered, the filtrate was collected, extracted with water and EA, the EA phase was collected, dried over anhydrous sodium sulfate, evaporated and purified by column chromatography to obtain 900 mg of compound 4 (yield 87%).

(4) Synthesis of compound 5: compound 4 (900 mg, 1.0 eq) was dissolved in THF (10 ml), cooled to −50° C., sodium borohydride (224 mg, 2 eq) was added in batches, and then gradually raised to room temperature for 2 h. TLC monitoring showed that the reaction was completed, water was added into the reaction system, then EA (30 ml×3) was added for extraction, EA phase was collected, anhydrous sodium sulfate was added for drying, and evaporated and purified by column chromatography to obtain 115 mg of compound 5 (yield 12.7%).

(5) Synthesis of compound 6: dioxane hydrochloride (2 ml) was added to compound 5 (115 mg, 1.0 eq), reacted at room temperature for 2 h. TLC monitoring showed that the reaction was completed, the solvent was removed. Saturated sodium bicarbonate aqueous solution was added to adjust pH to be 7-8, then dichloromethane and methanol were added for extraction for many times. Organic phases were collected, dried over anhydrous sodium sulfate, filtered and evaporated to obtain 80 mg compound 6 (yield 95%).

(6) Synthesis of compound 7: anhydrous ethanol (10 ml) was added into compound 6 (80 mg, 1.0 eq), followed by INT-2 (84 mg, 1.1 eq) and TEA (0.17 ml, 3.0 eq), respectively. After replacing with nitrogen, the reaction was carried out at 60° C. for 18 h. TLC monitoring showed that the reaction was completed, the ethanol was evaporated. Then water was added to the reaction system, and EA (10 ml×3) was added for extraction. EA phases were combined, dried by adding anhydrous sodium sulfate, filtered, evaporated and purified by column chromatography to obtain 120 mg of compound 7 (yield 88%).

(4) Synthesis of compound 8: absolute ethanol (1.2 ml) and 1, 4-dioxane (0.4 ml) were added to compound 4 (120 mg, 1.0 eq), then hydroxylamine hydrochloride (63.9 mg, 2.0 eq) and potassium carbonate (127.5 mg, 2.0 eq) were added, and replaced with nitrogen gas, reacted at 80° C. for 16 h. TLC monitoring showed that the reaction was completed, filtered, evaporated and purified by column chromatography directly to obtain 100 mg of compound 8 (yield 76%).

Synthesis of Example 12: glacial acetic acid (1 ml) and 1, 2-dichloroethane (1 ml) were added to compound 8 (100 mg, 1.0 eq), then 2, 2-dimethoxypropane (112 mg, 4 eq) was added, and replaced with nitrogen gas, reacted at 80° C. for 1 h. TLC monitoring showed that the reaction was completed, the solvent was evaporated, then sodium bicarbonate aqueous solution was added to the system, pH was adjusted to be 7-8, then EA (20 ml×3) was added for extraction. EA phases were combined, anhydrous sodium sulfate was added for drying, filtered, evaporated and purified by column chromatography to obtain 40 mg of Example 14 (yield 36%). $^{1}$H NMR (400 MHz, $CDCl_3$) δ 8.21 (d, J=7.6 Hz, 1H), 8.19 (s, 1H), 7.50 (d, J=7.0 Hz, 1H), 7.38 (s, 1H), 7.17-7.08 (m, 1H), 6.13 (d, J=7.6 Hz, 1H), 5.96 (s, 1H), 5.49 (s, 1H), 5.43 (s, 1H), 1.87 (t, J=18.2 Hz, 3H), 1.67-1.58 (m, 6H), 1.53 (s, 3H).

Example 13

Synthetic Route:

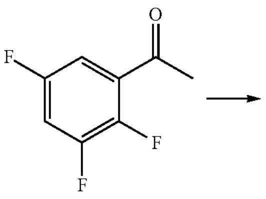

1

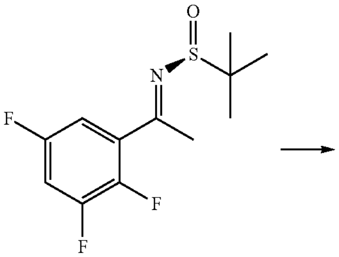

2

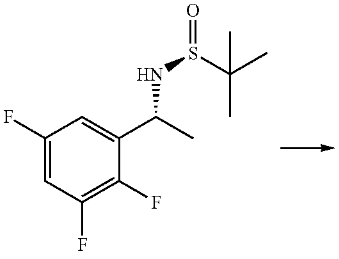

3

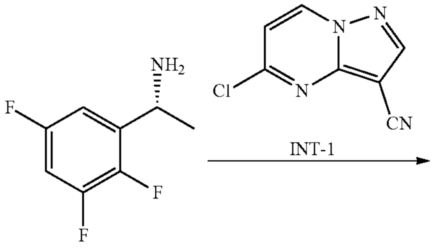

4

-continued

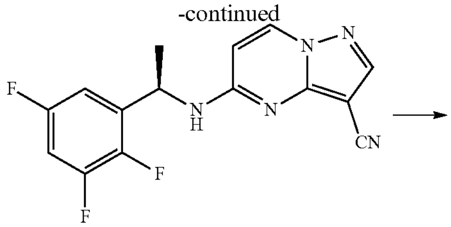

5

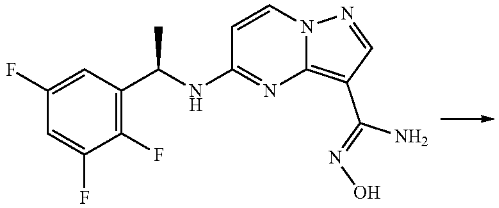

6

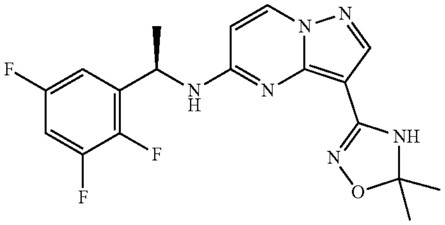

Example 13

Reaction Steps:

(1) Synthesis of compound 2: compound 1 (3 g, 1.0 eq) was dissolved in anhydrous THF (10 ml), then R-tert-butyl sulfinamide (4.17 g, 2.0 eq) was added, followed by tetraethyl titanate (7.86 g, 2.0 eq), and reacted at 60° C. for 2 h. TLC monitoring showed that the reaction was completed, the reaction solution was poured into water, solids were precipitated, filtered, the filtrate was collected, extracted with water and EA (150 mg×3). The EA phase was collected, dried over anhydrous sodium sulfate, evaporated and purified by column chromatography to obtain 3.8 g of compound 2 (yield 97%).

(2) Synthesis of compound 3: compound 2 (3.8 g, 1.0 eq) was dissolved in THF (40 ml), cooled to −50° C., sodium borohydride (1.04 g, 2.0 eq) was added in batches, and then gradually raised to room temperature to react for 2 h. TLC monitoring showed that the reaction was completed, water was added into the reaction system, then EA (100 ml×3) was added for extraction. EA phase was collected, anhydrous sodium sulfate was added for drying, and evaporated and purified by column chromatography to obtain 1.2 g of compound 3 (yield 31%).

(3) Synthesis of compound 4: dioxane hydrochloride was added into compound 3 (1.2 g, 1.0 eq), reacted at room temperature for 2 h. TLC monitoring showed that the reaction was completed, the solvent was removed. Saturated sodium bicarbonate aqueous solution was added to adjust pH to be 7-8, then dichloromethane and methanol were added for extraction for many times. Organic phases were collected, dried over anhydrous sodium sulfate, filtered and evaporated to obtain 700 mg compound 4 (yield 93%).

(4) Synthesis of compound 5: 10 ml of anhydrous ethanol was added into compound 4 (700 mg, 1.0 eq), followed by INT-1 (783 mg, 1.1 eq) and TEA (1.2 ml, 3.0 eq), respectively. After replacing with nitrogen, the reaction was carried out at 60° C. for 18 h. TLC monitoring showed that the reaction was completed. Then the ethanol was evaporated. Then water was added to the reaction system, and EA (50 ml×3) was added for extraction. EA phases were combined, dried by adding anhydrous sodium sulfate, filtered, evaporated and purified by column chromatography to obtain 900 mg of compound 5 (yield 71%).

(5) Synthesis of compound 6: absolute ethanol (8 ml) and 1, 4-dioxane (4 ml) were added to compound 5 (900 mg, 1.0 eq), then hydroxylamine hydrochloride (394.6 mg, 2.0 eq) and potassium carbonate (783.6 mg, 2.0 eq) were added, and replaced with nitrogen gas, reacted at 80° C. for 16 h. TLC monitoring showed that the reaction was completed, filtered, evaporated and purified by column chromatography directly to obtain 730 mg of compound 6 (yield 74%).

Synthesis of Example 13: glacial acetic acid (7 ml) and 1, 2-dichloroethane (7 ml) were added to compound 8 (700 mg, 1.0 eq), then 2, 2-dimethoxypropane (832 mg, 4.0 eq) was added, and replaced with nitrogen gas, reacted at 80° C. for 1 h. TLC monitoring showed that the reaction was completed, the solvent was evaporated, then sodium bicarbonate aqueous solution was added to the system, pH was adjusted to be 7-8, then EA (30 ml×3) was added for extraction. EA phases were combined, anhydrous sodium sulfate was added for drying, filtered, evaporated and purified by column chromatography to obtain 42 mg (yield 5%). $^1$H NMR (400 MHz, $CDCl_3$) δ 8.23 (d, J=7.6 Hz, 1H), 8.19 (s, 1H), 6.85 (dd, J=8.3, 4.9 Hz, 2H), 6.17 (d, J=7.6 Hz, 1H), 5.85 (s, 1H), 5.60 (d, J=5.6 Hz, 1H), 5.49-5.37 (m, 1H), 1.60 (d, J=7.0 Hz, 6H), 1.51 (s, 3H).

Example 14

Synthetic route:

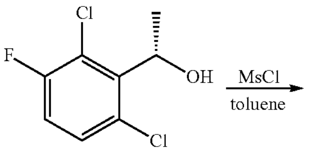

1

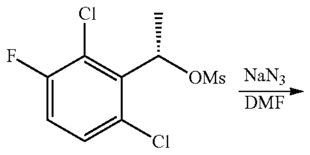

2

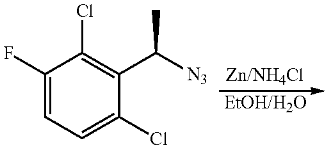

3

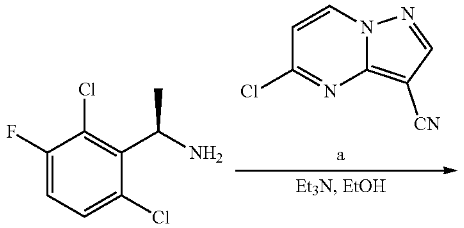

4

-continued

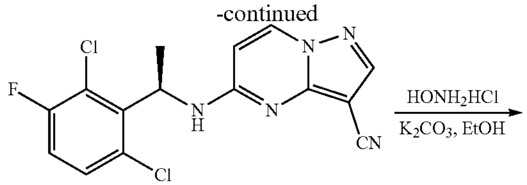

5

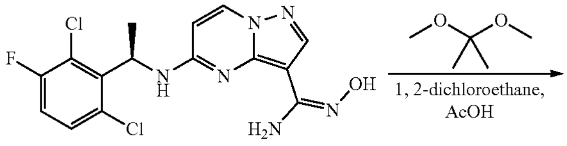

6

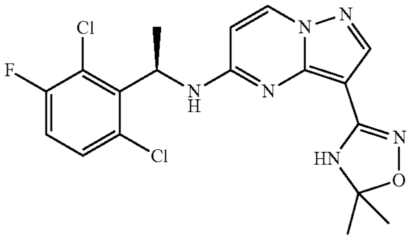

Example 14

Reaction Steps:

(1) Synthesis of compound 2: 10 g of compound 1 and MsCl (7.1 g, 1.3 eq) were dissolved in toluene solvent in a 250 mL round bottom flask, then triethylamine (7.3 g, 1.5 eq) was added as base, and reacted at room temperature for 4 hours, TLC monitoring showed that the reaction was completed. The organic phase was extracted, dried, evaporated and purified by column chromatography using petroleum ether:ethyl acetate (10:1) to obtain 13.1 g of pale yellow liquid compound 2.

(2) Synthesis of compound 3: compound 2 (13 g) was placed in a 100 ml round bottom flask, DMF (60 ml) was added as solvent, followed by $NaN_3$ (5.9 g, 2.0 eq), reacted at 50° C. for 3.5 hours, monitored by TLC until it was completed. Extracted with water and ethyl acetate, the organic phase was dried and evaporated. Purified by column chromatography using petroleum ether:ethyl acetate (10:1) to obtain 10.2 g of compound 3.

(3) Synthesis of compound 4: compound 3 (10.2 g) was placed in a 250 ml round bottom flask. Ethanol (102 ml) and water (34 ml) (3:1) were added as a mixed solvent, then Zn (3.7 g, 1.3 eq) and $NH_4Cl$ (5.85 g, 2.5 eq) were added, refluxed at 80° C. for 6 hours, the reaction was monitored and completed. The organic phase was filtered, extracted with ethyl acetate, dried and evaporated. Purified by column chromatography using petroleum ether:ethyl acetate (10:1) to obtain 7.3 g of compound 4.

(4) Synthesis of compound 5: compound 4 (1.5 g) was placed in a 100 ml round-bottom flask, followed by compound a (1.56 g, 1.2 eq), triethylamine (3 ml, 3 eq) and ethanol (50 ml) as solvent, refluxed, and the reaction was monitored and completed after about 2 hours. The small amount of ethanol was evaporated, water and ethyl acetate were added for extraction. Then purified by column chromatography using petroleum ether:ethyl acetate (3:1) to obtain 2.1 g of compound 5.

(5) Synthesis of compound 6: compound 5 (1.0 g) was placed in a 100 ml round-bottom flask, then hydroxylamine hydrochloride (1.12 g, 5.6 eq) and anhydrous potassium carbonate (2.2 g, 5.6 eq) were added, then ethanol (50 ml)

was added as solvent, and refluxed overnight at 80° C., and the reaction was monitored and completed. The small amount of ethanol was evaporated, water and ethyl acetate were added for extraction. Then purified by column chromatography using petroleum ether:ethyl acetate (3:1) to obtain 0.6 g of compound 6.

Synthesis of Example 14: compound 6 (0.2 g) was weighed in a 50 ml round bottom flask, followed by 2, 2-dimethoxypropane (0.22 g, 4 eq), 1, 2-dichloroethane (4 ml) and acetic acid (4 ml) as a mixed solvent, refluxed at 80° C. for 2 hours, and the reaction was monitored and completed. A small amount of water was added, and saturated sodium bicarbonate was added to neutralize acetic acid in the reaction system, then extracted with dichloromethane. Then purified by column chromatography using dichloromethane:methanol (30:1) to obtain 66 mg of the final compound. $^1$H NMR (400 MHz, DMSO) δ: 8.59 (d, J=6.0 Hz, 1H), 8.55 (d, J=7.6 Hz, 1H), 7.97 (s, 1H), 7.52 (brs, 1H), 7.40 (t, J=8.7 Hz, 1H), 6.51 (d, J=7.6 Hz, 1H), 5.65-5.59 (m, 1H), 1.59 (d, J=7.2 Hz, 3H), 1.48 (s, 3H), 1.39 (s, 3H).

Example 15

Synthetic Route:

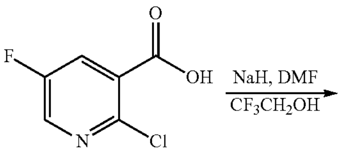

1

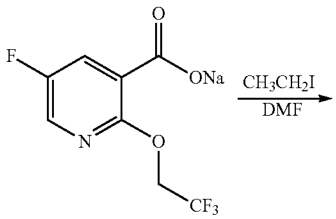

2

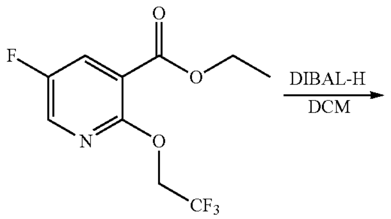

3

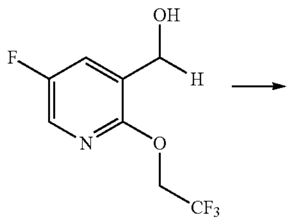

4

-continued

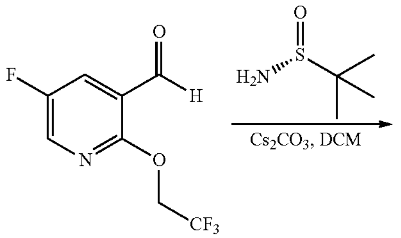

5

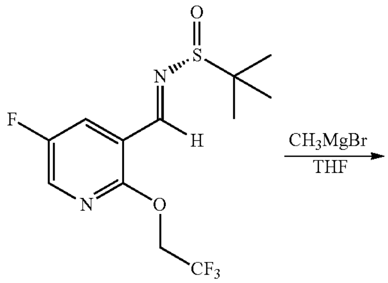

6

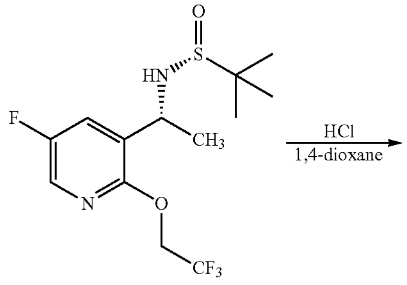

7

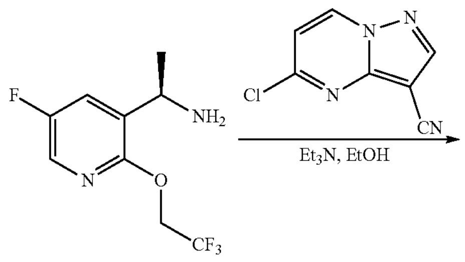

8

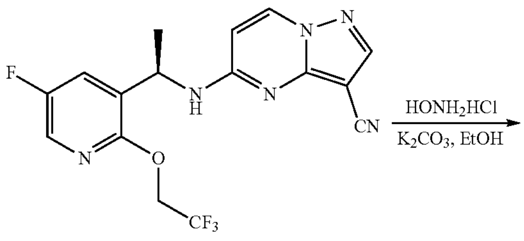

9

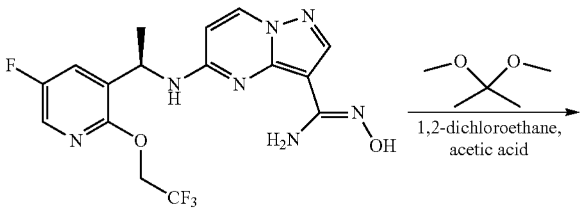

10

-continued

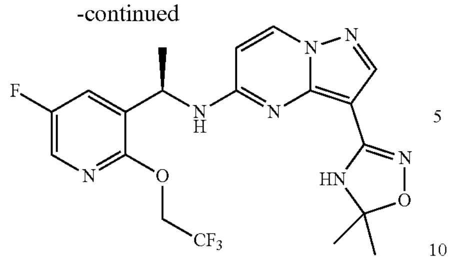

Example 15

Reaction Steps:

(1) Synthesis of compound 2: DMF (20 ml) as reaction solvent was added into a 100 ml round bottom flask, then the temperature was cooled to 0° C., NaH (1.71 g, 2.5 eq, 42.9 mmol) was slowly added, and the temperature was cooled for about 30 min after addition. 2-chloro-5-fluoronicotinic acid (3 g, 17.1 mmol) was added in batches, then the reaction was heated to room temperature to react for 4 hours, then raised to 75° C. overnight to obtain compound 2 which was used in the next step without further purification.

(2) Synthesis of compound 3: On the basis of compound 2, iodiethane (4.01 g, 1.5 eq, 25.7 mmol) was added dropwise, and then the reaction was stopped after half an hour. First, a large amount of DMF was removed by evaporation, and then extracted with ethyl acetate, dried over $Na_2SO_4$. The solvent was evaporated and purified by column chromatography using petroleum ether:ethyl acetate (20:1) to obtain 1.3 g of compound 3.

(3) Synthesis of compound 4: compound 3 (1.3 g, 4.87 mmol) was placed in a 100 mL three-neck flask, DCM (20 mL) was added as the solvent under nitrogen protection, then the temperature was cooled to −78° C. After stabilization, DIBAL-H (3.4 mL, 1.05 eq, 5.11 mmol) was added dropwise, and the temperature was kept at −78° C. for about 1 h. The reaction was monitored and completed. Water and methanol was added to quench the reaction to produce insoluble solid, a small amount of NaOH solution was added, and the solid was disappeared. The reaction was extracted with DCM, dried over $Na_2SO_4$. The solvent was evaporated and purified by column chromatography using petroleum ether:ethyl acetate (20:1) to obtain 0.63 g of compound 4.

(4) Synthesis of compound 5: compound 4 (0.63 g, 2.8 mmol) was placed in a 100 mL round bottom flask, ethyl acetate (10 mL) was added as solvent, then IBX (1.88 g, 2.4 eq, 6.72 mmol) was added and reacted at 80° C. The reaction was completed after about 2 hours. Then the reaction was suction filtered by a sand core funnel, washed with ethyl acetate. Filtrate was collected, and concentrated by evaporation to obtain 0.35 g of compound 5. The molecular weight of mass spectrum peak produced by liquid mass was 18 more than that of the compound, which meant binding one water and did not affect the next reaction.

(5) Synthesis of compound 6: compound 5 (0.35 g, 1.57 mmol) was added into a 100 ml round-bottom flask, then (R)-tert-butyl sulfinamide (0.29 g, 1.5 eq, 2.35 mmol) and cesium carbonate (0.36 g, 0.7 eq, 1.1 mmol) were weighed into the round-bottom flask, dichloromethane (10 mL) was added as reaction solvent, reacted at room temperature for about 2 h. The reaction was completed after about 2 hours, dichloromethane was added for extraction, and dried over $Na_2SO_4$. The solvent was evaporated and purified by column chromatography using petroleum ether:ethyl acetate (10:1) to obtain 0.6 g of compound 6.

(6) Synthesis of compound 7: compound 6 (0.6 g, 1.84 mmol) was placed in a 100 mL three-neck flask, anhydrous THF (10 mL) was added as the reaction solvent, and the temperature was cooled to −20° C. under nitrogen protection. After the temperature was constant, magnesium methyl bromide (2.2 mL, 1.2 eq, 2.21 mmol) in tetrahydrofuran was slowly added dropwise, and then the temperature was increased to react. After overnight reaction, there was a large amount of raw material remaining, and then methylmagnesium bromide in tetrahydrofuran solution (2.2 mL) was added. After the temperature returned to room temperature, the reaction was monitored and completed. Saturated ammonium chloride aqueous solution was added to quench the reaction. Then extracted with ethyl acetate, dried over $Na_2SO_4$. The solvent was evaporated and purified by column chromatography using petroleum ether:ethyl acetate (1.5:1) to obtain 0.2 g of compound 7.

(7) Synthesis of compound 8: compound 7 (0.2 g, 0.3 mmol) was added into a 50 mL round bottom flask, HCl/1, 4-dioxane (3 mL) and methanol (3 mL) were added. The reaction was completed at room temperature for about 1 h, and $NaHCO_3$ solution was added to neutralize the reaction, then ethyl acetate was added for extraction, dried over $Na_2SO_4$. The solvent was evaporated to obtain 0.1 g of compound 8.

(8) Synthesis of compound 9: compound 8 (0.1 g, 0.42 mmol) was placed in a 50 mL round bottom flask, followed by chlorocyanate (90 mg, 1.2 eq, 0.51 mmol), triethylamine (0.13 g, 3 eq) and ethanol (10 mL) as solvent, refluxed, and the reaction was monitored and completed after about 2 hours. The small amount of ethanol was evaporated, water and ethyl acetate were added for extraction. Then purified by column chromatography using petroleum ether:ethyl acetate (3:1) to obtain 55 mg of compound 9.

(9) Synthesis of compound 10: compound 9 (55 mg, 0.15 mmol) was placed in a 50 ml round-bottom flask, followed by hydroxylamine hydrochloride (56 mg, 5.6 eq) and anhydrous potassium carbonate (113 mg, 5.6 eq), then ethanol (5 ml) was added as solvent, and refluxed at 80° C., and the reaction was monitored and completed. The small amount of ethanol was evaporated, water and ethyl acetate were added for extraction. Then purified by column chromatography using petroleum ether:ethyl acetate (3:1) to obtain 41 mg of compound 10.

(10) Synthesis of Example 15: compound 10 (41 mg, 0.1 mmol) was placed in a 50 ml round bottom flask, followed by 2, 2-dimethoxypropane (61.95 mg, 6 eq, 0.6 mmol), 1, 2-dichloroethane (2 mL) and acetic acid (2 mL) as a mixed solvent, refluxed at 80° C. for 2 hours, and the reaction was monitored and completed. A small amount of water was added, and saturated sodium bicarbonate was added to neutralize acetic acid in the reaction system, then extracted with dichloromethane. Then purified by column chromatography using dichloromethane:methanol (30:1) to obtain 15 mg of the final compound.

Example 16

Synthetic Route:

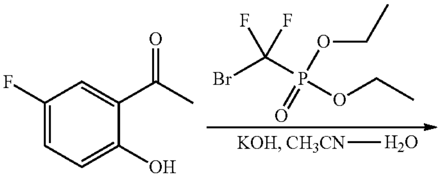

1

-continued

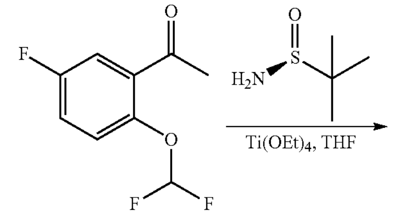

2

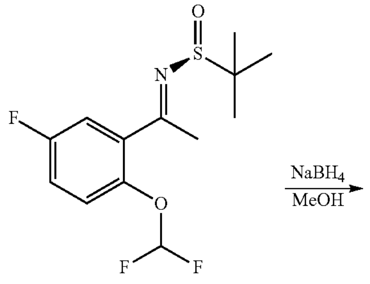

3

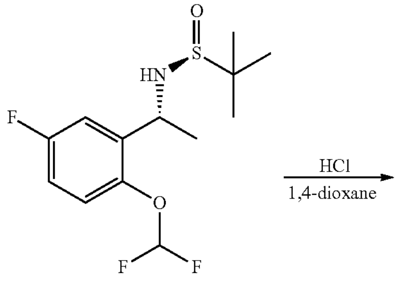

4

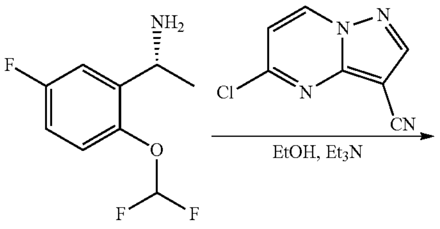

5

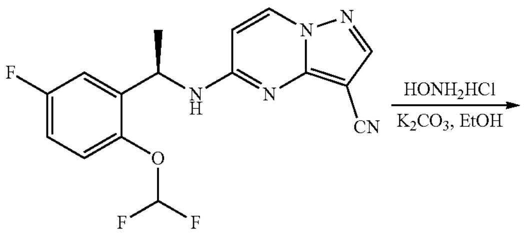

6

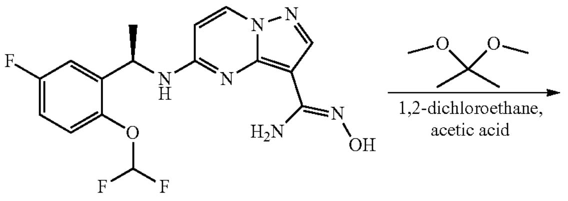

7

-continued

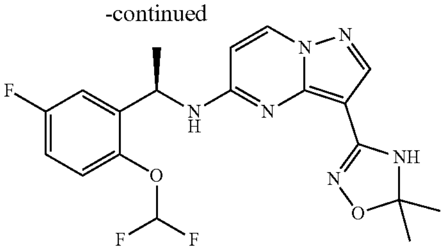

Example 16

Reaction Steps:

(1) Synthesis of compound 2: compound 1 (5 g, 32.5 mmol) was added into a 250 mL three-neck flask. A mixture of acetonitrile and water (1:1) (100 mL) was added as the reaction solvent. The temperature was cooled to −78° C. under nitrogen protection. During the cooling process, the reaction system was frozen to one piece at −50° C. Then diethyl bromofluoromethyl phosphonate (17.3 g, 2 eq, 65 mmol) was slowly added dropwise. The temperature was raised to room temperature after addition, and stirred for about 4 hours. After the reaction was monitored and completed, ethyl acetate was added for extraction, dried over $Na_2SO_4$. The solvent was evaporated and purified by column chromatography using petroleum ether:ethyl acetate (19:1) to obtain 5.6 g of compound 2 which had no mass spectrum absorption peak.

(2) Synthesis of compound 3: compound 2 (3.04 g, 14.9 mmol) was added into a 100 mL round bottom flask, and (R)-tert-butyl sulfinamide (3.62 g, 2 eq, 29.8 mmol) and tetraethyl titanate (8.5 g, 2.5 eq, 37.3 mmol) were added. Anhydrous THF (20 mL) was used as reaction solvent, and reaction was carried out at 80° C. for about 4 hours. After the reaction was monitored and completed, a large amount of solid was produced in the reaction system after adding water, filtered through Celite and washed, then extracted with ethyl acetate, dried over $Na_2SO_4$. The solvent was evaporated and purified by column chromatography using petroleum ether: ethyl acetate (4:1) to obtain 4.827 g of compound 3.

(3) Synthesis of compound 4: compound 3 (4.827 g, 15.7 mmol) was added into a 100 mL round bottom flask, anhydrous methanol (10 mL) was used as the solvent, and sodium borohydride (1.487 g, 2.5 eq, 39.3 mmol) was slowly added under ice bath. The temperature was raised and stirred for 30 min after addition. Water and ethyl acetate were slowly added for extraction after the reaction was completed, dried over $Na_2SO_4$. The solvent was evaporated and purified by column chromatography using petroleum ether:ethyl acetate (1.5:1) to obtain 1.82 g of compound 4.

(4) Synthesis of compound 5: compound 4 (1.82 g, 0.3 mmol) was added into a 100 mL round bottom flask, HCl/1, 4-dioxane (5 mL) and methanol (5 mL) were added. The reaction was completed at room temperature for about 1 h, and $NaHCO_3$ solution was added to neutralize the reaction, then ethyl acetate was added for extraction, dried over $Na_2SO_4$. The solvent was evaporated to obtain 1.4 g of compound 6.

(5) Synthesis of compound 6: compound 5 (0.5 g, 2.44 mmol) was placed in a 50 mL round bottom flask, followed by chlorocyanate (0.52 g, 1.2 eq, 2.93 mmol), triethylamine (0.65 mL, 2 eq) and ethanol (10 mL) as solvent, refluxed, and the reaction was monitored and completed after about 2 hours. The small amount of ethanol was evaporated, water and ethyl acetate were added for extraction. Then purified by column chromatography using petroleum ether:ethyl acetate (3:1) to obtain 0.53 g of compound 6.

(6) Synthesis of compound 7: compound 6 (0.53 g, 1.53 mmol) was placed in a 50 ml round-bottom flask, followed by hydroxylamine hydrochloride (0.59 g, 5.6 eq) and anhydrous potassium carbonate (1.18 g, 5.6 eq), then ethanol (10 ml) was added as solvent, and refluxed at 80° C., and the reaction was monitored and completed. The small amount of ethanol was evaporated, water and ethyl acetate were added for extraction. Then purified by column chromatography using dichloromethane:methanol (30:1) to obtain 420 mg of compound 7.

Synthesis of Example 16: compound 7 (420 mg, 1.1 mmol) was placed in a 50 ml round bottom flask, followed by 2, 2-dimethoxypropane (0.46 g, 4 eq, 4.44 mmol), 1, 2-dichloroethane (3 mL) and acetic acid (3 mL) as a mixed solvent, refluxed at 80° C., and the reaction was monitored and completed. A small amount of water was added, and saturated sodium bicarbonate was added to neutralize acetic acid in the reaction system, then extracted with dichloromethane. Then purified by column chromatography using dichloromethane:methanol (30:1) to obtain 26 mg of the final compound.

Examples 1-16 are summarized in Table 1-1 below:

TABLE 1-1

| Serial number | Structural formula | Characterization data of compounds (MS/HNMR) |
|---|---|---|
| Example 1 | 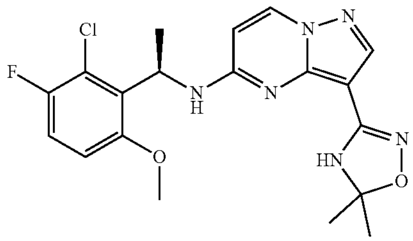<br>Example 1 | $^1$H NMR (400 MHz, $CDCl_3$) δ 8.25-8.12 (m, 2H), 7.05 (dd, J = 9.1, 8.2 Hz, 1H), 6.80 (dd, J = 9.1, 4.0 Hz, 1H), 6.08 (t, J = 30.1 Hz, 4H), 3.91 (s, 2H), 1.58 (t, J = 5.8 Hz, 8H). |
| Example 2 | 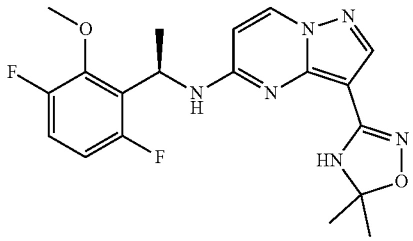<br>Example 2 | $^1$H NMR (400 MHz, $CDCl_3$) δ 8.20 (s, 1H), 8.15 (d, J = 7.6 Hz, 1H), 6.97 (ddd, J = 10.8, 9.2, 5.3 Hz, 1H), 6.75 (td, J = 9.4, 3.7 Hz, 1H), 6.34 (s, 1H), 6.06 (d, J = 7.5 Hz, 1H), 5.79-5.59 (m, 2H), 4.03 (d, J = 1.8 Hz, 2H), 1.72-1.64 (m, 5H), 1.60 (s, 3H). |
| Example 3 | 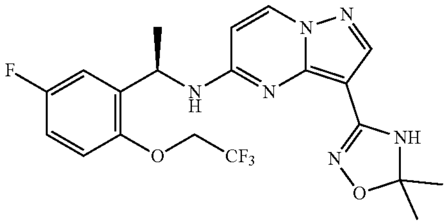<br>Example 3 | $^1$H NMR (400 MHz, $CDCl_3$) δ 8.29-8.10 (m, 2H), 7.03 (dd, J = 8.6, 2.9 Hz, 1H), 7.00-6.92 (m, 1H), 6.83 (dd, J = 9.0, 4.2 Hz, 1H), 6.08 (d, J = 7.6 Hz, 1H), 5.79 (s, 1H), 5.51 (d, J = 5.5 Hz, 1H), 5.25 (s, 1H), 4.53-4.29 (m, 2H), 1.62 (s, 3H), 1.59 (s, 3H), 1.47 (s, 3H). |
| Example 4 | 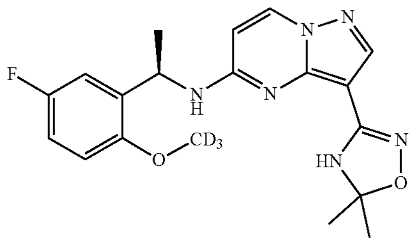<br>Example 4 | $^1$H NMR (400 MHz, $CDCl_3$) δ 8.17 (d, J = 7.6 Hz, 1H), 8.15 (s, 1H), 6.98 (dd, J = 8.8, 3.3 Hz, 1H), 6.95-6.88 (m, 1H), 6.86 (dd, J = 8.8, 4.4 Hz, 1H), 6.17 (d, J = 6.4 Hz, 1H), 5.95 (s, 1H), 5.86 (d, J = 5.4 Hz, 1H), 1.62 (s, 3H), 1.54 (d, J = 6.9 Hz, 3H), 1.44 (s, 3H). |

TABLE 1-1-continued

| Serial number | Structural formula | Characterization data of compounds (MS/HNMR) |
|---|---|---|
| Example 5 | 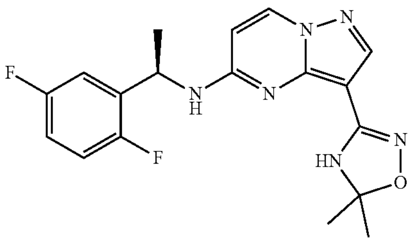 Example 5 | $^1$H NMR (400 MHz, $CDCl_3$) δ 8.21 (d, J = 7.6 Hz, 1H), 8.18 (s, 1H), 7.09-6.99 (m, 2H), 6.92 (m, 1H), 6.16 (d, J = 7.6 Hz, 1H), 5.94 (s, 1H), 5.55 (d, J = 5.7 Hz, 1H), 5.38 (m, 1H), 1.64 (s, 3H), 1.60 (s, 3H), 1.50 (s, 3H), MS: 373 (M + H +). |
| Example 6 | 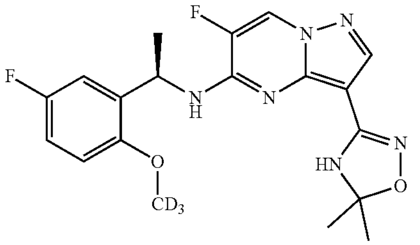 Example 6 | $^1$H NMR (400 MHz, $CDCl_3$) δ 8.27 (d, J = 5.6 Hz, 1H), 8.18 (s, 1H), 6.94 (m, 2H), 6.88 (m, 1H), 5.87 (d, J = 6.0 Hz, 1H), 5.71 (s, 1H), 5.36 (m, 1H), 1.62 (m, 6H), 1.44 (s, 3H). |
| Example 7 | 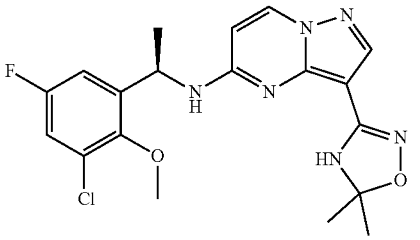 Example 7 | $^1$H NMR (400 MHz, $CDCl_3$) δ 8.14 (dd, J = 7.7, 1.9 Hz, 2H), 7.07 (dt, J = 7.9, 3.9 Hz, 1H), 7.01 (dd, J = 7.4, 2.6 Hz, 1H), 6.33-6.21 (m, 2H), 5.58 (d, J = 5.7 Hz, 1H), 3.98 (s, 3H), 1.72 (s, 3H), 1.62-1.55 (m, 6H). |
| Example 8 | 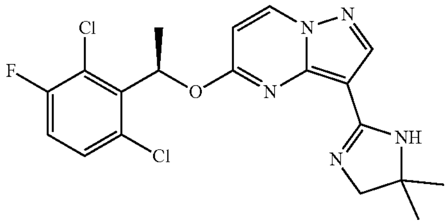 Example 8 | $^1$H NMR (400 MHz, $CDCl_3$) δ 9.54 (s, 1H), 8.63 (d, J = 7.5 Hz, 1H), 7.36-7.28 (m, 2H), 7.13 (dd, J = 8.9, 7.9 Hz, 1H), 6.71 (d, J = 7.5 Hz, 1H), 6.61 (q, J = 6.8 Hz, 1H), 3.71 (dd, J = 27.5, 10.7 Hz, 2H), 1.86 (d, J = 6.9 Hz, 3H), 1.58 (d, J = 4.4 Hz, 6H). |
| Example 9 | 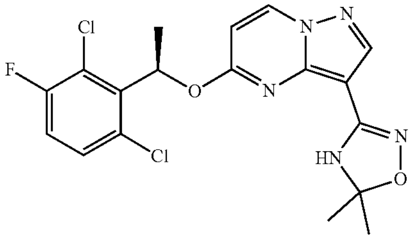 Example 9 | $^1$H NMR (400 MHz, $CDCl_3$) δ 8.43 (d, J = 7.5 Hz, 1H), 8.32 (s, 1H), 7.31-7.27 (m, 1H), 7.07 (dd, J = 8.8, 8.0 Hz, 1H), 6.59 (q, J = 6.9 Hz, 1H), 6.49 (d, J = 7.5 Hz, 1H), 5.61 (s, 1H), 1.81 (d, J = 6.9 Hz, 3H), 1.63 (s, 3H), 1.55 (s, 3H). |

TABLE 1-1-continued

| Serial number | Structural formula | Characterization data of compounds (MS/HNMR) |
| --- | --- | --- |
| Example 10 | 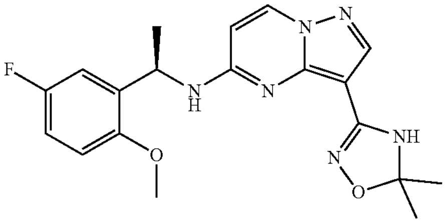 Example 10 | $^1$H NMR (400 MHz, $CDCl_3$) δ 8.19 (d, J = 7.8 Hz, 2H), 6.92 (m, J = 13.3, 8.8, 3.7 Hz, 3H), 6.09 (d, J = 7.4 Hz, 1H), 5.87 (s, 1H), 5.47 (s, 1H), 5.29 (s, 1H), 3.91 (s, 3H), 1.62 (s, 3H), 1.56 (d, J = 6.7 Hz, 6H). |
| Example 11 | 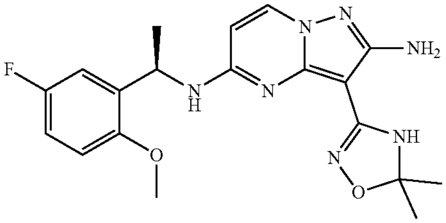 Example 11 | $^1$H NMR (400 MHz, $CDCl_3$) δ 7.91 (d, J = 7.4 Hz, 1H), 7.02-6.82 (m, 3H), 5.84 (d, J = 7.3 Hz, 1H), 5.78 (s, 1H), 5.24-5.13 (m, 1H), 4.93 (s, 2H), 3.90 (s, 3H), 3.75 (t, J = 6.7 Hz, 1H), 1.61 (s, 3H), 1.53 (d, J = 6.7 Hz, 6H). |
| Example 12 | 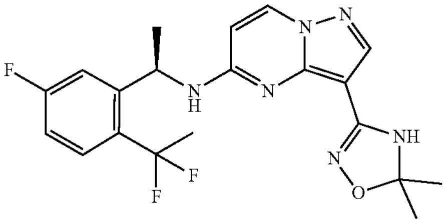 Example 12 | $^1$H NMR (400 MHz, $CDCl_3$) δ 8.21 (d, J = 7.6 Hz, 1H), 8.19 (s, 1H), 7.50 (d, J = 7.0 Hz, 1H), 7.38 (s, 1H), 7.17-7.08 (m, 1H), 6.13 (d, J = 7.6 Hz, 1H), 5.96 (s, 1H), 5.49 (s, 1H), 5.43 (s, 1H), 1.87 (t, J = 18.2 Hz, 3H), 1.67-1.58 (m, 6H), 1.53 (s, 3H). |
| Example 13 | 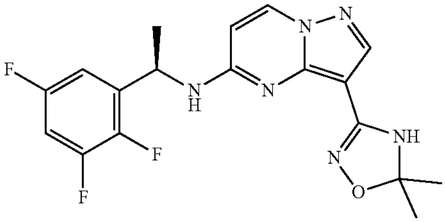 Example 13 | $^1$H NMR (400 MHz, $CDCl_3$) δ 8.23 (d, J = 7.6 Hz, 1H), 8.19 (s, 1H), 6.85 (dd, J = 8.3, 4.9 Hz, 2H), 6.17 (d, J = 7.6 Hz, 1H), 5.85 (s, 1H), 5.60 (d, J = 5.6 Hz, 1H), 5.49-5.37 (m, 1H), 1.60 (d, J = 7.0 Hz, 6H), 1.51 (s, 3H). |
| Example 14 | 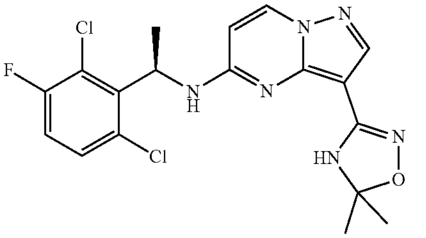 Example 14 | $^1$H NMR (400 MHz, DMSO) δ: 8.59 (d, J = 6.0 Hz, 1H), 8.55(d, J = 7.6 Hz, 1H), 7.97 (s, 1H), 7.52 (brs, 1H), 7.40 (t, J = 8.7 Hz, 1H), 6.51 (d, J = 7.6 Hz, 1H), 5.65-5.59 (m, 1H), 1.59 (d, J = 7.2 Hz, 3H), 1.48 (s, 3H), 1.39 (s, 3H). |

TABLE 1-1-continued

| Serial number | Structural formula | Characterization data of compounds (MS/HNMR) |
| --- | --- | --- |
| Example 15 | 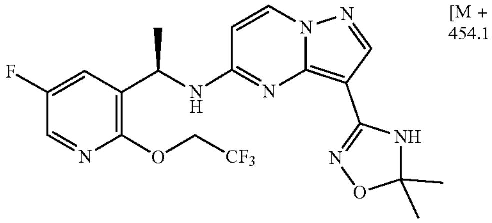 Example 15 | $[M+H]^+$ 454.1 |
| Example 16 | 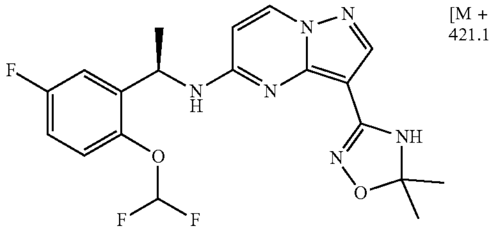 Example 16 | $[M+H]^+$ 421.1 |

Meanwhile, with reference to the above examples, examples 17-83 were synthesized, as detailed in Table 1-2:

TABLE 1-2

| Example | Structural formula of compound | Characterization data of compounds (MS/HNMR) |
| --- | --- | --- |
| 17 | 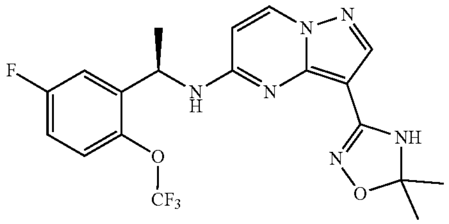 [SMILES: C[C@@H](Nc1ccn2ncc(C3=NOC(C)(C)N3)c2n1)c1cc(F)ccc1OC(F)(F)F] | $^1$H NMR (400 MHz, $CDCl_3$) δ 8.30-8.16 (m, 2H), 7.32-7.23 (m, 1H), 7.12 (dd, J = 8.8, 3.1 Hz, 1H), 7.00 (ddd, J = 9.0, 7.5, 3.1 Hz, 1H), 6.12 (d, J = 7.6 Hz, 1H), 5.74 (s, 1H), 5.38 (m,, 2H), 1.60 (m, 3H), 1.57 (m, 6H). |
| 18 | 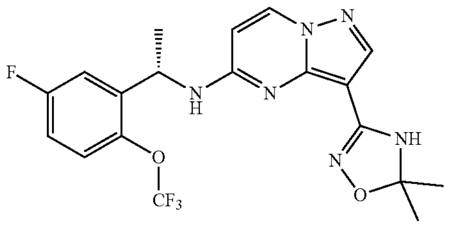 [SMILES: C[C@H](Nc1ccn2ncc(C3=NOC(C)(C)N3)c2n1)c1cc(F)ccc1OC(F)(F)F] | $^1$H NMR (400 MHz, $CDCl_3$) δ 8.28-8.11 (m, 2H), 7.27 (m, 1H), 7.12 (dd, J = 8.8, 3.0 Hz, 1H), 7.06-6.96 (m, 1H), 6.13 (d, J = 7.6 Hz, 1H), 5.75 (s, 1H), 5.46 (m, 1H), 5.37 (s, 1H), 1.69-1.53 (m, 9H). |
| 19 | 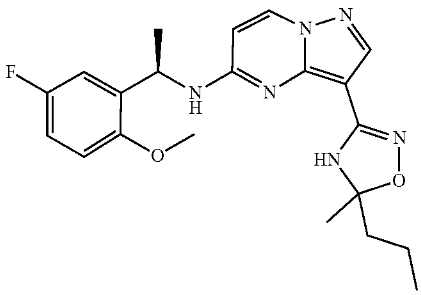 [SMILES: CCCC1(C)NC(c2cnn3ccc(N[C@H](C)c4cc(F)ccc4OC)nc23)=NO1] | $^1$H NMR (400 MHz, $CDCl_3$) δ 8.18 (dd, J = 7.6, 1.1 Hz, 1H), 8.16 (s, 1H), 6.99-6.94 (m, 1H), 6.91 (dd, J = 7.8, 3.0 Hz, 1H), 6.86 (dd, J = 8.9, 4.4 Hz, 1H), 6.12 (d, J = 6.9 Hz, 1H), 5.88 (s, 1H), 5.66 (d, J = 6.5 Hz, 1H), 3.90 (d, J = 2.8 Hz, 3H), 1.64 (m, 2H), 1.55 (m, 6H), 1.41 (m, 2H), 1.00 (t, J = 7.4 Hz, 3H). |

TABLE 1-2-continued

| Example | Structural formula of compound | Characterization data of compounds (MS/HNMR) |
|---|---|---|
| 20 | 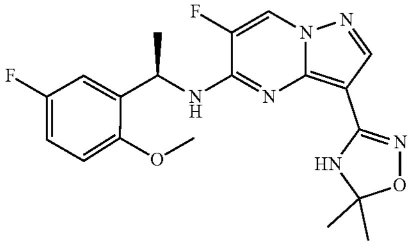 [SMILES: COc1ccc(F)cc1[C@@H](C)Nc1nc2c(C3=NOC(C)(C)N3)cnn2cc1F] | $^1$H NMR (400 MHz, $CDCl_3$) δ 8.27 (d, J = 5.6 Hz, 1H), 8.19 (s, 1H), 6.98-6.91 (m, 2H), 6.91-6.85 (m, 1H), 5.85 (d, J = 6.0 Hz, 1H), 5.71 (s, 1H), 5.36 (p, J = 6.8 Hz, 1H), 3.91 (s, 3H), 1.62 (m, 6H), 1.44 (s, 3H). |
| 21 | 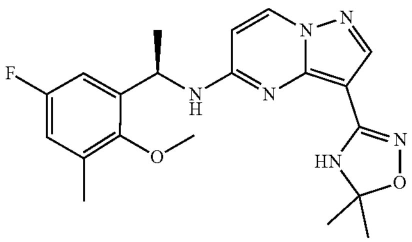 [SMILES: COc1c(C)cc(F)cc1[C@@H](C)Nc1ccn2ncc(C3=NOC(C)(C)N3)c2n1] | $^1$H NMR (400 MHz, $CDCl_3$) δ 8.18 (s, 1H), 8.16 (d, J = 7.6 Hz, 1H), 6.85 (dd, J = 8.8, 3.2 Hz, 1H), 6.79 (dd, J = 8.8, 3.2 Hz, 1H), 6.26 (s, 1H), 6.11 (d, J = 7.6 Hz, 1H), 5.61 (d, J = 6.8 Hz, 1H), 3.85 (s, 3H), 2.32 (s, 3H), 1.67 (s, 3H), 1.59 (d, J = 6.8 Hz, 3H), 1.57 (s, 3H) |
| 22 | 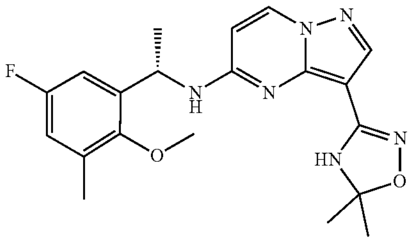 [SMILES: COc1c(C)cc(F)cc1[C@H](C)Nc1ccn2ncc(C3=NOC(C)(C)N3)c2n1] | $^1$H NMR (400 MHz, $CDCl_3$) δ 8.17 (s, 1H), 8.14 (d, J = 7.6 Hz, 1H), 6.87 (dd, J = 8.8, 3.2 Hz, 1H), 6.78 (dd, J = 8.8, 3.2 Hz, 1H), 6.31 (s, 1H), 6.14 (d, J = 7.6 Hz, 1H), 5.80 (d, J = 6.8 Hz, 1H), 5.54 (s, 1H), 3.85 (s, 3H), 2.32 (s, 3H), 1.68 (s, 3H), 1.59 (d, J = 7.2 Hz, 6H). |
| 23 | 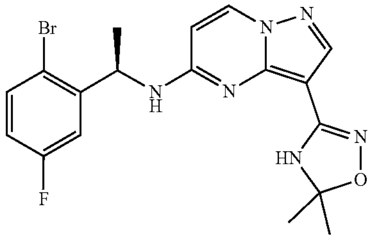 [SMILES: C[C@@H](Nc1ccn2ncc(C3=NOC(C)(C)N3)c2n1)c1cc(F)ccc1Br] | $^1$H NMR (400 MHz, $CDCl_3$) δ 8.21 (d, J = 7.6 Hz, 1H), 8.16 (s, 1H), 7.53 (dd, J = 8.8, 5.2 Hz, 1H), 7.13 (dd, J = 9.2, 3.2 Hz, 1H), 6.86 (m, 1H), 6.28 (d, J = 7.2 Hz, 1H), 6.12 (d, J = 4.8 Hz, 1H), 5.79 (s, 1H), 5.39-5.28 (m, 1H), 1.65 (s, 3H), 1.55 (d, J = 6.8 Hz, 3H), 1.43 (s, 3H). |
| 24 | 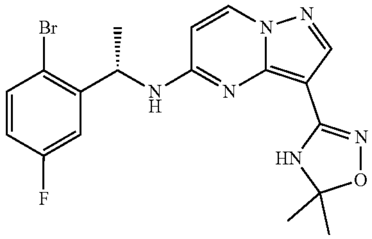 [SMILES: C[C@H](Nc1ccn2ncc(C3=NOC(C)(C)N3)c2n1)c1cc(F)ccc1Br] | $^1$H NMR (400 MHz, $CDCl_3$) δ 8.23 (d, J = 7.6 Hz, 1H), 8.18 (s, 7.54 (dd, J = 8.8, 5.2 Hz, 1H), 7.10 (dd, J = 9.2, 3.2 Hz, 1H), 6.87 (m, 1H), 6.21 (d, J = 6.8 Hz, 1H), 5.71 (d, J = 6.4 Hz, 2H), 5.34 (s, 1H), 1.65 (s, 3H), 1.56 (d, J = 6.8 Hz, 4H), 1.43 (s, 3H). |
| 25 | 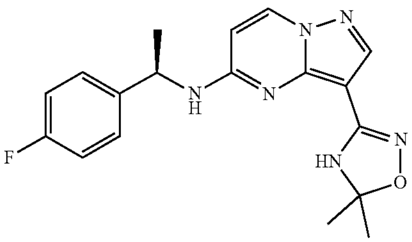 [SMILES: C[C@@H](Nc1ccn2ncc(C3=NOC(C)(C)N3)c2n1)c1ccc(F)cc1] | $^1$H NMR (400 MHz, $CDCl_3$) δ 8.19 (d, J = 7.6 Hz, 1H), 8.16 (s, 1H), 7.32 (dd, J = 8.8, 5.2 Hz, 2H), 7.04 (t, J = 8.8 Hz, 2H), 6.14 (d, J = 7.6 Hz, 1H), 5.67 (s, 1H), 5.57 (d, J = 4.4 Hz, 1H), 4.99 (s, 1H), 1.60 (s, 3H), 1.59 (d, J = 7.2 Hz, 3H), 1.41 (s, 3H). |

TABLE 1-2-continued

| Example | Structural formula of compound | Characterization data of compounds (MS/HNMR) |
|---|---|---|
| 26 | 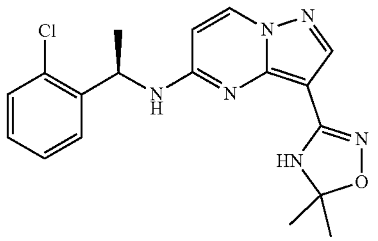 [SMILES: C[C@@H](Nc1ccn2ncc(C3=NOC(C)(C)N3)c2n1)c1ccccc1Cl] | $^1$H NMR (400 MHz, $CDCl_3$) δ 8.18 (d, J = 7.6 Hz, 1H), 8.15 (s, 1H), 7.41-7.34 (m, 2H), 7.26-7.17 (m, 2H), 6.22 (d, J = 7.6 Hz, 1H), 5.83 (d, J = 5.6 Hz, 2H), 5.47 (s, 1H), 1.64 (s, 3H), 1.56 (d, J = 6.8 Hz, 3H), 1.42 (s, 3H). |
| 27 | 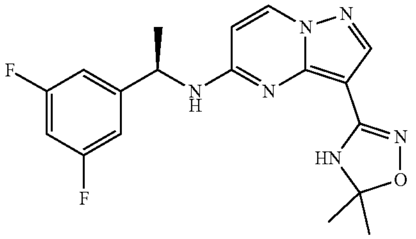 [SMILES: C[C@@H](Nc1ccn2ncc(C3=NOC(C)(C)N3)c2n1)c1cc(F)cc(F)c1] | $^1$H NMR (400 MHz, $CDCl_3$) δ 8.21 (d, J = 7.6 Hz, 1H), 8.15 (s, 1H), 6.93-6.84 (m, 2H), 6.71 (m, 1H), 6.23 (d, J = 7.6 Hz, 1H), 5.86 (d, J = 4.8 Hz, 1H), 5.61 (s, 1H), 5.01-4.90 (m, 1H), 1.63 (s, 3H), 1.57 (d, J = 7.2 Hz, 3H), 1.39 (s, 3H). |
| 28 | 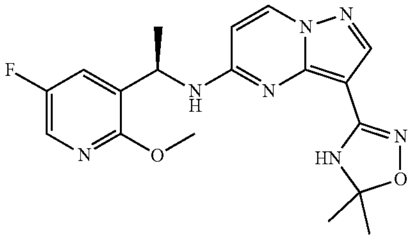 [SMILES: COc1ncc(F)cc1[C@@H](C)Nc1ccn2ncc(C3=NOC(C)(C)N3)c2n1] | $^1$H NMR (400 MHz, $CDCl_3$) δ 8.14 (d, J = 7.6 Hz, 1H), 8.09 (s, 1H), 7.83 (d, J = 2.9 Hz, 1H), 7.24 (dd, J = 8.1, 2.9 Hz, 1H), 6.13 (d, J = 7.3 Hz, 1H), 5.72 (d, J = 5.9 Hz, 1H), 5.62 (s, 1H), 5.17-5.04 (m, 1H), 3.97 (s, 3H), 1.52 (s, 3H), 1.49 (d, J = 6.9 Hz, 3H), 1.33 (s, 3H). |
| 29 | 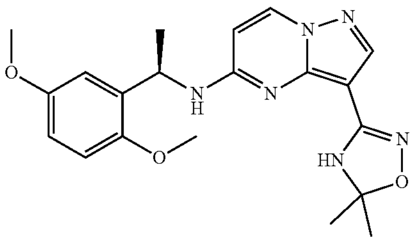 [SMILES: COc1ccc(OC)c([C@@H](C)Nc2ccn3ncc(C4=NOC(C)(C)N4)c3n2)c1] | $^1$H NMR (400 MHz, $CDCl_3$) δ 8.15 (d, J = 7.8 Hz, 2H), 6.87 (d, J = 8.8 Hz, 1H), 6.83 (d, J = 3.0 Hz, 1H), 6.74 (dd, J = 8.8, 3.0 Hz, 1H), 6.10 (d, J = 7.5 Hz, 1H), 6.00 (s, 1H), 5.69 (t, J = 10.1 Hz, 1H), 5.30 (s, 1H), 3.88 (s, 3H), 3.73 (s, 3H), 1.63 (s, 3H), 1.55 (d, J = 6.8 Hz, 3H), 1.47 (s, 3H). |
| 30 | 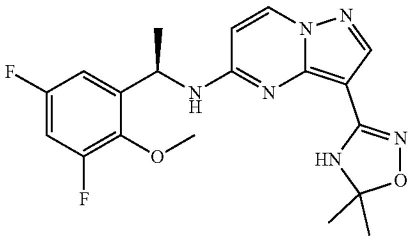 [SMILES: COc1c(F)cc(F)cc1[C@@H](C)Nc1ccn2ncc(C3=NOC(C)(C)N3)c2n1] | $^1$H NMR (400 MHz, $CDCl_3$) δ 8.16 (t, J = 3.8 Hz, 2H), 6.86 (ddd, J = 8.8, 2.9, 1.8 Hz, 1H), 6.75 (ddd, J = 11.1, 8.1, 3.0 Hz, 1H), 6.27-6.10 (m, 3H), 5.54 (s, 1H), 4.00 (s, 3H), 1.68 (s, 3H), 1.56 (d, J = 7.0 Hz, 3H), 1.53 (s, 3H). |
| 31 | 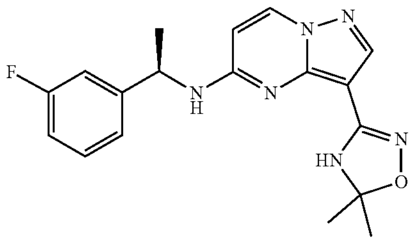 [SMILES: C[C@@H](Nc1ccn2ncc(C3=NOC(C)(C)N3)c2n1)c1cccc(F)c1] | $^1$H NMR (400 MHz, $CDCl_3$) δ 8.21 (d, J = 7.6 Hz, 1H), 8.17 (s, 1H), 7.33 (td, J = 7.9, 5.9 Hz, 1H), 7.13 (d, J = 7.7 Hz, 1H), 7.08-7.01 (m, 1H), 6.97 (tdd, J = 8.5, 2.5, 0.8 Hz, 1H), 6.15 (d, J = 7.6 Hz, 1H), 5.61 (s, 1H), 5.48 (d, J = 4.5 Hz, 1H), 5.08-4.91 (m, 1H), 1.62 (s, 3H), 1.60 (s, 3H), 1.37 (s, 3H). |

TABLE 1-2-continued

| Example | Structural formula of compound | Characterization data of compounds (MS/HNMR) |
|---|---|---|
| 32 | 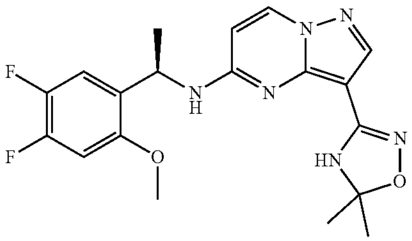 [SMILES: COc1cc(F)c(F)cc1[C@@H](C)Nc1ccn2ncc(C3=NOC(C)(C)N3)c2n1] | $^1$H NMR (400 MHz, $CDCl_3$) δ 8.19 (d, J = 7.6 Hz, 1H), 8.16 (s, 1H), 7.09 (dd, J = 10.7, 8.9 Hz, 1H), 6.76 (dd, J = 11.7, 6.5 Hz, 1H), 6.15 (d, J = 6.7 Hz, 1H), 5.89 (s, 1H), 5.74 (d, J = 6.4 Hz, 1H), 5.29-5.21 (m, 1H), 3.89 (s, 3H), 1.61 (s, 3H), 1.53 (d, J = 6.8 Hz, 3H), 1.47 (s, 3H). |
| 33 | 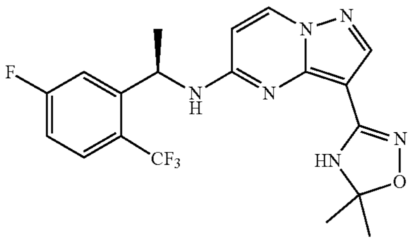 [SMILES: C[C@@H](Nc1ccn2ncc(C3=NOC(C)(C)N3)c2n1)c1cc(F)ccc1C(F)(F)F] | $^1$H NMR (400 MHz, $CDCl_3$) δ 8.19 (d, J = 4.3 Hz, 2H), 7.71 (dd, J = 8.7, 5.4 Hz, 1H), 7.37 (dd, J = 9.2, 1.3 Hz, 1H), 7.11-7.00 (m, 1H), 6.29 (d, J = 7.1 Hz, 1H), 6.05 (s, 1H), 5.80 (s, 1H), 5.44 (t, J = 8.9 Hz, 1H), 1.59 (s, 3H), 1.42 (s, 3H), 1.26 (s, 3H). |
| 34 | 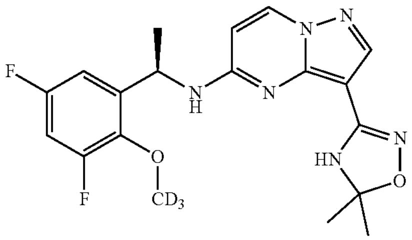 [SMILES: [2H]C([2H])([2H])Oc1c(F)cc(F)cc1[C@@H](C)Nc1ccn2ncc(C3=NOC(C)(C)N3)c2n1] | $^1$H NMR (400 MHz, $CDCl_3$) δ 8.16 (t, J = 3.8 Hz, 2H), 6.86 (ddd, J = 8.8, 2.9, 1.8 Hz, 1H), 6.75 (ddd, J = 11.1, 8.1, 3.0 Hz, 1H), 6.21 (d, J = 7.6 Hz, 1H), 6.17 (s, 1H), 6.11 (d, J = 4.9 Hz, 1H), 5.52 (s, 1H), 1.68 (s, 3H), 1.56 (d, J = 7.0 Hz, 3H), 1.53 (s, 3H). |
| 35 | 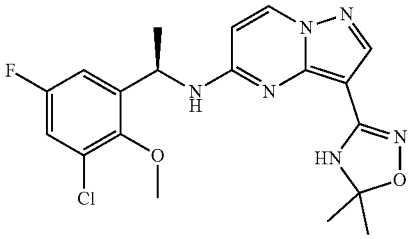 [SMILES: COc1c(Cl)cc(F)cc1[C@@H](C)Nc1ccn2ncc(C3=NOC(C)(C)N3)c2n1] | $^1$H NMR (400 MHz, $CDCl_3$) δ 8.14 (dd, J = 7.7, 1.9 Hz, 2H), 7.07 (dt, J = 7.9 3.9 Hz 1H) 7.03-6.99 (m, 1H), 6.49 (d, J = 45.3 Hz, 1H), 6.32-6.19 (m, 2H), 5.58 (d, J = 5.7 Hz, 1H), 3.98 (s, 3H), 1.72 (s, 3H), 1.61-1.56 (m, 6H). |
| 36 | 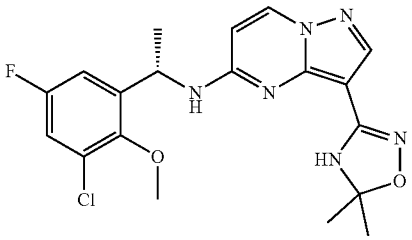 [SMILES: COc1c(Cl)cc(F)cc1[C@H](C)Nc1ccn2ncc(C3=NOC(C)(C)N3)c2n1] | $^1$H NMR (400 MHz, $CDCl_3$) δ 8.18 (d, J = 8.1 Hz, 2H), 7.03 (dd, J = 7.7 , 3.0 Hz , 1H) , 6.98 (dd , J = 8.7, 3.1 Hz, 1H), 6.14 (t, J = 4.9 Hz, 2H), 5.76 (d, J = 6.4 Hz, 1H), 5.62-5.50 (m, 1H), 3.98 (s, 3H), 1.69 (s, 3H), 1.60- 1.56 (m, 6H). |
| 37 | 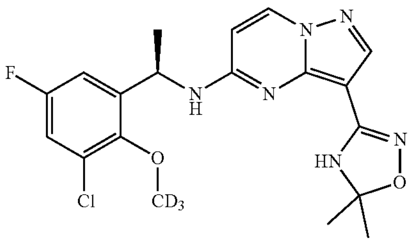 | $^1$H NMR (400 MHz, $CDCl_3$) δ 8.15 (d, J = 7.5 Hz, 2H), 7.03-7.01 (m, 2H), 6.25-6.23 (m, 3H), 5.57 (d, J = 5.6 Hz, 1H), 1.71 (s, 3H), 1.58 (d, J = 7.0 Hz, 6H). |

TABLE 1-2-continued

| Example | Structural formula of compound | Characterization data of compounds (MS/HNMR) |
|---|---|---|
| 38 | 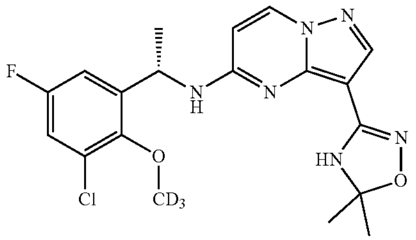 [SMILES: [2H]C([2H])([2H])Oc1c(Cl)cc(F)cc1[C@H](C)Nc1ccn2ncc(C3=NOC(C)(C)N3)c2n1] | $^1H$ NMR (400 MHz, $CDCl_3$) δ 8.16 (m, 2H), 7.03 (s, 1H), 7.01-7.00 (m, 1H), 6.19 (d, J = 7.5 Hz, 2H), 6.08 (d, J = 5.7 Hz, 1H), 5.62-5.51 (m, 1H), 1.70 (s, 3H), 1.60-1.56 (m, 6H). |
| 39 | 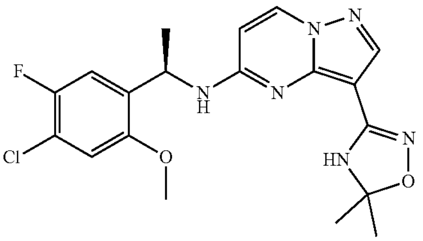 [SMILES: COc1cc(Cl)c(F)cc1[C@@H](C)Nc1ccn2ncc(C3=NOC(C)(C)N3)c2n1] | $^1H$ NMR (400 MHz, $CDCl_3$) δ 8.19 (d, J = 7.6 Hz, 1H), 8.16 (s, 1H), 7.07 (d, J = 9.3 Hz, 1H), 6.93 (d, J = 5.9 Hz, 1H), 6.16 (d, J = 6.0 Hz, 1H), 5.84 (s, 1H), 5.78 (d, J = 6.1 Hz, 1H), 5.29-5.20 (m, 1H), 3.91 (s, 3H), 1.61 (s, 3H), 1.53 (d, J = 6.9 Hz, 3H), 1.45 (s, 3H). |
| 40 | 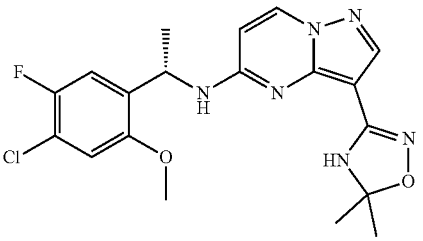 [SMILES: COc1cc(Cl)c(F)cc1[C@H](C)Nc1ccn2ncc(C3=NOC(C)(C)N3)c2n1] | $^1H$ NMR (400 MHz, $CDCl_3$) δ 8.20 (d, J = 7.6 Hz, 1H), 8.17 (s, 1H), 7.06 (d, J = 9.3 Hz, 1H), 6.93 (d, J = 5.9 Hz, 1H), 6.13 (d, J = 6.7 Hz, 1H), 5.82 (s, 1H), 5.66 (d, J = 6.3 Hz, 1H), 5.28-5.18 (m, 1H), 1.61 (s, 3H), 1.54 (d, J = 6.9 Hz, 3H), 1.46 (s, 3H). |
| 41 | 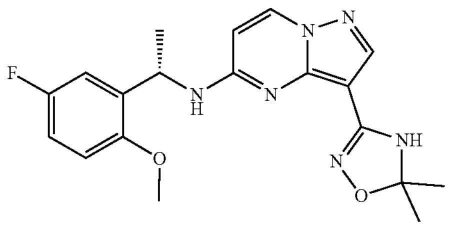 [SMILES: COc1ccc(F)cc1[C@H](C)Nc1ccn2ncc(C3=NOC(C)(C)N3)c2n1] | $^1H$ NMR (400 MHz, $CDCl_3$) δ 8.19 (d, J = 7.7 Hz, 2H), 6.94 (m, 3H), 6.09 (d, J = 7.5 Hz, 1H), 5.87 (s, 1H), 5.47 (s, 1H), 5.30 (s, 1H), 3.91 (s, 3H), 1.62 (s, 3H), 1.56 (d, J = 3.4 Hz, 6H). |
| 42 | 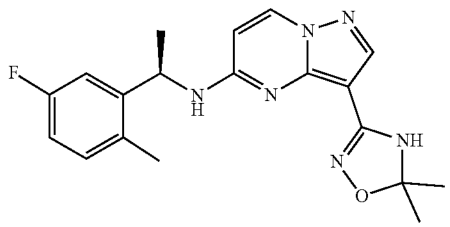 [SMILES: Cc1ccc(F)cc1[C@@H](C)Nc1ccn2ncc(C3=NOC(C)(C)N3)c2n1] | $^1H$ NMR (400 MHz, $CDCl_3$) δ 8.26-8.13 (m, 2H), 7.16 (dd, J = 8.3, 5.7 Hz, 1H), 7.03 (dd, J = 9.9, 2.7 Hz, 1H), 6.87 (td, J = 8.3, 2.8 Hz, 1H), 6.13 (d, J = 6.8 Hz, 1H), 5.42 (d, J = 28.0 Hz, 2H), 5.12 (s, 1H), 2.44 (s, 3H), 1.61 (s, 3H), 1.58 (s, 3H), 1.54 (d, J = 6.8 Hz, 3H). |
| 43 | 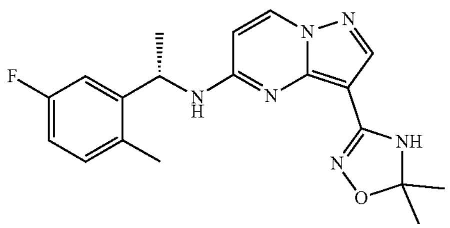 [SMILES: Cc1ccc(F)cc1[C@H](C)Nc1ccn2ncc(C3=NOC(C)(C)N3)c2n1] | $^1H$ NMR (400 MHz, $CDCl_3$) δ 8.28-8.10 (m, 2H), 7.16 (dd, J = 8.3, 5.7 Hz, 1H), 7.02 (dt, J = 9.3, 4.6 Hz, 1H), 6.87 (td, J = 8.2, 2.7 Hz, 1H), 6.11 (d, J = 7.1 Hz, 1H), 5.37 (d, J = 55.7 Hz, 2H), 5.12 (s, 1H), 2.44 (s, 3H), 1.61 (s, 3H), 1.56 (s, 3H), 1.54 (d, J = 6.9 Hz, 3H). |

TABLE 1-2-continued

| Example | Structural formula of compound | Characterization data of compounds (MS/HNMR) |
|---|---|---|
| 44 | 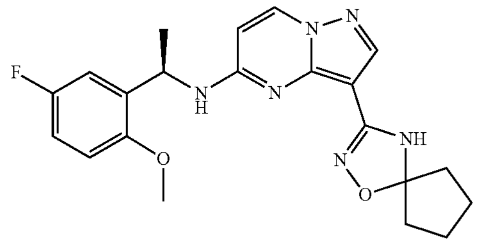 [SMILES: COc1ccc(F)cc1[C@@H](C)Nc1ccn2ncc(C3=NOC4(CCCC4)N3)c2n1] | $^1H$ NMR (400 MHz, $CDCl_3$) δ 8.20 (d, J = 7.1 Hz, 2H), 6.98-6.81 (m, 3H), 6.08 (d, J = 7.3 Hz, 1H), 5.93 (s, 1H), 5.46 (s, 1H), 5.28 (s, 1H), 3.89 (s, 3H), 2.27-1.64 (m, 8H), 1.26 (s, 3H). |
| 45 | 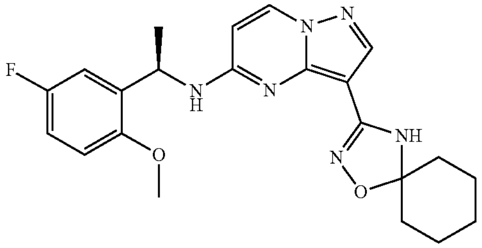 [SMILES: COc1ccc(F)cc1[C@@H](C)Nc1ccn2ncc(C3=NOC4(CCCCC4)N3)c2n1] | $^1H$ NMR (400 MHz, $CDCl_3$) δ 8.19 (t, J = 3.8 Hz, 2H), 7.01-6.81 (m, 3H), 6.07 (d, J = 7.4 Hz, 2H), 5.55 (d, J = 6.8 Hz, 1H), 5.30 (s, 1H), 3.90 (s, 3H), 1.84 (ddd, J = 42.1, 36.8, 11.4 Hz, 8H), 1.42 (d, J = 4.6 Hz, 2H), 1.26 (s, 3H). |
| 46 | 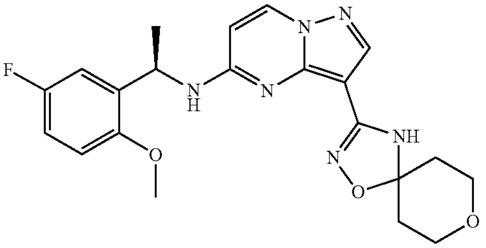 [SMILES: COc1ccc(F)cc1[C@@H](C)Nc1ccn2ncc(C3=NOC4(CCOCC4)N3)c2n1] | $^1H$ NMR (400 MHz, $CDCl_3$) δ 8.26-8.13 (m, 2H), 7.02-6.84 (m, 3H), 6.17-6.02 (m, 2H), 5.46 (s, 1H), 5.32 (s, 1H), 3.93 (s, 3H), 3.83 (ddd, J = 19.8, 9.0, 5.2 Hz, 4H), 2.00 (ddd, J = 20.9, 13.3, 4.5 Hz, 4H), 1.26 (s, 3H). |
| 47 | 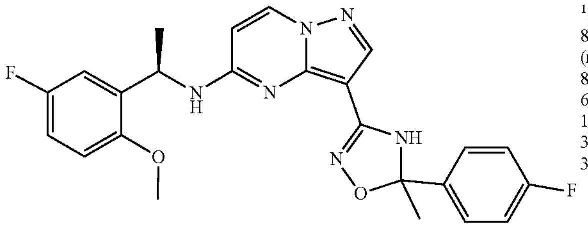 | $^1H$ NMR (400 MHz, $CDCl_3$) δ 8.26-8.15 (m, 2H), 7.73-7.60 (m, 1H), 7.39 (s, 1H), 7.08 (t, J = 8.7 Hz, 1H), 7.03-6.69 (m, 4H), 6.59 (s, 1H), 6.12 (d, J = 5.2 Hz, 1H), 5.38-5.24 (m, 2H), 3.69 (s, 3H), 1.53 (dd, J = 6.7, 3.7 Hz, 3H), 1.26 (s, 3H). |
| 48 | 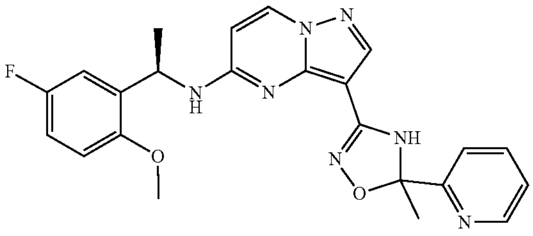 [SMILES: COc1ccc(F)cc1[C@@H](C)Nc1ccn2ncc(C3=NOC(C)(c4ccccn4)N3)c2n1] | $^1H$ NMR (400 MHz, $CDCl_3$) δ 8.55 (dd, J = 22.0, 4.5 Hz, 1H), 8.19-8.10 (m, 2H), 7.84-7.58 (m, 2H), 7.40 (d, J = 40.0 Hz, 1H), 7.21 (dd, J = 11.8, 5.9 Hz, 1H), 7.13-6.75 (m, 3H), 6.02 (d, J = 7.3 Hz, 1H), 5.82 (dd, J = 17.0, 10.2 Hz, 1H), 5.34 (s, 1H), 3.87 (t, J = 7.3 Hz, 3H), 1.95 (d, J = 12.4 Hz, 3H), 1.61 (dd, J = 11.8, 6.8 Hz, 3H). |
| 49 | 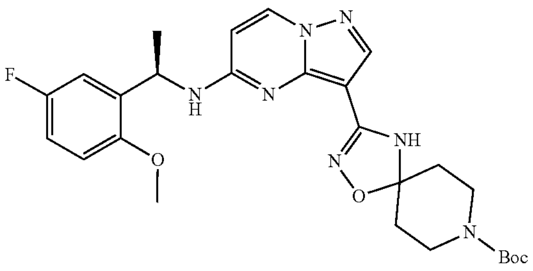 [SMILES: COc1ccc(F)cc1[C@@H](C)Nc1ccn2ncc(C3=NOC4(CCN(C(=O)OC(C)(C)C)CC4)N3)c2n1] | $^1H$ NMR (400 MHz, $CDCl_3$) δ 8.17 (dd, J = 19.6, 6.8 Hz, 2H), 7.05-6.77 (m, 3H), 6.15 (d, J = 6.6 Hz, 1H) δ.03 (s, 1H), 5.62 (t, J = 9.1 Hz, 1H), 5.30 (s, 1H), 3.87 (s, 3H), 3.79-3.17 (m, 4H), 2.13-1.62 (m, 4H), 1.48 (d, J = 17.8 Hz, 9H), 1.26 (s, 3H). |

TABLE 1-2-continued

| Example | Structural formula of compound | Characterization data of compounds (MS/HNMR) |
|---|---|---|
| 50 | 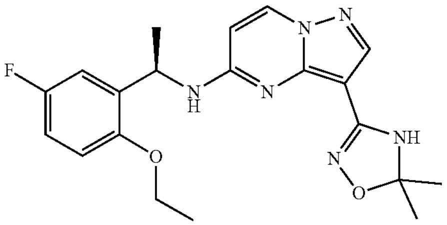 [SMILES: CCOc1ccc(F)cc1[C@@H](C)Nc1ccn2ncc(C3=NOC(C)(C)N3)c2n1] | $^1$H NMR (400 MHz, $CDCl_3$) δ 8.25-8.16 (m, 2H), 6.98-6.82 (m, 3H), 6.08 (d, J = 7.6 Hz, 1H), 5.87 (s, 1H), 5.47 (s, 1H), 5.28 (s, 1H), 4.20-4.01 (m, 2H), 1.61 (s, 3H), 1.58 (s, 3H), 1.47 (t, J = 7.0 Hz, 6H). |
| 51 | 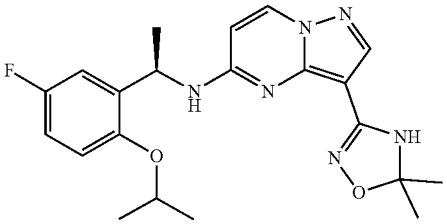 [SMILES: CC(C)Oc1ccc(F)cc1[C@@H](C)Nc1ccn2ncc(C3=NOC(C)(C)N3)c2n1] | $^1$H NMR (400 MHz, $CDCl_3$) δ 8.26-8.13 (m, 2H), 6.98-6.81 (m, 3H), 6.05 (d, J = 7.6 Hz, 1H), 5.87 (s, 1H), 5.51 (s, 1H), 5.20 (s, 1H), 4.59 (dt, J = 12.1, 6.0 Hz, 1H), 1.62 (s, 3H), 1.57 (s, 6H), 1.41 (d, J = 6.1 Hz, 3H), 1.36 (d, J = 6.0 Hz, 3H). |
| 52 | 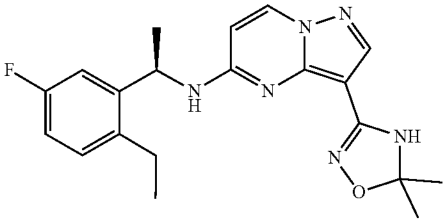 [SMILES: CCc1ccc(F)cc1[C@@H](C)Nc1ccn2ncc(C3=NOC(C)(C)N3)c2n1] | $^1$H NMR (400 MHz, $CDCl_3$) δ 8.21 (d, J = 6.8 Hz, 2H), 7.22 (dd, J = 8.5, 5.8 Hz, 1H), 7.07 (dd, J = 10.0, 2.7 Hz, 1H), 6.94 (td, J = 8.3, 2.7 Hz, 1H), 6.06 (d, J = 7.7 Hz, 1H), 5.62 (s, 1H), 5.28 (d, J = 19.7 Hz, 2H), 2.88-2.66 (m, 2H), 1.59 (d, J = 7.5 Hz, 6H), 1.43 (s, 3H), 1.31 (t, J = 7.6 Hz, 3H). |
| 53 | 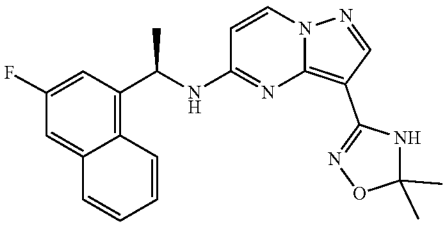 [SMILES: C[C@@H](Nc1ccn2ncc(C3=NOC(C)(C)N3)c2n1)c1cc(F)cc2ccccc12] | $^1$H NMR (400 MHz, $CDCl_3$) δ 8.22 (d, J = 7.6 Hz, 1H), 8.12 (s, 2H), 7.88 (dd, J = 6.0, 3.6 Hz, 1H), 7.65-7.54 (m, 2H), 7.35 (ddd, J = 20.2, 9.5, 2.5 Hz, 2H), 6.28 (s, 1H), 5.81 (s, 2H), 5.19 (s, 1H), 1.71 (d, J = 6.6 Hz, 3H), 1.22 (d, J = 31.4 Hz, 6H). |
| 54 | 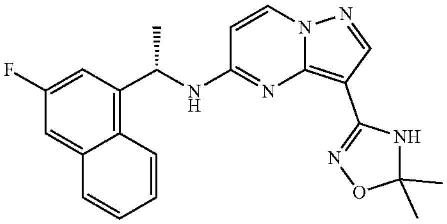 [SMILES: C[C@H](Nc1ccn2ncc(C3=NOC(C)(C)N3)c2n1)c1cc(F)cc2ccccc12] | $^1$H NMR (400 MHz, $CDCl_3$) δ 8.24 (d, J = 7.6 Hz, 1H), 8.14 (s, 2H), 7.88 (dd, J = 6.0, 3.6 Hz, 1H), 7.59 (dd, J = 6.4, 3.3 Hz, 2H), 7.35 (ddd, J = 23.9, 9.5, 2.5 Hz, 2H), 6.24 (s, 1H), 5.84 (s, 1H), 5.60 (d, J = 4.1 Hz, 1H), 5.16 (s, 1H), 1.72 (d, J = 6.9 Hz, 3H), 1.22 (d, J = 32.7 Hz, 6H). |
| 55 | 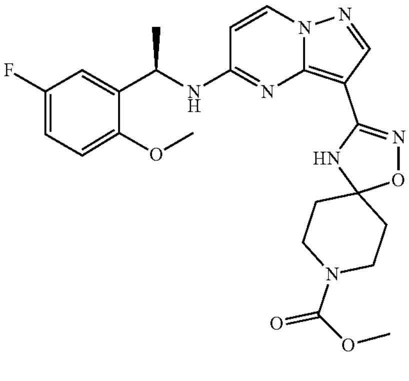 [SMILES: COC(=O)N1CCC2(CC1)NC(c1cnn3ccc(N[C@H](C)c4cc(F)ccc4OC)nc13)=NO2] | $^1$H NMR (400 MHz, $CH_3Cl$) δ: 8.20 (d, J = 7.6 Hz, 1H), 8.16 (s, 1H), 6.94 (t, J = 10.7 Hz, 2H), 6.85 (s, 1H), 6.14 (d, J = 7.0 Hz, 1H), 6.05 (s, 1H), 5.61 (d, J = 5.9 Hz, 1H), 5.30 (s, 1H), 3.92 (s, 1H), 3.86 (s, 3H), 3.75 (s, 3H), 3.39-3.31 (m, 2H), 2.08 (d, J = 12.6 Hz, 1H), 1.90-1.75 (m, 2H), 1.64 (s, 1H), 1.54 (d, J = 6.8 Hz, 3H). |

TABLE 1-2-continued
| Example | Structural formula of compound | Characterization data of compounds (MS/HNMR) |
|---|---|---|
| 56 | 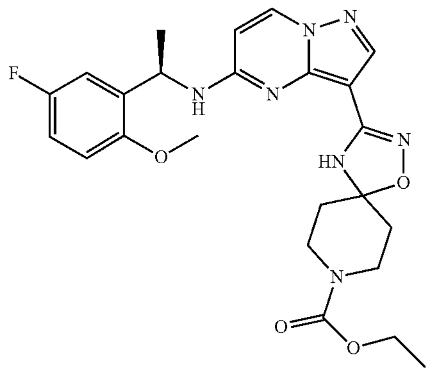 [SMILES: CCOC(=O)N1CCC2(CC1)NC(c1cnn3ccc(N[C@H](C)c4cc(F)ccc4OC)nc13)=NO2] | $^{1}$H NMR (400 MHz, $CH_3Cl$) δ: 8.21 (d, J = 7.6 Hz, 1H), 8.17 (s, 1H), 6.93 (t, J = 9.3 Hz, 2H), 6.85 (d, J = 3.4 Hz, 1H), 6.12 (d, J = 7.0 Hz, 1H), 6.02 (s, 1H), 5.47 (s, 1H), 5.30 (s, 1H), 4.20-4.10 (m, 2H), 3.96 (m, 2H), 3.86 (s, 3H), 3.39-3.27 (m, 2H), 2.09-2.04 (m, 1H), 1.91 (d, J = 11.5 Hz, 1H), 1.80-1.74 (m, 1H), 1.58 (s, 1H), 1.54 (d, J = 6.8 Hz, 3H), 1.33-1.28 (m, 3H). |
| 57 | 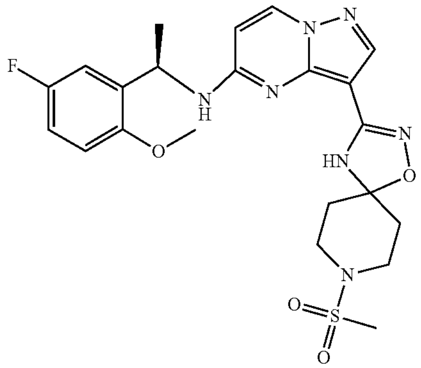 | $^{1}$H NMR (400 MHz, $CH_3Cl$) δ: 8.21 (d, J = 7.6 Hz, 1H), 8.15 (s, 1H), 6.94 (d, J = 6.7 Hz, 3H), 6.15 (d, J = 6.9 Hz, 1H), 6.06 (s, 1H), 5.51 (s, 1H), 5.30 (s, 1H), 3.94 (s, 3H), 3.85-3.81 (m, 1H), 3.76-3.73 (m, 1H), 3.13-3.03 (m, 2H), 2.84 (s, 3H), 2.22-2.18 (m, 2H), 2.04-1.91 (m, 2H), 1.54 (d, J = 6.8 Hz, 2H), 1.41 (d, J = 9.2 Hz, 1H). |
| 58 | 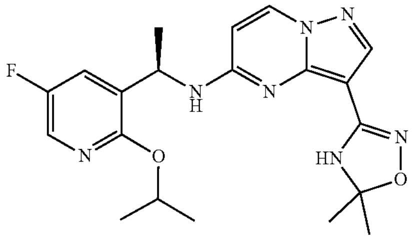 [SMILES: CC(C)Oc1ncc(F)cc1[C@@H](C)Nc1ccn2ncc(C3=NOC(C)(C)N3)c2n1] | $[M + H]^+$ 414.2 |
| 59 | 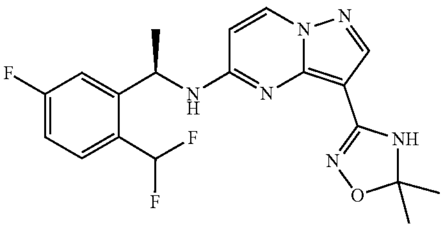 [SMILES: C[C@@H](Nc1ccn2ncc(C3=NOC(C)(C)N3)c2n1)c1cc(F)ccc1C(F)F] | $[M + H]^+$ 405.1 |
| 60 | 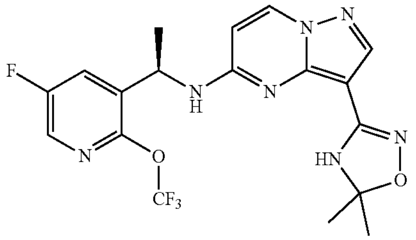 [SMILES: C[C@@H](Nc1ccn2ncc(C3=NOC(C)(C)N3)c2n1)c1cc(F)cnc1OC(F)(F)F] | $[M + H]^+$ 440.1 |

TABLE 1-2-continued
| Example | Structural formula of compound | Characterization data of compounds (MS/HNMR) |
|---|---|---|
| 61 | 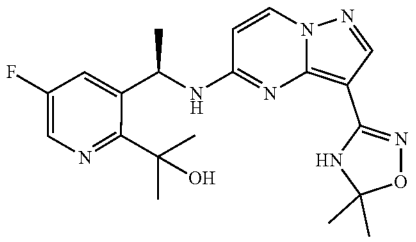 [SMILES: C[C@@H](Nc1ccn2ncc(C3=NOC(C)(C)N3)c2n1)c1cc(F)cnc1C(C)(C)O] | $[M + H]^+$ 414.2 |
| 62 | 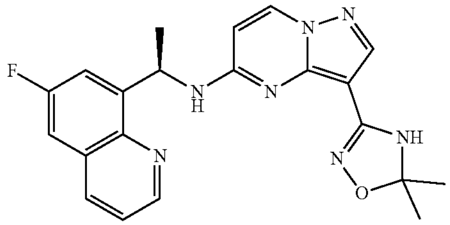 [SMILES: C[C@@H](Nc1ccn2ncc(C3=NOC(C)(C)N3)c2n1)c1cc(F)cc2cccnc12] | $[M + H]^+$ 406.2 |
| 63 | 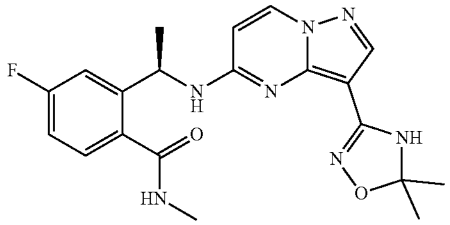 [SMILES: CNC(=O)c1ccc(F)cc1[C@@H](C)Nc1ccn2ncc(C3=NOC(C)(C)N3)c2n1] | $[M + H]^+$ 412.2 |
| 64 | 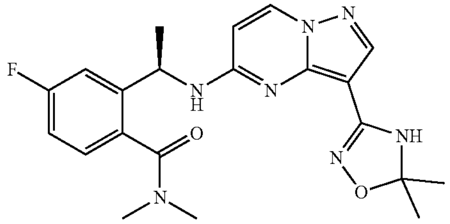 [SMILES: C[C@@H](Nc1ccn2ncc(C3=NOC(C)(C)N3)c2n1)c1cc(F)ccc1C(=O)N(C)C] | $[M + H]^+$ 426.2 |
| 65 | 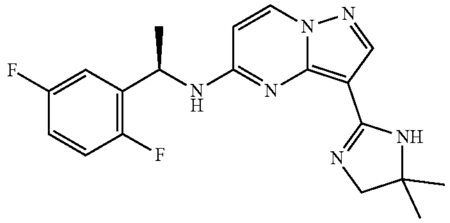 [SMILES: C[C@@H](Nc1ccn2ncc(C3=NCC(C)(C)N3)c2n1)c1cc(F)ccc1F] | $[M + H]^+$ 371.2 |
| 66 | 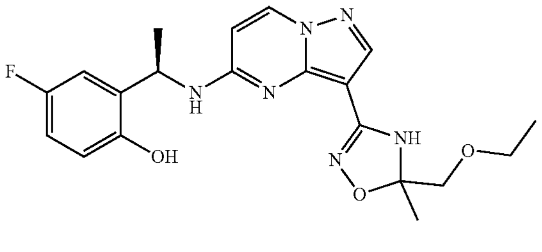 [SMILES: CCOCC1(C)NC(c2cnn3ccc(N[C@H](C)c4cc(F)ccc4O)nc23)=NO1] | $[M + H]^+$ 415.2 |

TABLE 1-2-continued
| Example | Structural formula of compound | Characterization data of compounds (MS/HNMR) |
|---|---|---|
| 67 | 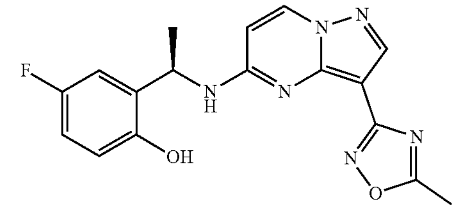 [SMILES: Cc1nc(-c2cnn3ccc(N[C@H](C)c4cc(F)ccc4O)nc23)no1] | $[M + H]^+$ 355.1 |
| 68 | 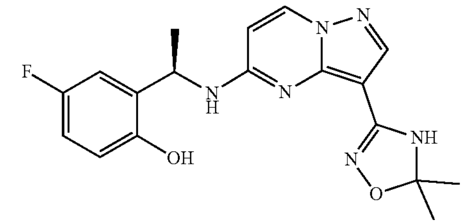 [SMILES: C[C@@H](Nc1ccn2ncc(C3=NOC(C)(C)N3)c2n1)c1cc(F)ccc1O] | $[M + H]^+$ 371.1 |
| 69 | 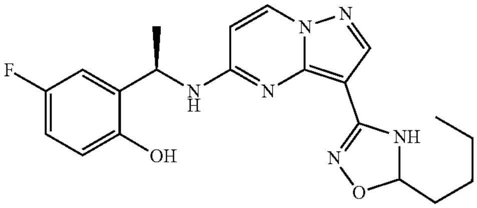 [SMILES: CCCCC1NC(c2cnn3ccc(N[C@H](C)c4cc(F)ccc4O)nc23)=NO1] | $[M + H]^+$ 399.2 |
| 70 | 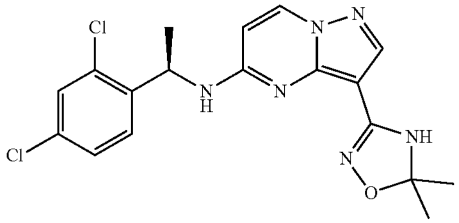 [SMILES: C[C@@H](Nc1ccn2ncc(C3=NOC(C)(C)N3)c2n1)c1ccc(Cl)cc1Cl] | $[M + H]^+$ 405.1/407.1 |
| 71 | 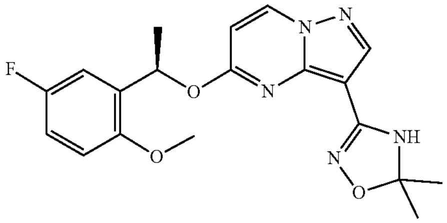 [SMILES: COc1ccc(F)cc1[C@@H](C)Oc1ccn2ncc(C3=NOC(C)(C)N3)c2n1] | $[M + H]^+$ 386.1 |
| 72 | 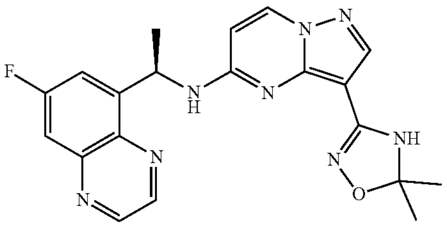 [SMILES: C[C@@H](Nc1ccn2ncc(C3=NOC(C)(C)N3)c2n1)c1cc(F)cc2nccnc12] | $[M + H]^+$ 407.2 |

TABLE 1-2-continued
| Example | Structural formula of compound | Characterization data of compounds (MS/HNMR) |
|---|---|---|
| 73 | 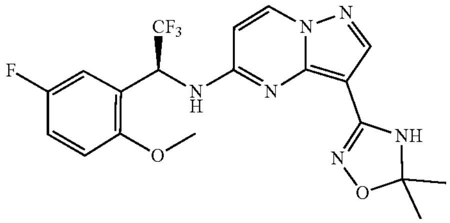 [SMILES: COc1ccc(F)cc1[C@H](Nc1ccn2ncc(C3=NOC(C)(C)N3)c2n1)C(F)(F)F] | $[M + H]^+$ 439.1 |
| 74 | 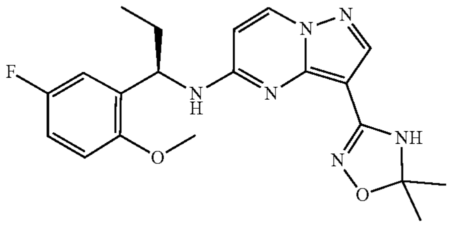 [SMILES: CC[C@@H](Nc1ccn2ncc(C3=NOC(C)(C)N3)c2n1)c1cc(F)ccc1OC] | $[M + H]^+$ 399.2 |
| 75 | 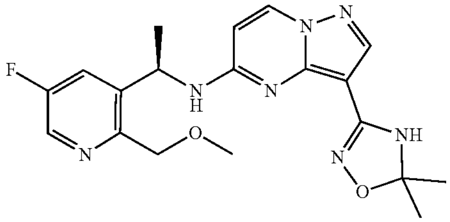 [SMILES: COCc1ncc(F)cc1[C@@H](C)Nc1ccn2ncc(C3=NOC(C)(C)N3)c2n1] | $[M + H]^+$ 400.2 |
| 76 | 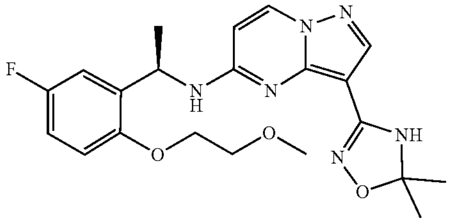 [SMILES: COCCOc1ccc(F)cc1[C@@H](C)Nc1ccn2ncc(C3=NOC(C)(C)N3)c2n1] | $[M + H]^+$ 429.2 |
| 77 | 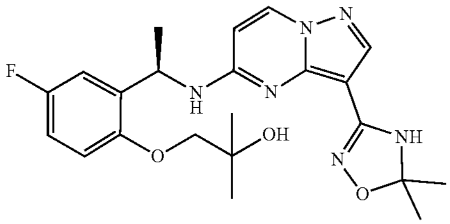 [SMILES: C[C@@H](Nc1ccn2ncc(C3=NOC(C)(C)N3)c2n1)c1cc(F)ccc1OCC(C)(C)O] | $[M + H]^+$ 443.2 |
| 78 | 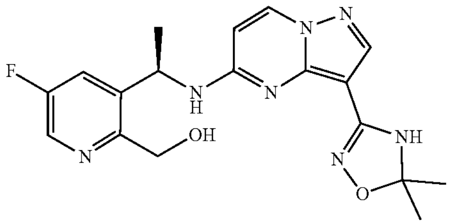 [SMILES: C[C@@H](Nc1ccn2ncc(C3=NOC(C)(C)N3)c2n1)c1cc(F)cnc1CO] | $[M + H]^+$ 386.2 |

TABLE 1-2-continued
| Example | Structural formula of compound | Characterization data of compounds (MS/HNMR) |
|---|---|---|
| 79 | 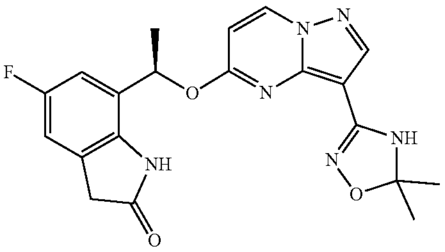 [SMILES: C[C@@H](Oc1ccn2ncc(C3=NOC(C)(C)N3)c2n1)c1cc(F)cc2c1NC(=O)C2] | $[M + H]^+$ 411.1 |
| 80 | 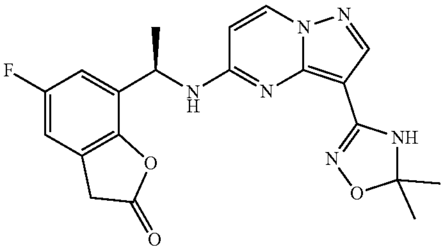 [SMILES: C[C@@H](Nc1ccn2ncc(C3=NOC(C)(C)N3)c2n1)c1cc(F)cc2c1OC(=O)C2] | $[M + H]^+$ 411.1 |
| 81 | 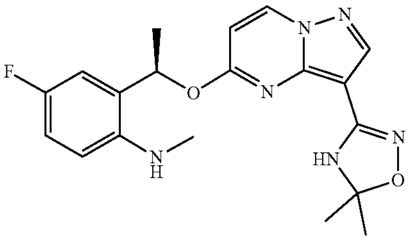 [SMILES: CNc1ccc(F)cc1[C@@H](C)Oc1ccn2ncc(C3=NOC(C)(C)N3)c2n1] | $[M + H]^+$ 385.2 |
| 82 | 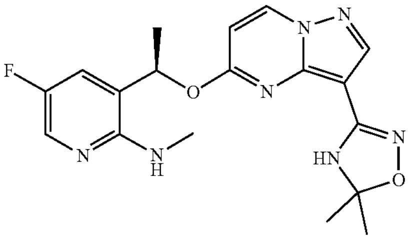 [SMILES: CNc1ncc(F)cc1[C@@H](C)Oc1ccn2ncc(C3=NOC(C)(C)N3)c2n1] | $[M + H]^+$ 386.2 |
| 83 | 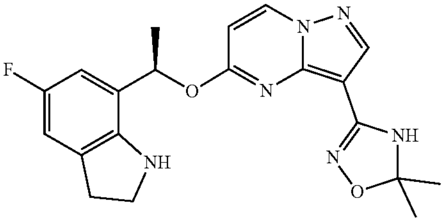 [SMILES: C[C@@H](Oc1ccn2ncc(C3=NOC(C)(C)N3)c2n1)c1cc(F)cc2c1NCC2] | $[M + H]^+$ 397.2 |

Example 84 Example 25 and its Enantiomers

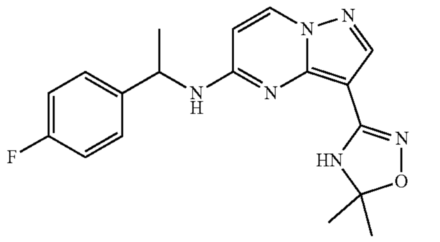 [SMILES: CC(Nc1ccn2ncc(C3=NOC(C)(C)N3)c2n1)c1ccc(F)cc1]

Synthetic Route of Chiral Amine Intermediates:

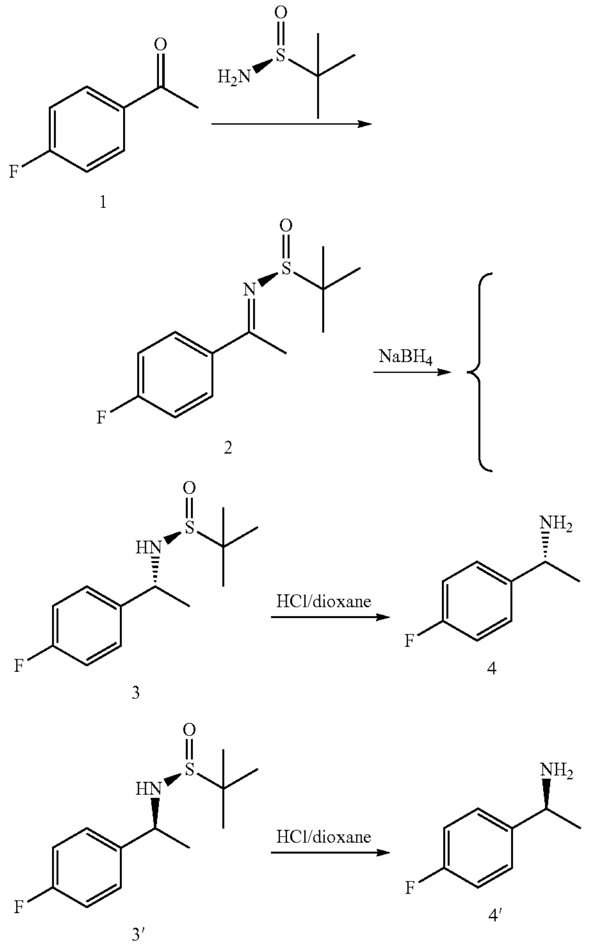

1, 2, 3, 4, 3', 4'

The synthesis of example 84 referred to the synthesis of chiral amine intermediate compound 4 in Example 12. p-fluoroacetophenone and (R)-tert-butyl sulfinamide were used as raw materials to obtain imine which was reduced with sodium borohydride and then a pair of diastereomer compound 3 and compound 3' were obtained. The two compounds were separated by column chromatography, and then the tert-butyl sulfinyl group was removed to obtain two chiral amine intermediates with R and S configuration. The two chiral amine intermediates were reacted separately to obtain a compound Example 84 i.e. R (i.e., Example 25) and S-configuration compounds. The two chiral amine intermediates were mixed to obtain Example 84, which was a racemate.

Example 85 Resolution of Example 48

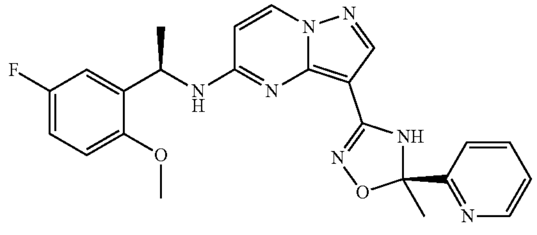

(R/R)

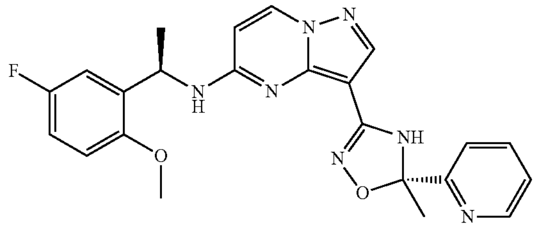

(R/S)

The two compounds were separated by preparation liquid phase under the following separation conditions:

Instruments: Waters2525 & Waters2767;
Column: Innoval ODS-2 (30×100 mm, 5 microns);
Flow rate: 15.0 ml/min, detection wavelength: 254 nm;
Solvent: Methanol, sample concentration was 12 mg/ml;
Injection volume: 0.5 ml, delay time: 24 seconds;
Threshold: 20,000, timetable: 2.00,
Mobile phase: A: water (containing 0.1% trifluoroacetic acid), B; methanol.

Gradient Program:

| t (min) | Phase A | Phase B |
|---|---|---|
| 0 | 41 | 59 |
| 22 | 41 | 59 |
| 25 | 10 | 90 |
| 27 | 10 | 90 |
| 28 | 41 | 59 |
| 30 | 41 | 59 |

Test Example 1: Inhibitory Activity of the Compounds of the Invention Against ROS1, NTRK and ALK and their Drug-Resistant Kinases Inhibition of protein kinase activity by compounds was carried out on the Radio-tagged HotSpot kinase experimental platform of Reaction Biology Corporation. Fresh reaction solution (20 mM HEPESpH 7.5, 10 mM $MgCl_2$, 1 mM EGTA, 0.02% Brij35, 0.02 mg/ml BSA, 0.1 mM $Na_3VO_4$, 2 mM DTT, 1% DMSO) containing corresponding substrates was prepared, cofactor and kinase to be tested were added into the above solution and mixed gently. Echo550 pipetting system was used to add the test compound DMSO solution to each well (the blank control group was added with the corresponding volume of DMSO), then 33P-ATP (with a final specific activity of 0.01 μCi/μL) was added to start the reaction. The reaction solution was incubated at room temperature for 120 minutes. Transferred the incubated reaction solution to P81 ion exchange chromatographic paper (Whatman #3698-915), eluted with 0.75% phosphoric acid solution, and the amount of radioactive phosphorylated substrate remaining on the chromatographic paper was detected.

Table 2 showed the inhibitory activity $IC_{50}$ Value of the compounds of the present invention against ROS1, NTRK and ALK and the drug-resistant kinases thereof, wherein a <0.5 nM, 0.5 nM≤B≤5.0 nM, 5.0 nM<C<50 nM, 50 nM≤D≤500 nM, E>500 nM;

TABLE 2

| Example | ROS1 ($IC_{50}$/nM) | ROS1 (G2032R) ($IC_{50}$/nM) | TRKA ($IC_{50}$/nM) | TRKA (G677C) ($IC_{50}$/nM) | TRKA (G595R) ($IC_{50}$/nM) | TRKB ($IC_{50}$/nM) | TRKC ($IC_{50}$/nM) | ALK ($IC_{50}$/nM) | ALK (G1202R) ($IC_{50}$/nM) |
|---|---|---|---|---|---|---|---|---|---|
| 4 | A | A | A | C | C | A | A | B | C |
| 5 | A | A | B | C | C | A | A | B | C |
| 9 | A | | A | D | | B | A | D | |
| 10 | A | A | A | B | B | A | A | C | B |
| 14 | B | B | B | C | C | B | B | | C |
| 23 | B | B | B | C | C | B | B | | C |
| 24 | | | E | | | | | | |
| 25 | | | D | | | | | | |
| 25 racemate | | | D | | | | | | |
| 26 | B | | B | | | B | B | C | |
| 27 | B | | B | | | B | B | C | |
| 28 | A | A | A | C | B | A | A | C | B |
| 41 | | | D | | | | | | |
| 42 | B | | B | | | B | B | C | |
| 43 | | | D | | | | | | |
| 44 | | | | B | | | | | |
| 45 | | | | C | | | | | |
| 46 | | | | C | | | | | |
| 47 | | | | D | | | | | |
| 48 | | | | D | | | | | |
| 50 | A | A | B | B | B | A | A | C | B |
| 51 | A | A | B | C | C | A | A | C | B |
| 52 | A | B | B | D | C | B | A | D | C |
| 55 | A | A | B | | B | A | A | | |
| 54 | A | A | B | | B | B | A | | |
| 57 | A | A | B | | B | B | A | | |
| 65 | A | A | B | | B | B | A | | |
| 66 | A | A | B | | B | B | A | | |
| 67 | B | C | C | | C | B | B | | |
| 68 | A | A | A | | A | A | A | | |
| 69 | A | A | A | | A | A | A | | |
| 71 | B | B | B | | B | B | B | | |
| Staurosporine | 0.246 | 13.0 | 2.11 | | 5.3 | 0.473 | 0.106 | | |

The kinase activity test shows that the series compounds of the present invention have good inhibitory activity on ROS1, NTRK and ALK and the drug-resistant mutations thereof, especially the inhibitory activity on drug-resistant mutations is better.

The compounds of the present invention have better inhibitory activity against one or more of ROS1, NTRK and ALK and the drug-resistant mutations thereof than that of currently clinically available drugs.

Most of the compounds of the invention have better or equivalent activity against one or more of ROS1, NTRK and ALK and the drug-resistant mutations thereof than current clinically available drugs.

The compounds of the invention have great potential for use in the treatment of diseases mediated by ROS1, NTRK, ALK and the like.

Test Example 2: Inhibition of Cell Proliferation by Compounds

The experiment of inhibiting cell proliferation by compounds was carried out in Hefei Zhongkeprecedo Biomedical Technology Co., Ltd. The Ba/F3 engineered cell line stably transfected with different kinase genes was recovered with RPMI 1640 medium (Biological Industries, Israel)+10% fetal bovine serum (Biological Industries, Israel)+1% double antibody (Penicillin Streptomycin solution, Coring, USA) and cultivated two generations. The logarithmic growth phase cell suspension was taken, and 2000 cells/well were inoculated on 96-well white cell culture plate (Corning 3917, NY, USA) with a volume of 95 μL per well. 5 μL of 20×DMSO solution of the compound to be tested was added into the culture plate containing 95 μL of cell suspension. The blank control group was added with corresponding volume of DMSO, mixed well, and incubated in a 5% $CO_2$ incubator at 37° C. for 72 hours. CellTiter-Glo was used to detect cell viability.

Table 3 showed the inhibitory activity $IC_{50}$ Value of the compounds of the present invention against ROS1, NTRK and ALK or their drug-resistant mutant Ba/F3 engineered cell lines.

TABLE 3

| Example | Ba/F3-CD74-ROS1 ($IC_{50}$/nM) | Ba/F3-CD74-ROS1-G2032R ($IC_{50}$/nM) | Ba/F3-LMNA-NTRK1 ($IC_{50}$/nM) | Ba/F3-LMNA-NTRK1-G595R ($IC_{50}$/nM) | Ba/F3-TEL-ALK-G1202R ($IC_{50}$/nM) |
|---|---|---|---|---|---|
| 1 | | | | 457.9 | |
| 2 | | | | 112.6 | |
| 3 | 2.8 | 10.3 | 2.1 | 3.3 | |
| 6 | 6.0 | 43.7 | 2.0 | 2.8 | |
| 9 | 26.2 | 154.8 | 100.5 | 890.1 | |
| 10 | 2.8 | 7.9 | 1.3 | 2.2 | 87.5 |
| 13 | 5.2 | 45.9 | 5.1 | 12.5 | |
| 15 | 4.9 | 34.8 | 3.8 | 8.6 | |
| 17 | 2.8 | 23.5 | 2.3 | 5.1 | |
| 19 | | 139.8 | | | |
| 20 | | 43.6 | | | |
| 29 | | | | 386.6 | |
| 30 | 2.2 | 16.3 | 5.8 | 7.0 | |
| 31 | | 54.4 | | 3.5 | |
| 32 | 52.1 | | 45.8 | 161.2 | |
| 33 | 15.7 | 120.5 | 25.9 | 386.5 | |
| 44 | 6.9 | 59.2 | 14.2 | 13.9 | |
| 53 | 8.4 | 81.1 | 18.2 | 30.1 | |
| 55 | 6.6 | 47.9 | 26.7 | 25.4 | |
| 57 | 4.5 | 38.9 | 26.2 | 45.3 | |
| 71 | 32.2 | 185 | 76.9 | 109.7 | |

The cell activity test shows that the series compounds of the present invention have good inhibitory activity against ROS1, NTRK and ALK and their drug-resistant mutant Ba/F3 engineered cell lines, especially the inhibitory activity against drug-resistant mutations is better. The compounds of the invention have good inhibitory activity against ROS1, NTRK and ALK and their drug-resistant mutant Ba/F3 engineering cell lines, and most of the compounds of the invention have excellent activity against ROS1, NTRK and ALK and their drug-resistant mutant Ba/F3 engineering cell lines, and they have great potential to be applied to the treatment of diseases mediated by ROS1, NTRK and ALK and the like.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound represented by formula I, or a tautomer thereof, or a mesomer thereof, or a racemate thereof, or a mixture of the mesomer and the racemate thereof, or an enantiomer thereof, or a diastereomer thereof, or a mixture of the enantiomer and the diastereomer thereof, or a pharmaceutically acceptable salt thereof, or a deuterated compound thereof:

I

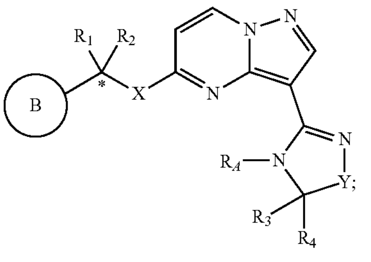

wherein * denotes R configuration, and X is independently selected from the group consisting of $NR_6$, O, $CR_1R_2$, S, S(O) and $S(O)_2$;

B is selected from the group consisting of phenyl, 5-6 membered heteroaryl; wherein, H on any carbon atom of the phenyl and 5-6 membered heteroaryl is optionally substituted by the following substituents: halogen, hydroxy, amino, cyano, $C_1$-$C_6$ alkyl, $C_3$-$C_6$ cycloalkyl, $C_1$-$C_6$ alkylamino, $C_1$-$C_6$ alkoxy, $C_3$-$C_6$ cycloalkoxy, monosubstituted or polysubstituted $C_1$-$C_6$ alkyl, monosubstituted or polysubstituted $C_1$-$C_6$ alkoxy, monosubstituted or polysubstituted $C_3$-$C_6$ cycloalkyl and monosubstituted or polysubstituted $C_3$-$C_6$ cycloalkoxy; the substituents of the monosubstituted or polysubstituted $C_1$-$C_6$ alkyl, the monosubstituted or polysubstituted $C_1$-$C_6$ alkoxy, the monosubstituted or polysubstituted $C_3$-$C_6$ cycloalkyl and the monosubstituted or polysubstituted $C_3$-$C_6$ cycloalkoxy are independently selected from the group consisting of deuterium, halogen, amino, cyano, hydroxyl, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy and $C_1$-$C_6$ haloalkoxy;

or B is selected from the group consisting of

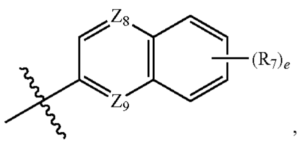

,

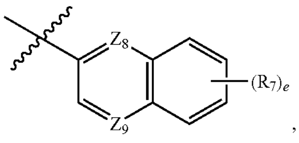

,

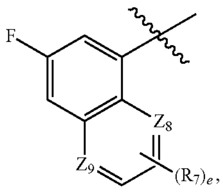

-continued

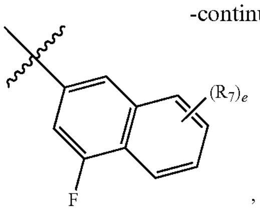
,
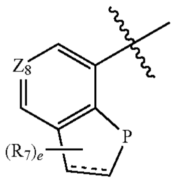
and
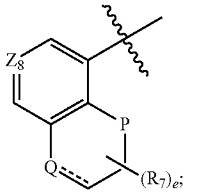

wherein, $\overline{---}$ is a single bond or a double bond;

$Z_8$ and $Z_9$ are each independently selected from $CR_{11}$ or N;

P is independently selected from O, NH or S;

when $\overline{---}$ is a double bond, Q is independently selected from $CR_{11}$ or N; when $\overline{---}$ is a single bond, Q is independently selected from O, S, $CR_{11}R_{12}$ or NH;

$R_7$ is each independently selected from the group consisting of halogen, amino, cyano, hydroxy, $C_1$-$C_6$ alkyl, $C_3$-$C_6$ cycloalkyl, $C_1$-$C_6$ alkoxy, $C_1$-$C_6$ alkylamino, monosubstituted or polysubstituted $C_1$-$C_6$ alkyl, monosubstituted or polysubstituted $C_1$-$C_6$ alkoxy and monosubstituted or polysubstituted $C_3$-$C_6$ cycloalkyl; the substituents of the monosubstituted or polysubstituted $C_1$-$C_6$ alkyl, monosubstituted or polysubstituted $C_1$-$C_6$ alkoxy and monosubstituted or polysubstituted $C_3$-$C_6$ cycloalkyl are independently selected from the group consisting of deuterium, halogen, amino, cyano, hydroxy, $C_1$-$C_6$ alkyl, $C_1$-$C_6$ haloalkyl, $C_1$-$C_6$ alkoxy and $C_1$-$C_6$ haloalkoxy;

$R_{11}$ and $R_{12}$ are each independently selected from the group consisting of H, hydroxy, halogen, amino, cyano, $C_1$-$C_6$ alkyl, $C_1$-$C_6$ haloalkyl, $C_1$-$C_6$ alkoxy and $C_1$-$C_6$ haloalkoxy;

e is 0, 1, 2, 3 or 4;

Y is independently selected from the group consisting of O, $NR_A$ and $CR_1R_2$;

wherein $R_1$ and $R_2$ are each independently selected from the group consisting of hydrogen, halogen, amino, cyano, hydroxy, $C_1$-$C_6$ alkyl, $C_1$-$C_6$ alkoxy, $C_3$-$C_6$ cycloalkyl, monosubstituted or polysubstituted $C_1$-$C_6$ alkyl, monosubstituted or polysubstituted $C_1$-$C_6$ alkoxy and monosubstituted or polysubstituted $C_3$-$C_6$ cycloalkyl; the substituents of the monosubstituted or polysubstituted $C_1$-$C_6$ alkyl, the monosubstituted or polysubstituted $C_1$-$C_6$ alkoxy and the monosubstituted or polysubstituted $C_3$-$C_6$ cycloalkyl are independently selected from the group consisting of deuterium, halogen, amino, cyano and hydroxyl;

$R_3$ and $R_4$ are each independently selected from the group consisting of hydrogen, amino, hydroxy, $C_1$-$C_6$ alkyl, $C_3$-$C_6$ cycloalkyl, phenyl, 5-6 membered heteroaryl, monosubstituted or polysubstituted $C_1$-$C_6$ alkyl, monosubstituted or polysubstituted $C_1$-$C_6$ alkoxy, monosubstituted or polysubstituted $C_3$-$C_6$ cycloalkyl, monosubstituted or polysubstituted phenyl and monosubstituted or polysubstituted 5-6 membered heteroaryl; the substituents of the monosubstituted or polysubstituted $C_1$-$C_6$ alkyl, the monosubstituted or polysubstituted $C_1$-$C_6$ alkoxy, the monosubstituted or polysubstituted $C_3$-$C_6$ cycloalkyl, the monosubstituted or polysubstituted phenyl and the monosubstituted or polysubstituted 5-6 membered heteroaryl are independently selected from the group consisting of halogen, amino, cyano, hydroxy, $C_1$-$C_6$ alkyl, $C_1$-$C_6$ haloalkyl, $C_1$-$C_6$ alkoxy and $C_1$-$C_6$ haloalkoxy;

or $R_3$ and $R_4$ together with the C atom attached to them form substituted or unsubstituted 3-7 membered cycloalkane, substituted or unsubstituted 3-7 membered aza-cycloalkane, substituted or unsubstituted 3-7 membered oxa-cycloalkane or substituted or unsubstituted 3-7 membered thio-cycloalkane or oxo (=O); wherein the substituted means being substituted by one or more groups selected from the group consisting of $C_1$-$C_6$ alkyl, —$C(O)C_1$-$C_6$ alkyl, —$C(O)OC_1$-$C_6$ alkyl, —$S(O)_2C_1$-$C_6$ alkyl, and —$S(O)C_1$-$C_6$ alkyl;

$R_6$ and $R_A$ are each independently selected from the group consisting of hydrogen, $C_1$-$C_6$ alkyl, $C_3$-$C_6$ cycloalkyl, monosubstituted or polysubstituted $C_1$-$C_6$ alkyl and monosubstituted or polysubstituted $C_3$-$C_6$ cycloalkyl; the substituents of the monosubstituted or polysubstituted $C_1$-$C_6$ alkyl and the monosubstituted or polysubstituted $C_3$-$C_6$ cycloalkyl are independently selected from the group consisting of halogen, amino, cyano and hydroxy; and each heteroaryl containing 1, 2 or 3 ring heteroatoms selected from N, O or S.

2. A compound of claim 1, or a tautomer thereof, or a mesomer thereof, or a racemate thereof, or a mixture of the mesomer and the racemate thereof, or a enantiomer thereof, or a diastereomer thereof, or a mixture of the enantiomer and the diastereomer thereof, or a pharmaceutically acceptable salt thereof, or a deuterated compound thereof:

wherein, * denotes R configuration, and X is $NR_6$ or O;

B is selected from phenyl and 5-6 membered heteroaryl, wherein the H on any carbon atom of B is optionally substituted by the following substituents: halogen, hydroxyl, amino, cyano, $C_1$-$C_6$ alkyl, halo $C_1$-$C_6$ alkyl, $C_1$-$C_6$ alkylamino and $C_1$-$C_6$ alkoxy;

or B is

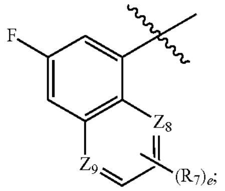

wherein, $Z_8$ and $Z_9$ are each independently selected from $CR_{11}$ or N;

$R_7$ is each independently selected from the group consisting of halogen, amino, cyano, hydroxy, $C_1$-$C_6$ alkyl, $C_1$-$C_6$ alkoxy, monosubstituted or polysubstituted $C_1$-$C_6$ alkyl and monosubstituted or polysubstituted $C_1$-$C_6$ alkoxy; the substituents of the monosubstituted or polysubstituted $C_1$-$C_6$ alkyl and monosubstituted or polysubstituted $C_1$-$C_6$ alkoxy are independently selected from the group consisting of deuterium, halogen, amino, cyano, hydroxy, $C_1$-$C_6$ alkyl, halo $C_1$-$C_6$ alkyl, $C_1$-$C_6$ alkoxy and halo $C_1$-$C_6$ alkoxy;

$R_{11}$ is each independently selected from the group consisting of H, hydroxy, halogen, amino, cyano, $C_1$-$C_6$ alkyl, halo $C_1$-$C_6$ alkyl, $C_1$-$C_6$ alkoxy and halo $C_1$-$C_6$ alkoxy;

e is 0, 1, 2, 3 or 4;

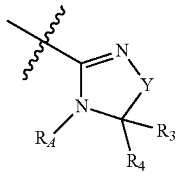

is optionally selected from

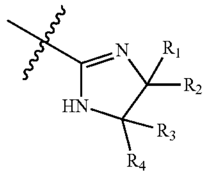

or

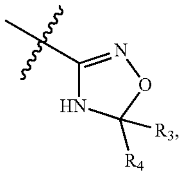

wherein the $R_1$, $R_2$, $R_3$, and $R_4$ are each independently selected from the group consisting of hydrogen, halogen, amino, cyano, hydroxyl, $C_1$-$C_6$ alkyl, $C_1$-$C_6$ alkoxy and monosubstituted or polysubstituted $C_1$-$C_6$ alkyl; the substituents of the monosubstituted or polysubstituted $C_1$-$C_6$ alkyl are independently selected from the group consisting of halogen, amino, cyano and hydroxy, or $R_3$ and $R_4$ together with the C atom attached to them form substituted or unsubstituted 3-7 membered cycloalkane, substituted or unsubstituted 3-7 membered aza-cycloalkane, substituted or unsubstituted 3-7 membered oxa-cycloalkane, or substituted or unsubstituted 3-7 membered thio-cycloalkane, wherein the substituted means being substituted by one or more groups selected from the group consisting of $C_1$-$C_6$ alkyl, —C(O) $C_1$-$C_6$ alkyl, —C(O) $OC_1$-$C_6$ alkyl, —$S(O)_2C_1$-$C_6$ alkyl, and —$S(O)C_1$-$C_6$ alkyl;

$R_6$ is each independently selected from the group consisting of hydrogen, $C_1$-$C_6$ alkyl, and monosubstituted or polysubstituted $C_1$-$C_6$ alkyl; the substituents of the monosubstituted or polysubstituted $C_1$-$C_6$ alkyl are independently selected from the group consisting of halogen, amino, cyano and hydroxy.

3. A compound of claim 1, or a tautomer thereof, or a mesomer thereof, or a racemate thereof, or a mixture of the mesomer and the racemate thereof, or a enantiomer thereof, or a diastereomer thereof, or a mixture of the enantiomer and the diastereomer thereof, or a pharmaceutically acceptable salt thereof, or a deuterated compound thereof, wherein,

* denotes R configuration;

X is $NR_6$ or O;

$R_1$ and $R_2$ are different and independently selected from the group consisting of hydrogen, halogen, amino, cyano, hydroxyl, $C_1$-$C_6$ alkyl and halo $C_1$-$C_6$ alkyl;

$R_6$ is independently selected from the group consisting of hydrogen, $C_1$-$C_6$ alkyl, and monosubstituted or polysubstituted $C_1$-$C_6$ alkyl, and the substituents of monosubstituted or polysubstituted $C_1$-$C_6$ alkyl are independently selected from the group consisting of halogen, amino, cyano and hydroxy.

4. A compound of claim 1, or a tautomer thereof, or a mesomer thereof, or a racemate thereof, or a mixture of the mesomer and the racemate thereof, or a enantiomer thereof, or a diastereomer thereof, or a mixture of the enantiomer and the diastereomer thereof, or a pharmaceutically acceptable salt thereof, or a deuterated compound thereof, wherein B is independently selected from the group consisting of

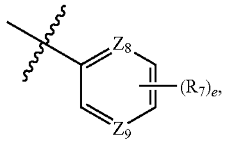

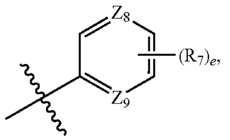

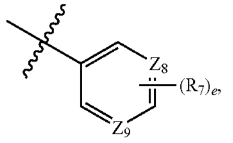

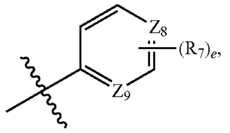

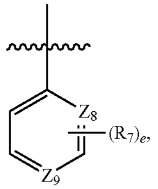

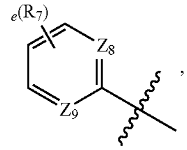

,

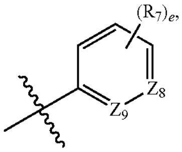

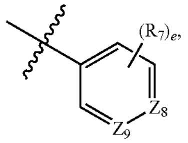

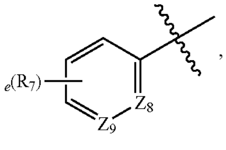

,

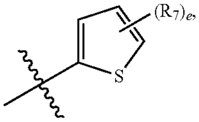

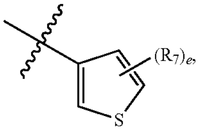

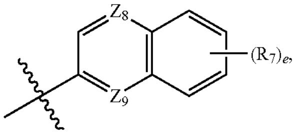

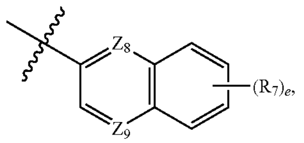

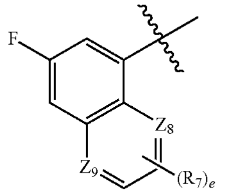

and

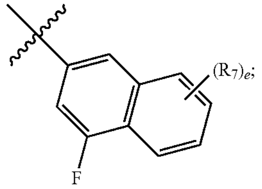

$Z_8$ and $Z_9$ are each independently selected from $CR_{11}$ or N;

each $R_7$ is independently selected from the group consisting of halogen, amino, cyano, hydroxy, $C_1$-$C_6$ alkyl, $C_1$-$C_6$ alkoxy, $C_1$-$C_6$ alkylamino, monosubstituted or polysubstituted $C_1$-$C_6$ alkyl, and monosubstituted or polysubstituted $C_1$-$C_6$ alkoxy; the substituents of the monosubstituted or polysubstituted $C_1$-$C_6$ alkyl, and the monosubstituted or polysubstituted $C_1$-$C_6$ alkoxy are independently selected from the group consisting of deuterium, halogen, amino, cyano, hydroxyl, $C_1$-$C_6$ alkyl, halo $C_1$-$C_6$ alkyl $C_1$-$C_6$ alkoxy and halo $C_1$-$C_6$ alkoxy;

$R_{11}$ is each independently selected from the group consisting of H, hydroxy, halogen, amino, cyano, $C_1$-$C_6$ alkyl, halo $C_1$-$C_6$alkyl, $C_1$-$C_6$ alkoxy, and halo $C_1$-$C_6$ alkoxy;

e is 0, 1, 2, 3 or 4.

5. A compound of claim 1, or a tautomer thereof, or a mesomer thereof, or a racemate thereof, or a mixture of the mesomer and the racemate thereof, or a enantiomer thereof, or a diastereomer thereof, or a mixture of the enantiomer and the diastereomer thereof, or a pharmaceutically acceptable salt thereof, or a deuterated compound thereof, wherein

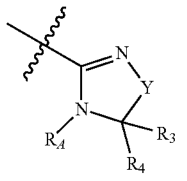

is

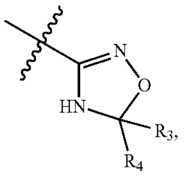

and $R_3$ and $R_4$ are as defined in claim 1.

6. A compound, or a tautomer thereof, or a mesomer thereof, or a racemate thereof, or a mixture of the mesomer and the racemate thereof, or a enantiomer thereof, or a diastereomer thereof, or a mixture of the enantiomer and the diastereomer thereof, or a pharmaceutically acceptable salt thereof, or a deuterated compound thereof, wherein the compound is selected from the following compounds:

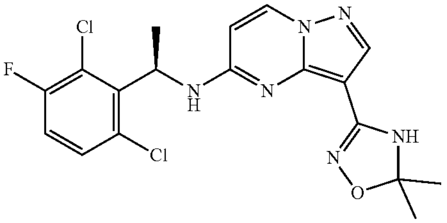

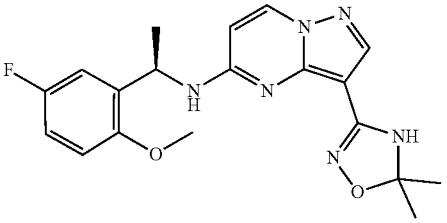

-continued

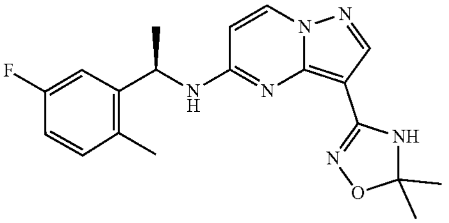

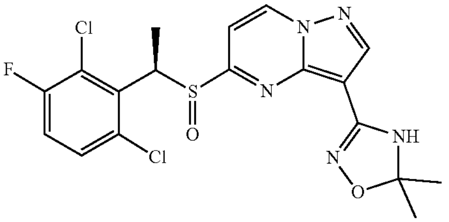

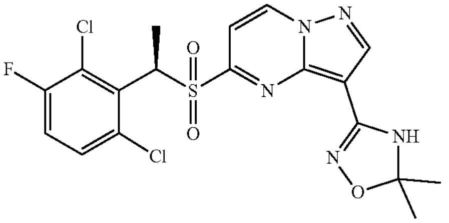

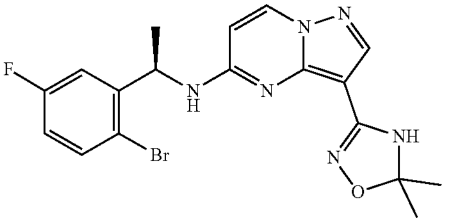

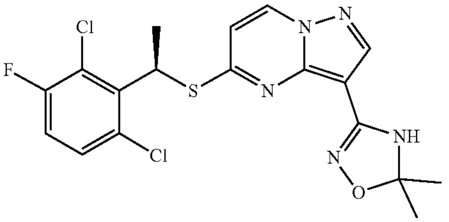

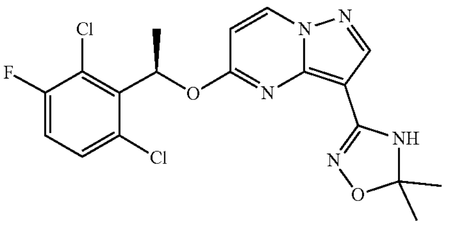

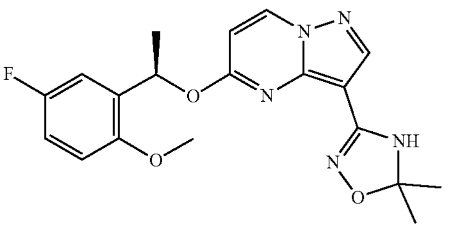

-continued
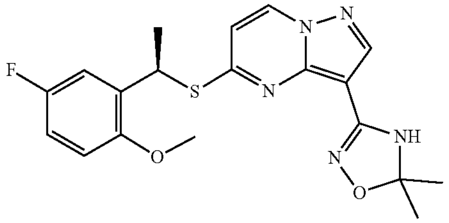
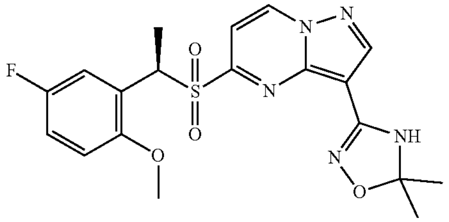
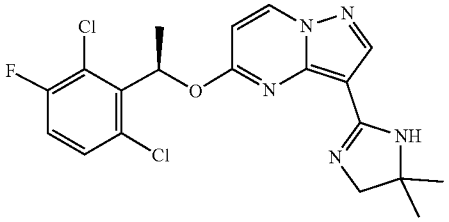
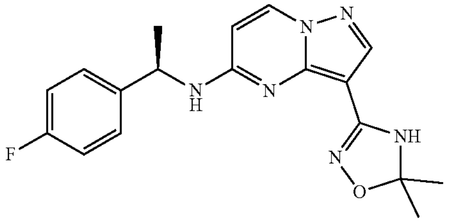
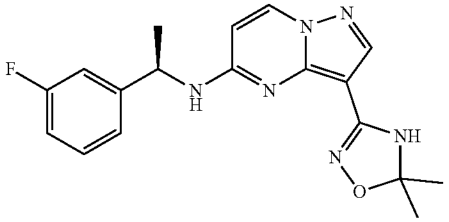
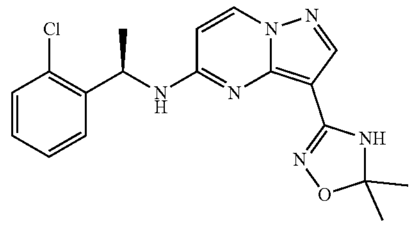
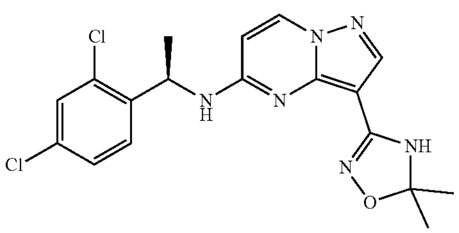
-continued
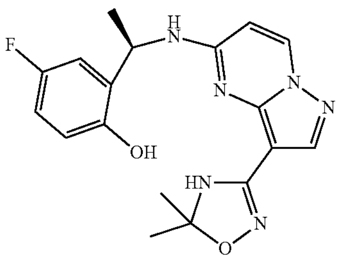
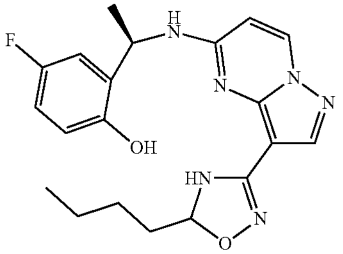
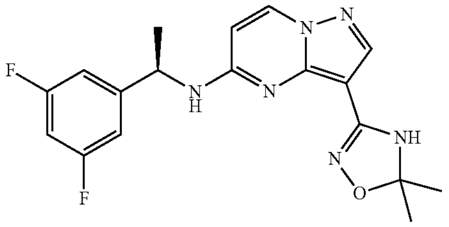
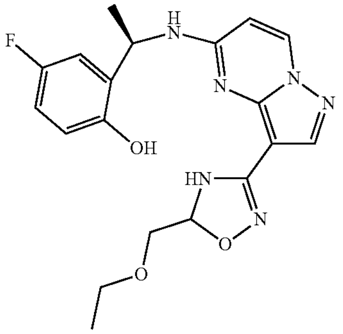
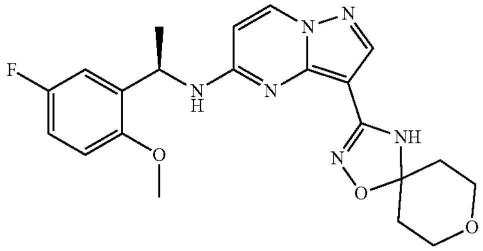
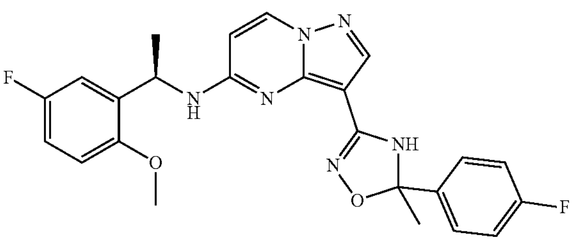

-continued
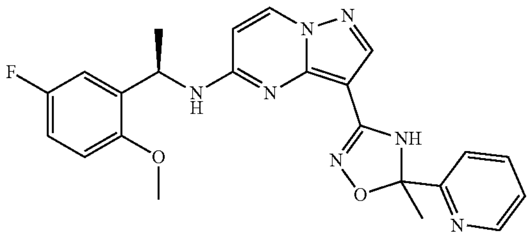
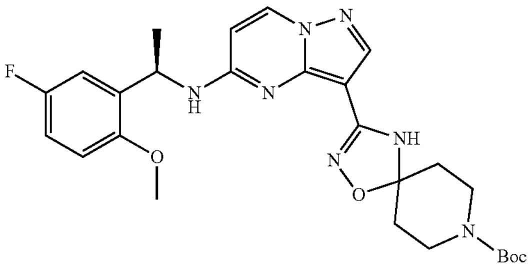
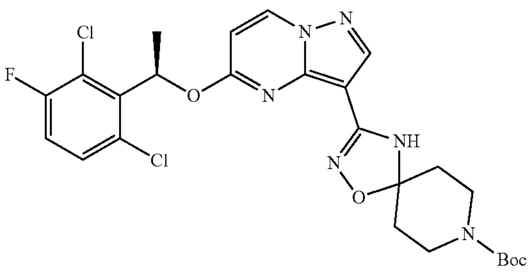
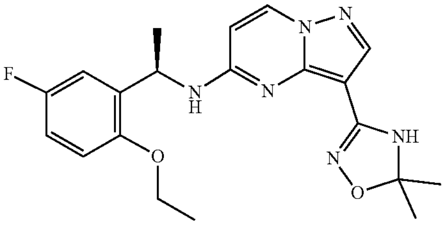
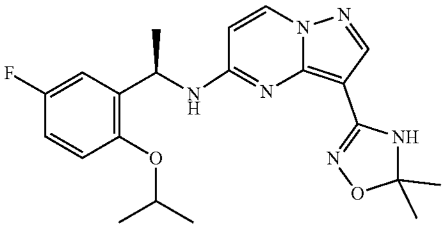
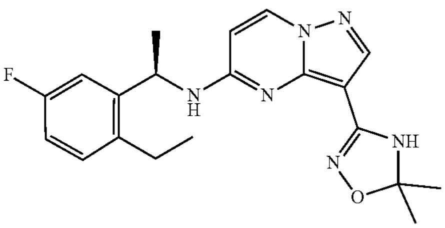
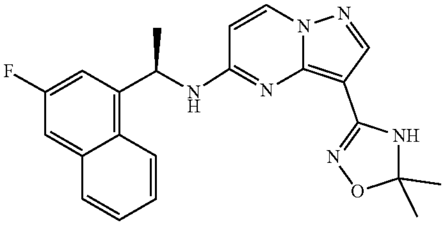
-continued
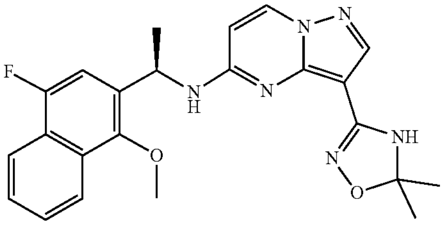
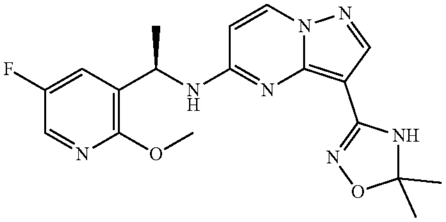
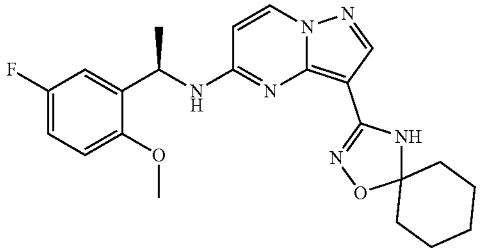
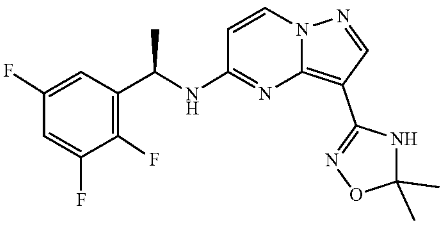
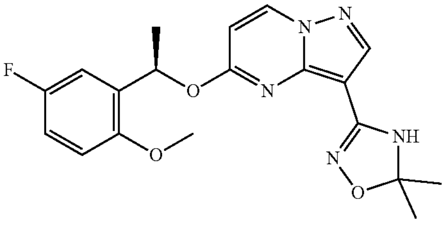
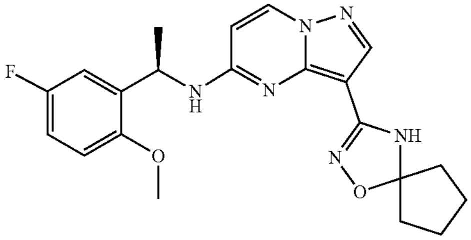
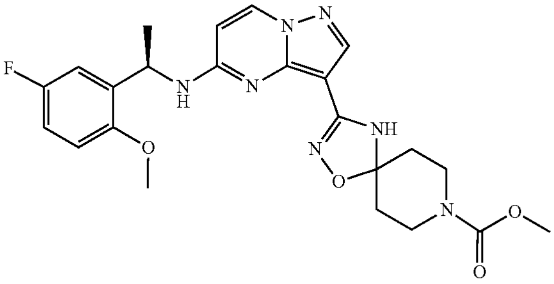

-continued
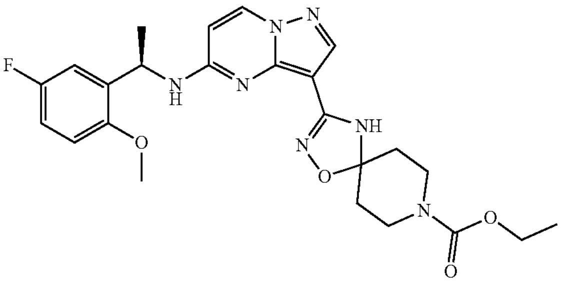
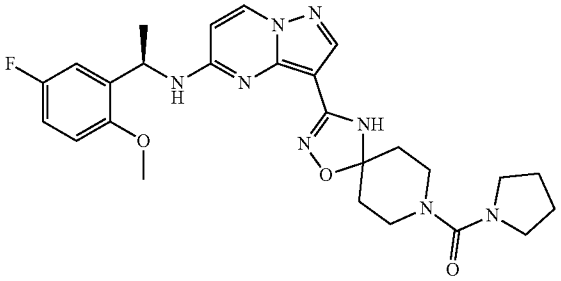
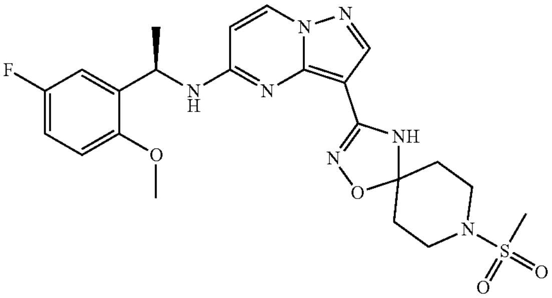
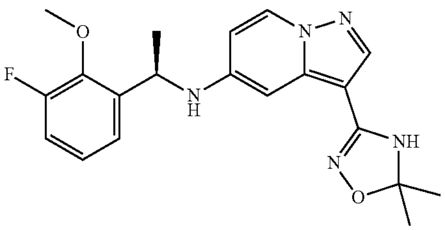
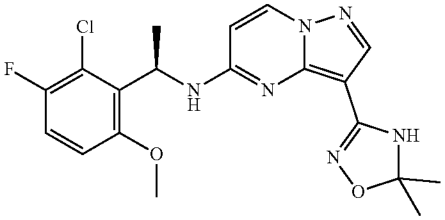
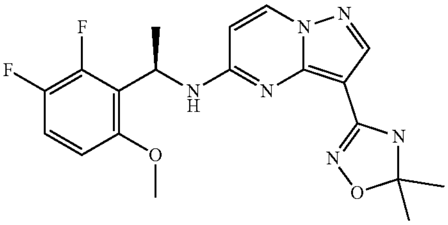
-continued
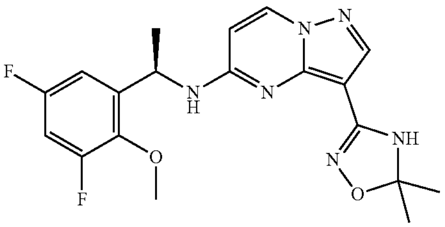
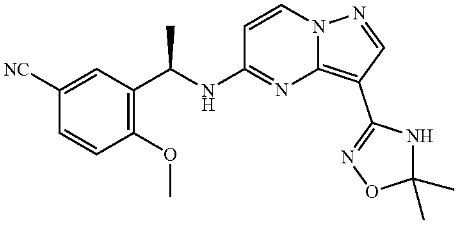
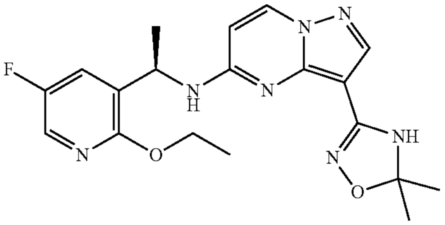
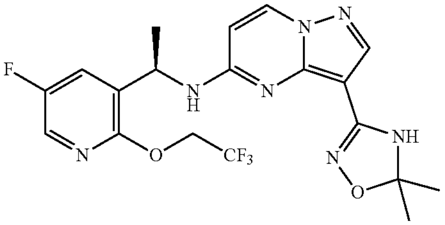
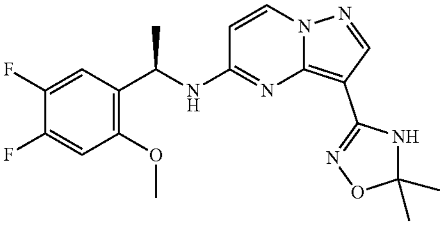
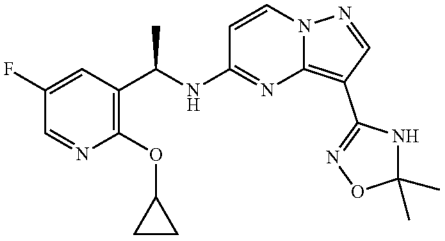
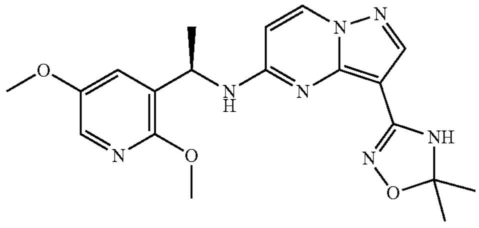

-continued
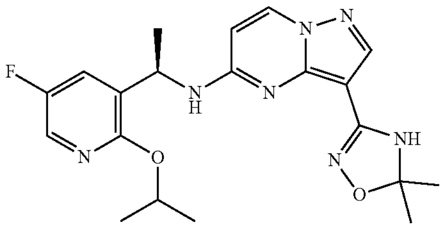
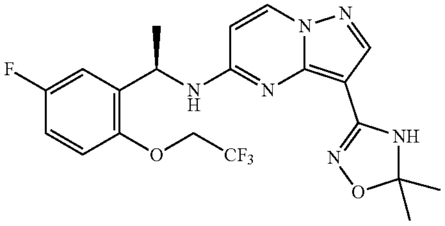
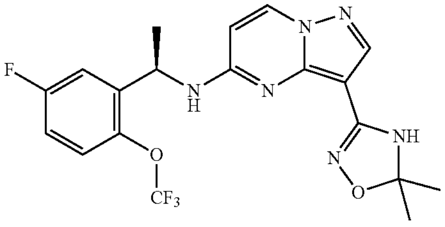
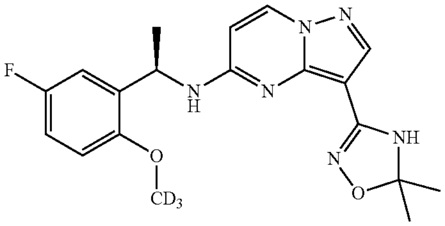
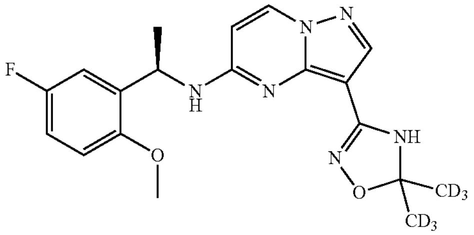
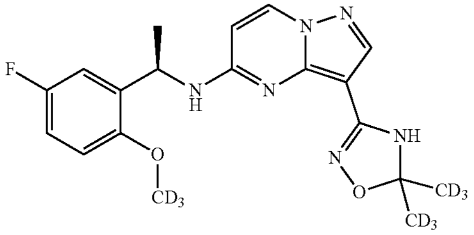
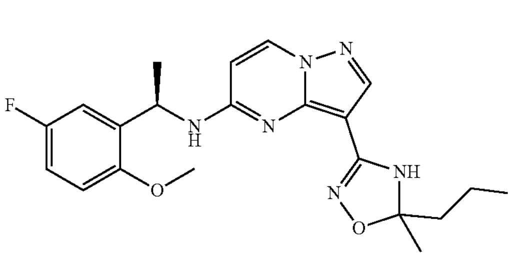
-continued
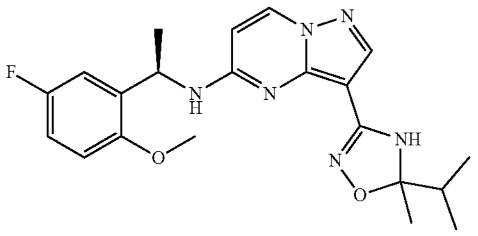
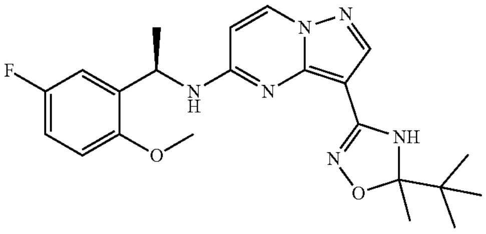
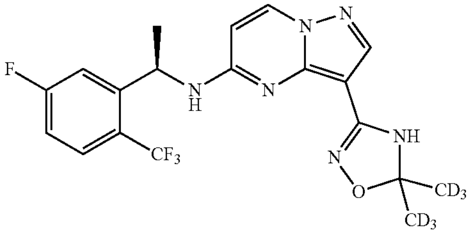
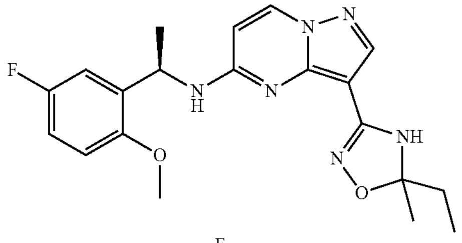
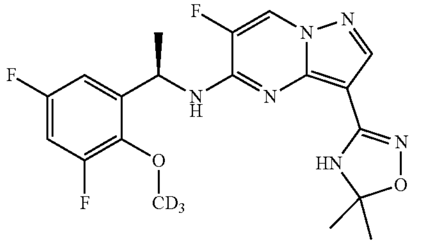
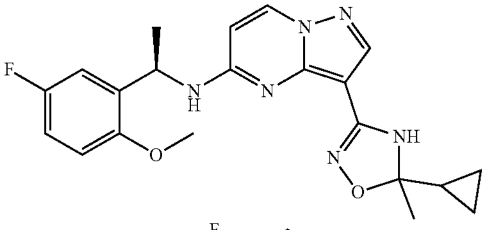
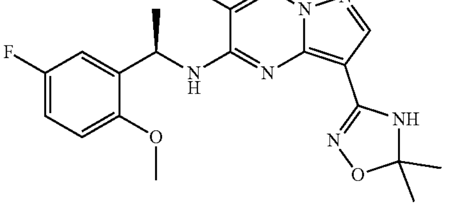

-continued
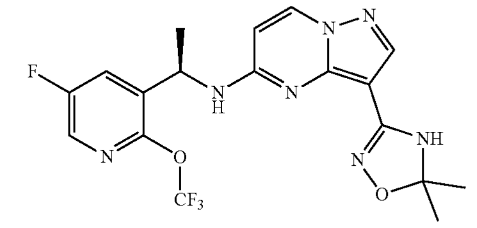
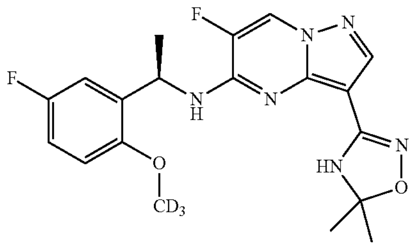
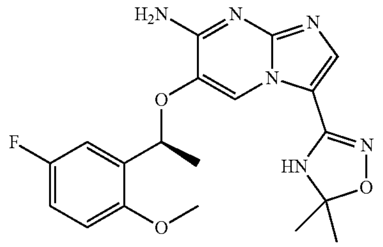
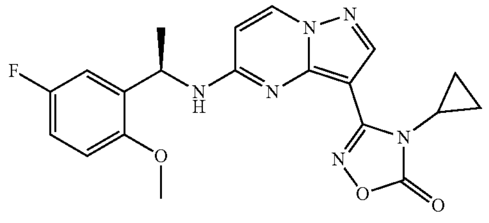
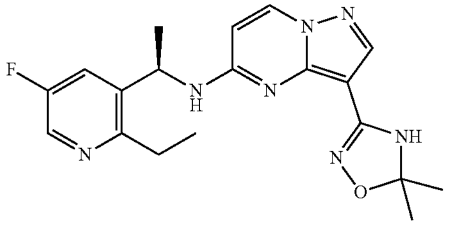
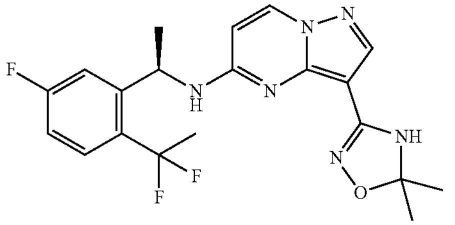
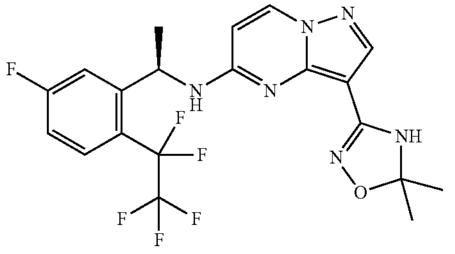
-continued
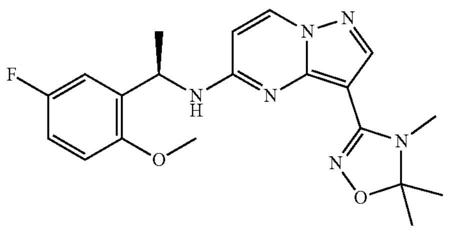
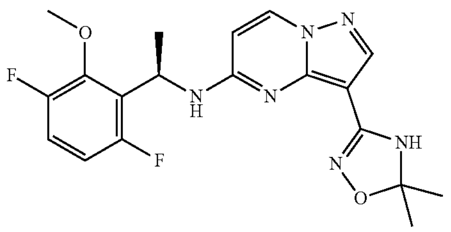
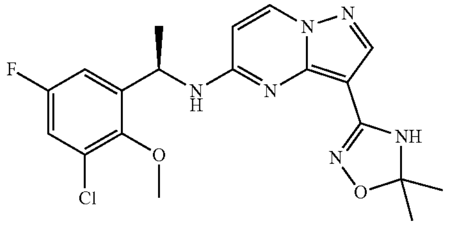
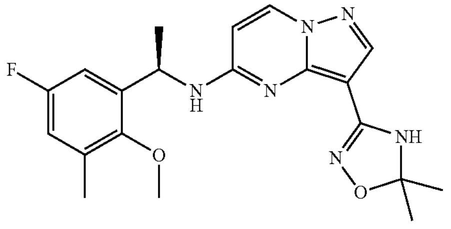
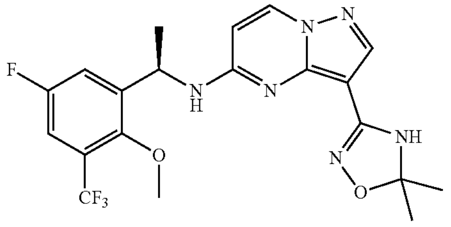
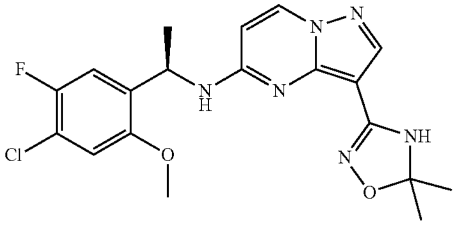
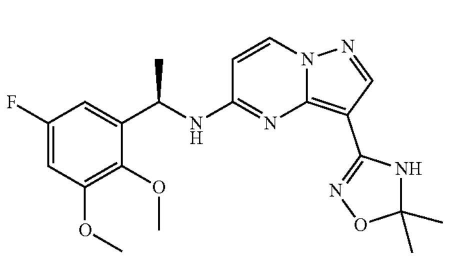

-continued
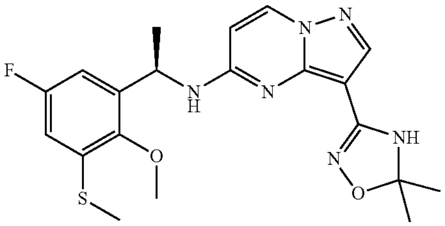
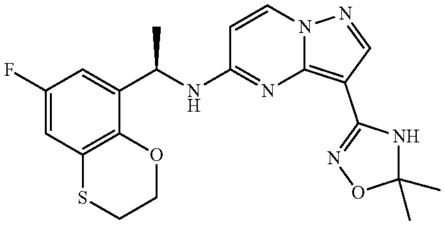
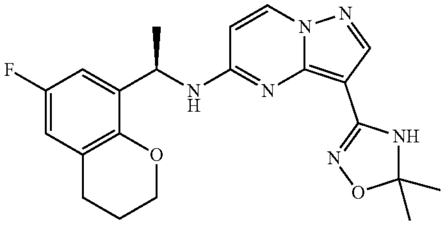
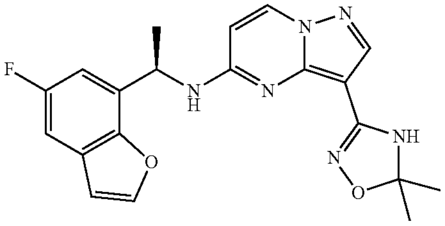
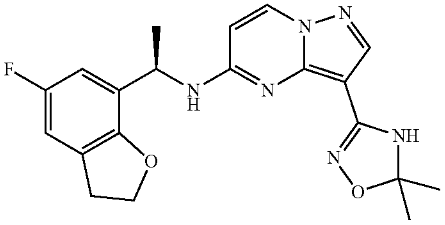
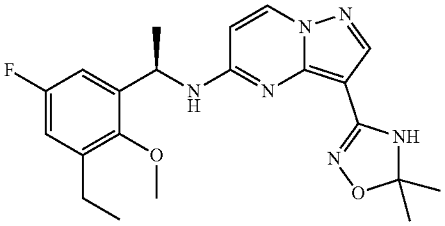
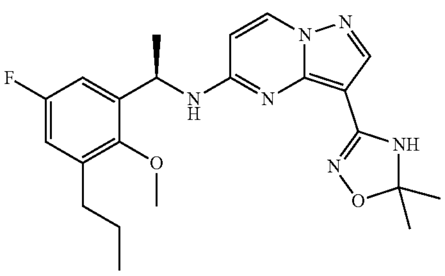
-continued
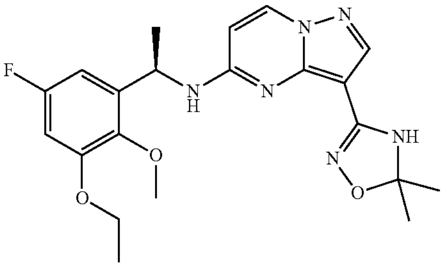
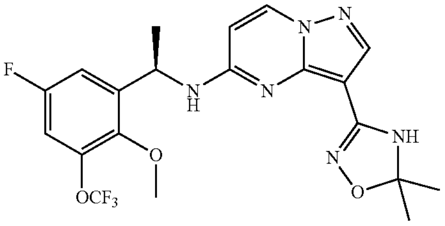
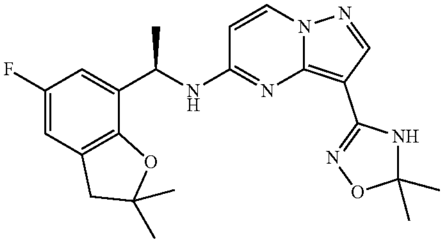
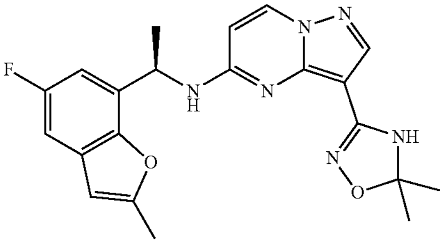
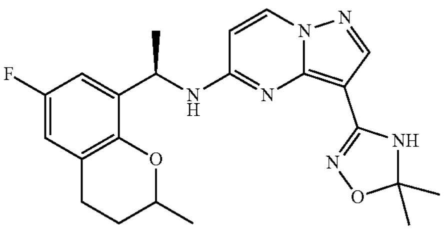
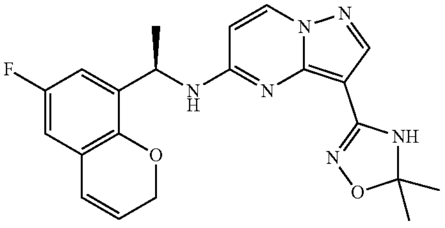
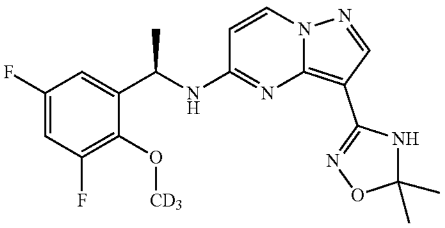

-continued
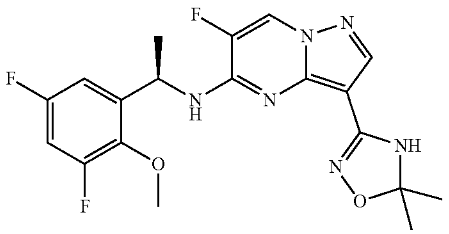
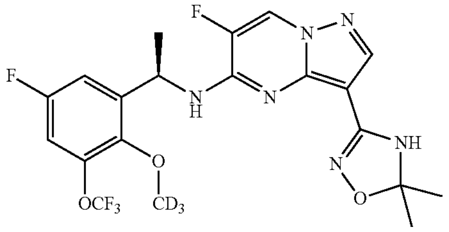
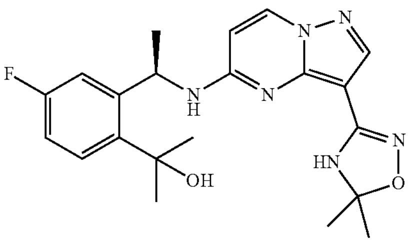
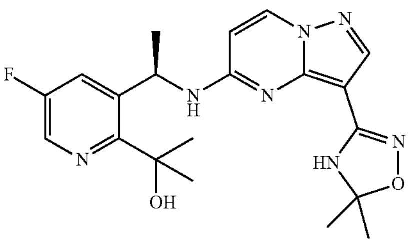
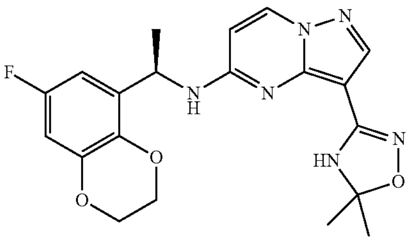
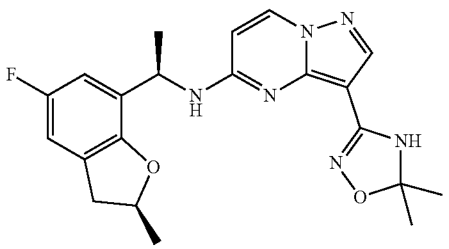
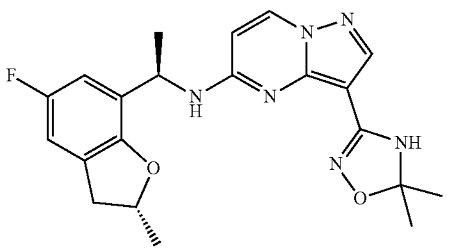
-continued
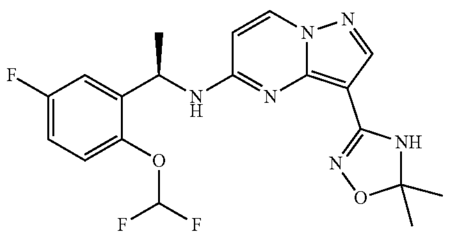
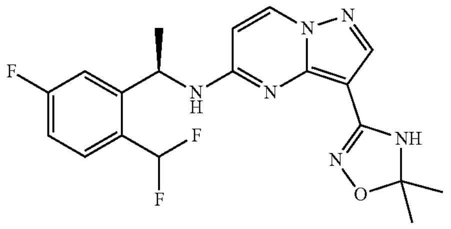
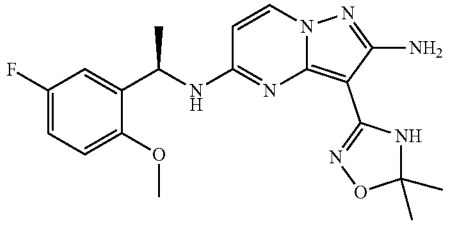
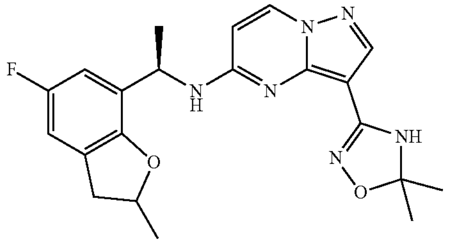
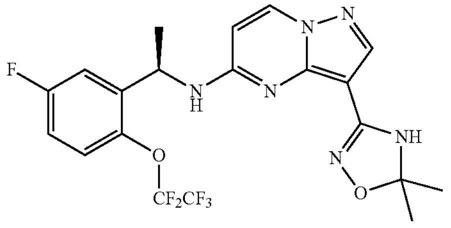
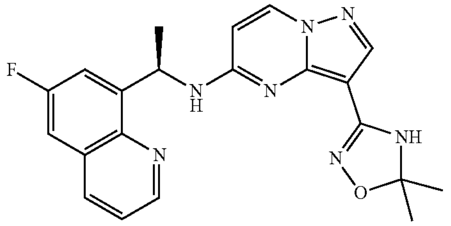
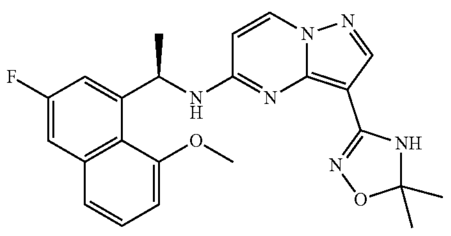

-continued
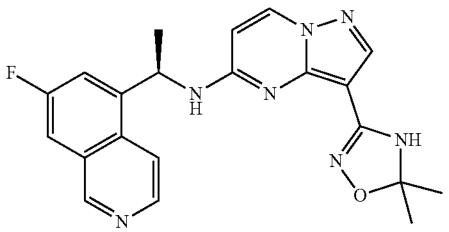
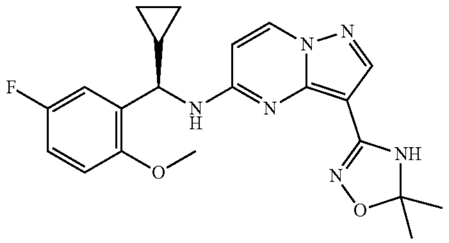
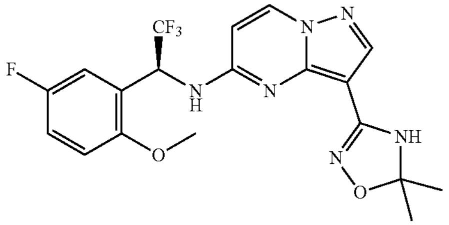
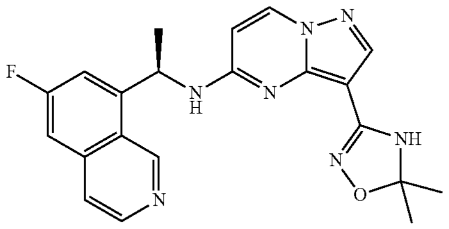
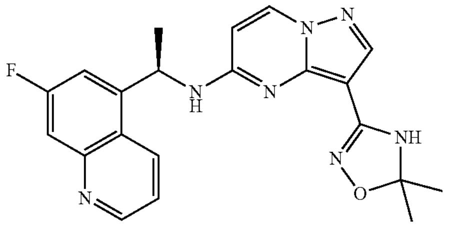
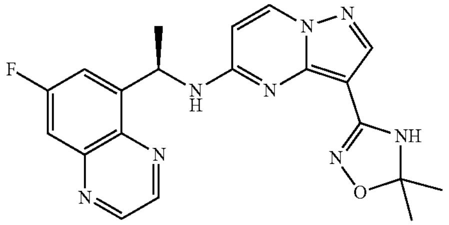
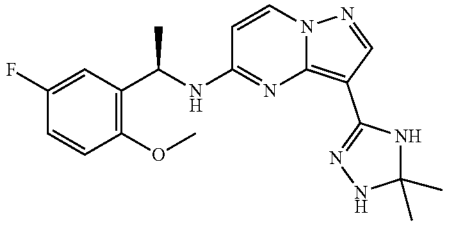
-continued
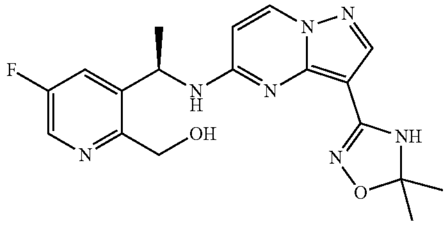
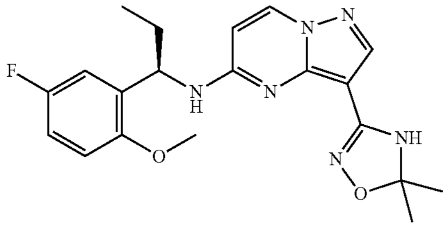
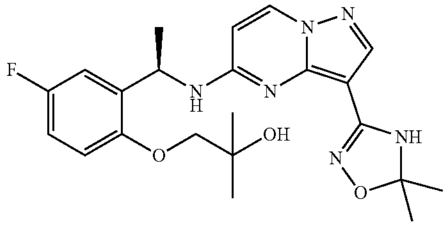
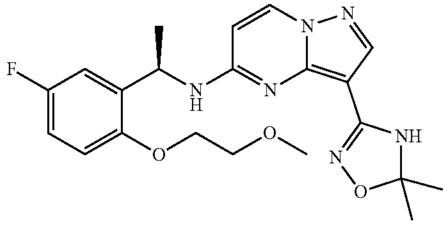
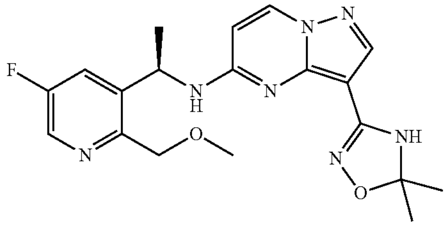
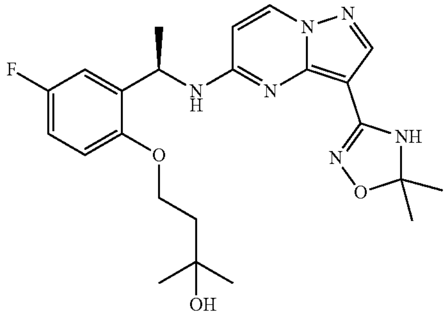
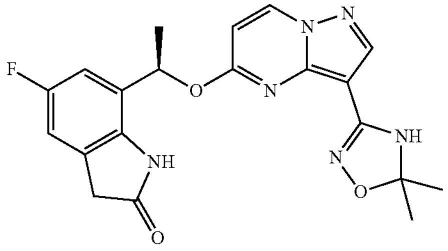

-continued

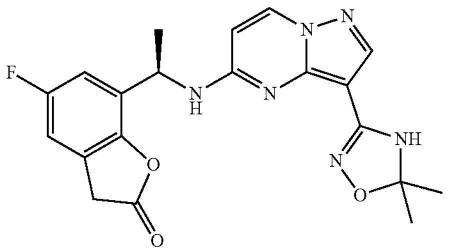

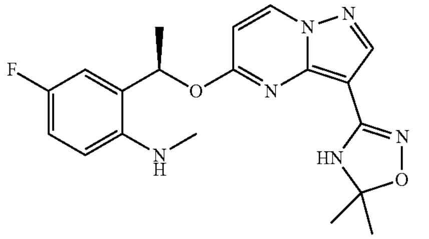

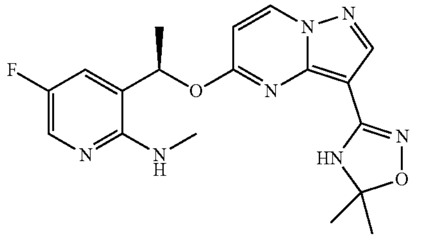

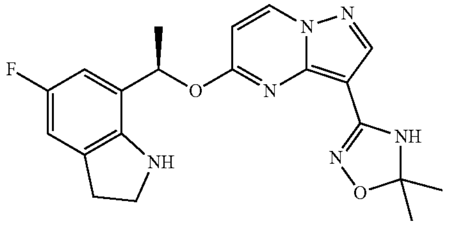

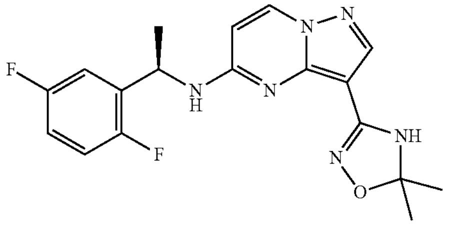

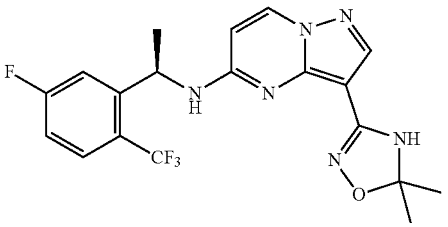

and

-continued

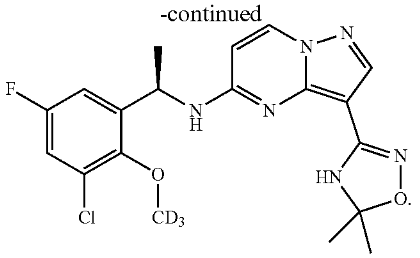

7. A compound of claim 1, or a tautomer are of, or a mesomer are of, or a racemate are of, or a mixture of a mesomer and a racemate are of, or a enantiomer are of, or a diastereomer are of, or a mixture of a enantiomer and a diastereomer are of, or a pharmaceutically acceptable salt are of, or a deuterated compound thereof, wherein the pharmaceutically acceptable salt is an inorganic acid salt or an organic acid salt, wherein the inorganic acid salt is selected from the group consisting of hydrochloride, hydrobromide, hydroiodate, sulfate, bisulfate, nitrate, phosphate and acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, hydroxyethanesulfonate, benzenesulfonate, salicylate, picrate, glutamate, ascorbate, camphorate, and camphor sulfonate.

8. A pharmaceutical composition comprising a therapeutically effective amount of a compound of claim 1, or a tautomer are of, or a mesomer are of, or a racemate are of, or a mixture of a mesomer and a racemate are of, or a enantiomer are of, or a diastereomer are of, or a mixture of a enantiomer and a diastereomer are of, or a pharmaceutically acceptable salt are of, or a deuterated compound thereof, and one or more pharmaceutically acceptable carriers, diluents or excipients.

9. A method for preventing or treating the diseases related to pathological characteristics mediated by ROS1, NTRK and ALK, or drug-resistant kinases thereof, comprising a step of: administering a use of the compound of formula I of claim 1, or a tautomer are of, or a mesomer are of, a racemate are of and a mixture of a mesomer and a racemate are of, or a enantiomer are of, a diastereomer are of and a mixture of a enantiomer and a diastereomer are of, or a pharmaceutically acceptable salt are of, or a deuterated compound thereof to a subject in need thereof.

10. The method of claim 9, wherein the disease related to pathological characteristics mediated by ROS1, NTRK, and ALK, or a drug-resistant kinase thereof etc. includes cancer, sarcoma and pain.

11. The method of claim 10, wherein the cancer is any one of breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tumor, peritoneal tumor, melanoma, glioma, glioblastoma, head and neck cancer, mastoid nephroma, leukemia, lymphoma, myeloma and thyroid tumor.

* * * * *